US011826230B2

(12) United States Patent
Ashraf et al.

(10) Patent No.: US 11,826,230 B2
(45) Date of Patent: Nov. 28, 2023

(54) PACKAGE OF ABSORBENT ARTICLES UTILIZING A SHAPED NONWOVEN

(71) Applicant: The Procter & Gamble Company, Cincinnati, OH (US)

(72) Inventors: Arman Ashraf, Mason, OH (US); Paul Thomas Weisman, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 397 days.

(21) Appl. No.: 15/221,624

(22) Filed: Jul. 28, 2016

(65) Prior Publication Data
US 2017/0027774 A1 Feb. 2, 2017

Related U.S. Application Data

(60) Provisional application No. 62/199,524, filed on Jul. 31, 2015.

(51) Int. Cl.
*A61F 13/551* (2006.01)
*A61F 13/15* (2006.01)
(Continued)

(52) U.S. Cl.
CPC .. *A61F 13/55115* (2013.01); *A61F 13/15203* (2013.01); *A61F 13/15658* (2013.01);
(Continued)

(58) Field of Classification Search
CPC ....... A61F 13/15203; F17C 3/04; B32B 5/022
(Continued)

(56) References Cited

U.S. PATENT DOCUMENTS 4,333,979 A 6/1982 Sciaraffa et al.
4,514,345 A 4/1985 Johnson et al.
(Continued)

FOREIGN PATENT DOCUMENTS

CN 1209177 A 2/1999
CN 1441102 A 9/2003
(Continued)

OTHER PUBLICATIONS

U.S. Appl. No. 15/221,625, filed Jul. 28, 2016, Arman Ashraf, et al.
(Continued)

*Primary Examiner* — Anthony D Stashick
*Assistant Examiner* — Raven Collins
(74) *Attorney, Agent, or Firm* — Christian M. Best

(57) ABSTRACT

A package of personal care articles. Each of the personal care articles has a nonwoven substrate as a component. The nonwoven substrate can have a first surface defining a plane of the first surface and a non-regular pattern of a plurality of three-dimensional features extending outwardly from the plane of the first surface. The non-regular pattern can include a first zone of first three-dimensional features and a second zone of second three-dimensional features, wherein in at least one of the first or second zones of the plurality of three-dimensional features has a first three-dimensional feature having a first intensive property and a second three-dimensional feature having a second, different intensive property. The personal care articles can be compressed in the package.

13 Claims, 26 Drawing Sheets

(51) Int. Cl.
| | |
|---|---|
| *B65D 85/62* | (2006.01) |
| *B32B 5/02* | (2006.01) |
| *D04H 1/04* | (2012.01) |
| *B29C 48/03* | (2019.01) |
| *A61F 13/511* | (2006.01) |
| *D01D 5/08* | (2006.01) |
| *D01D 5/34* | (2006.01) |
| *B29L 9/00* | (2006.01) |
| *B29L 31/48* | (2006.01) |

(52) U.S. Cl.
CPC ...... *A61F 13/51104* (2013.01); *A61F 13/551* (2013.01); *A61F 13/55145* (2013.01); *B29C 48/03* (2019.02); *B32B 5/022* (2013.01); *B65D 85/62* (2013.01); *D04H 1/04* (2013.01); *A61F 2013/15373* (2013.01); *A61F 2013/15406* (2013.01); *A61F 2013/15422* (2013.01); *B29L 2009/00* (2013.01); *B29L 2031/4878* (2013.01); *B32B 2439/00* (2013.01); *B32B 2555/02* (2013.01); *D01D 5/08* (2013.01); *D01D 5/34* (2013.01); *D10B 2321/021* (2013.01); *D10B 2321/022* (2013.01); *D10B 2501/02* (2013.01)

(58) Field of Classification Search
USPC ........................................................ 206/438
See application file for complete search history.

(56) References Cited

U.S. PATENT DOCUMENTS

| | | | |
|---|---|---|---|
| 4,741,941 A | 5/1988 | Englebert et al. | |
| 4,970,104 A | 11/1990 | Radwanski | |
| 5,145,727 A | 9/1992 | Potts et al. | |
| 5,178,932 A | 1/1993 | Perkins et al. | |
| 5,302,220 A | 4/1994 | Terakawa et al. | |
| 5,334,289 A | 8/1994 | Trokhan et al. | |
| 5,368,858 A | 11/1994 | Hunziker | |
| 5,369,858 A | 12/1994 | Gilmore et al. | |
| 5,399,174 A | 3/1995 | Yeo et al. | |
| 5,514,523 A | 5/1996 | Trokhan et al. | |
| 5,575,874 A | 11/1996 | Griesbach et al. | |
| 5,599,420 A | 2/1997 | Yeo et al. | |
| 5,634,653 A | 6/1997 | Browning | |
| 5,643,653 A | 7/1997 | Griesbach, III et al. | |
| 5,725,927 A | 3/1998 | Zilg et al. | |
| 5,858,504 A | 1/1999 | Steven | |
| 5,895,623 A | 4/1999 | Trokhan et al. | |
| 5,916,661 A | 6/1999 | Benson et al. | |
| 6,139,941 A | 10/2000 | Jankevics et al. | |
| 6,319,455 B1 | 11/2001 | Kauschke et al. | |
| 6,331,268 B1 | 12/2001 | Kauschke et al. | |
| 6,331,345 B1 | 12/2001 | Kauschke et al. | |
| 6,361,638 B2 | 3/2002 | Takai et al. | |
| 6,383,431 B1 | 5/2002 | Dobrin et al. | |
| 6,395,957 B1 | 5/2002 | Chen et al. | |
| 6,436,512 B1 | 8/2002 | Kauschke et al. | |
| 6,632,504 B1 | 10/2003 | Gillespie et al. | |
| 6,673,418 B1 | 1/2004 | DeOlivera et al. | |
| 6,818,802 B2 | 11/2004 | Takai et al. | |
| 6,841,037 B2 | 1/2005 | Scherb et al. | |
| 6,888,046 B2 | 5/2005 | Toyoshima et al. | |
| 7,005,044 B2 | 2/2006 | Kramer et al. | |
| 7,168,473 B2 | 1/2007 | Geus et al. | |
| 7,255,759 B2 | 8/2007 | Debyser et al. | |
| 7,507,463 B2 | 3/2009 | Noda et al. | |
| 7,553,535 B2 | 6/2009 | Noda et al. | |
| 7,578,317 B2 | 8/2009 | Levine et al. | |
| 7,662,462 B2 | 2/2010 | Noda et al. | |
| 7,897,240 B2 | 3/2011 | Noda et al. | |
| 7,954,213 B2 | 6/2011 | Mizutani et al. | |
| 7,955,549 B2 | 6/2011 | Noda et al. | |
| 8,129,298 B2 | 3/2012 | Motomura et al. | |
| 8,143,177 B2 | 3/2012 | Noda et al. | |
| 8,183,431 B2 | 5/2012 | Noda et al. | |
| 8,273,941 B2 | 9/2012 | Uematsu et al. | |
| 8,304,600 B2 | 11/2012 | Noda et al. | |
| 8,574,209 B2 | 11/2013 | Nishitani et al. | |
| 8,585,666 B2 * | 11/2013 | Weisman | A61F 13/53 604/385.02 |
| 8,758,569 B2 | 6/2014 | Aberg et al. | |
| 8,778,137 B2 | 7/2014 | Nozaki et al. | |
| 8,853,108 B2 | 10/2014 | Ahoniemi et al. | |
| 8,865,965 B2 | 10/2014 | Sato et al. | |
| 8,906,275 B2 | 12/2014 | Davis et al. | |
| 9,095,477 B2 | 8/2015 | Yamaguchi et al. | |
| 9,156,229 B2 | 10/2015 | Yoda et al. | |
| 9,205,005 B2 | 12/2015 | Kikuchi et al. | |
| 9,314,383 B2 * | 4/2016 | Noda | A61F 13/4704 |
| 9,453,292 B2 | 9/2016 | Sommer et al. | |
| 9,453,303 B2 | 9/2016 | Aberg et al. | |
| 9,732,454 B2 | 8/2017 | Davis et al. | |
| 9,750,651 B2 | 9/2017 | Bianchi et al. | |
| 9,770,371 B2 | 9/2017 | Kanya et al. | |
| 9,877,876 B2 | 1/2018 | Huang et al. | |
| 9,903,070 B2 | 2/2018 | Mourad et al. | |
| 9,993,369 B2 | 6/2018 | Xu | |
| 10,123,916 B2 | 11/2018 | Weisman et al. | |
| 10,190,244 B2 | 1/2019 | Ashraf et al. | |
| 10,639,212 B2 | 5/2020 | Kanya et al. | |
| 10,858,768 B2 | 12/2020 | Ashraf et al. | |
| 2001/0029141 A1 | 10/2001 | Mizutani et al. | |
| 2002/0043369 A1 | 4/2002 | Vinegar et al. | |
| 2002/0119720 A1 | 8/2002 | Arora et al. | |
| 2002/0153271 A1 | 10/2002 | McManus et al. | |
| 2002/0193032 A1 | 12/2002 | Newkirk et al. | |
| 2003/0093045 A1 | 5/2003 | Jensen | |
| 2003/0119404 A1 | 6/2003 | Belau et al. | |
| 2003/0125687 A1 | 7/2003 | Gubernick et al. | |
| 2003/0161904 A1 | 8/2003 | Geus et al. | |
| 2003/0203162 A1 | 10/2003 | Christopher et al. | |
| 2003/0203196 A1 | 10/2003 | Trokhan et al. | |
| 2003/0203691 A1 | 10/2003 | Fenwick et al. | |
| 2003/0211802 A1 | 11/2003 | Keck et al. | |
| 2003/0213620 A1 | 11/2003 | Krueger | |
| 2004/0005457 A1 | 1/2004 | Delucia et al. | |
| 2004/0059309 A1 | 3/2004 | Nortman | |
| 2004/0126601 A1 | 7/2004 | Kramer et al. | |
| 2005/0148971 A1 | 7/2005 | Kuroda et al. | |
| 2006/0087053 A1 | 4/2006 | O'Donnell et al. | |
| 2006/0105075 A1 | 5/2006 | Otsubo | |
| 2006/0135927 A1 | 6/2006 | Zander et al. | |
| 2006/0189954 A1 | 8/2006 | Kudo et al. | |
| 2007/0026753 A1 | 2/2007 | Neely et al. | |
| 2007/0045143 A1 | 3/2007 | Clough et al. | |
| 2007/0045144 A1 | 3/2007 | Wheeler et al. | |
| 2007/0179466 A1 | 8/2007 | Tremblay et al. | |
| 2007/0298214 A1 | 12/2007 | Noda et al. | |
| 2007/0298667 A1 | 12/2007 | Noda et al. | |
| 2008/0149292 A1 | 6/2008 | Scherb | |
| 2008/0220161 A1 | 9/2008 | Sommer et al. | |
| 2009/0240222 A1 | 9/2009 | Tomoko et al. | |
| 2010/0036346 A1 | 2/2010 | Hammons | |
| 2010/0048072 A1 * | 2/2010 | Kauschke | A47L 13/16 442/1 |
| 2010/0062672 A1 | 3/2010 | Fare | |
| 2010/0224356 A1 | 9/2010 | Moore | |
| 2011/0073513 A1 | 3/2011 | Weisman et al. | |
| 2011/0123775 A1 | 5/2011 | Westwood | |
| 2011/0137624 A1 | 6/2011 | Weisman et al. | |
| 2011/0250378 A1 | 10/2011 | Eaton et al. | |
| 2012/0004633 A1 * | 1/2012 | R. Marcelo | A61F 13/4756 604/378 |
| 2012/0196091 A1 * | 8/2012 | Mizutani | D04H 1/70 428/171 |
| 2012/0238979 A1 | 9/2012 | Weisman et al. | |
| 2012/0238982 A1 | 9/2012 | Weisman et al. | |
| 2012/0315440 A1 | 12/2012 | Ichikawa et al. | |
| 2012/0316532 A1 | 12/2012 | Mccormick | |
| 2013/0112584 A1 * | 5/2013 | Gaspari | B65D 83/0805 206/494 |
| 2013/0139960 A1 | 6/2013 | Maruyama et al. | |

(56) References Cited

U.S. PATENT DOCUMENTS

| | | | |
|---|---|---|---|
| 2013/0167305 A1 | 7/2013 | Weisman et al. | |
| 2013/0171421 A1 | 7/2013 | Weisman et al. | |
| 2013/0320584 A1 | 12/2013 | Davis et al. | |
| 2014/0044934 A1 | 2/2014 | Bills et al. | |
| 2014/0088535 A1 | 3/2014 | Xu et al. | |
| 2014/0127460 A1 | 5/2014 | Xu et al. | |
| 2014/0163502 A1* | 6/2014 | Arizti | A61F 13/539 604/366 |
| 2014/0202711 A1 | 7/2014 | Scott et al. | |
| 2014/0234575 A1 | 8/2014 | Mitsuno et al. | |
| 2014/0276517 A1 | 9/2014 | Chester et al. | |
| 2014/0296815 A1 | 10/2014 | Takken et al. | |
| 2014/0305570 A1 | 10/2014 | Matsunaga et al. | |
| 2014/0324009 A1 | 10/2014 | Lee et al. | |
| 2014/0358101 A1 | 12/2014 | Kanya et al. | |
| 2015/0038933 A1 | 2/2015 | Day | |
| 2015/0173967 A1* | 6/2015 | Kreuzer | A61F 13/49001 604/361 |
| 2015/0209202 A1 | 7/2015 | Weisman et al. | |
| 2015/0257943 A1* | 9/2015 | Noel | A61F 13/4704 604/385.101 |
| 2015/0265473 A1* | 9/2015 | Hammons | A61F 13/5116 604/383 |
| 2015/0282999 A1 | 10/2015 | Arizti et al. | |
| 2016/0067119 A1 | 3/2016 | Weisman et al. | |
| 2016/0106633 A1 | 4/2016 | Nagata et al. | |
| 2016/0129661 A1 | 5/2016 | Arora et al. | |
| 2016/0136009 A1 | 5/2016 | Weisman et al. | |
| 2016/0235597 A1* | 8/2016 | Ehrnsperger | A61F 13/55115 |
| 2016/0362825 A1 | 12/2016 | Novarino et al. | |
| 2017/0014281 A1 | 1/2017 | Xie et al. | |
| 2017/0014291 A1 | 1/2017 | Kie et al. | |
| 2017/0027774 A1 | 2/2017 | Ashraf et al. | |
| 2017/0029993 A1 | 2/2017 | Ashraf et al. | |
| 2017/0029994 A1 | 2/2017 | Ashraf et al. | |
| 2017/0056256 A1 | 3/2017 | Smith et al. | |
| 2017/0121873 A1 | 5/2017 | Kimura et al. | |
| 2017/0137980 A1 | 5/2017 | Kauschke et al. | |
| 2017/0175313 A1 | 6/2017 | Song et al. | |
| 2017/0191198 A1 | 7/2017 | Ashraf et al. | |
| 2017/0258650 A1 | 9/2017 | Rosati et al. | |
| 2017/0314163 A1 | 11/2017 | Sommer et al. | |
| 2017/0348163 A1 | 12/2017 | Lakso et al. | |
| 2018/0098893 A1 | 4/2018 | Viens | |
| 2018/0168893 A1 | 6/2018 | Ashraf et al. | |
| 2018/0214318 A1 | 8/2018 | Ashraf et al. | |
| 2018/0214321 A1 | 8/2018 | Ashraf et al. | |
| 2018/0216269 A1 | 8/2018 | Ashraf et al. | |
| 2018/0216270 A1 | 8/2018 | Ashraf et al. | |
| 2018/0216271 A1 | 8/2018 | Ashraf et al. | |
| 2018/0344544 A1 | 12/2018 | Tally | |
| 2019/0003079 A1 | 1/2019 | Ashraf et al. | |
| 2019/0003080 A1 | 1/2019 | Ashraf et al. | |
| 2019/0112737 A1 | 4/2019 | Ashraf et al. | |
| 2019/0388578 A1 | 12/2019 | Aviles | |
| 2020/0038262 A1 | 2/2020 | Aviles et al. | |
| 2020/0054501 A1 | 2/2020 | Seto et al. | |
| 2020/0299881 A1 | 9/2020 | Ashraf | |
| 2021/0040661 A1 | 2/2021 | Ashraf et al. | |
| 2021/0077319 A1 | 3/2021 | Weber et al. | |
| 2021/0169710 A1 | 6/2021 | Ashraf et al. | |
| 2021/0214858 A1 | 7/2021 | Sommer et al. | |
| 2022/0074094 A1 | 3/2022 | Ashraf et al. | |

FOREIGN PATENT DOCUMENTS

| | | |
|---|---|---|
| CN | 1685099 | 10/2005 |
| CN | 101443499 A | 5/2009 |
| CN | 103108616 A | 5/2013 |
| CN | 104507436 A | 4/2015 |
| CN | 105473114 A | 4/2016 |
| CN | 108366888 A | 8/2018 |
| CN | 110022822 A | 7/2019 |
| EP | 1227181 | 12/2001 |
| EP | 1234906 | 1/2002 |
| EP | 1323400 A2 | 7/2003 |
| EP | 1338262 A1 | 8/2003 |
| EP | 2660377 | 4/2014 |
| JP | S4827070 A | 4/1973 |
| JP | S4853061 A | 7/1973 |
| JP | H04327255 A | 11/1992 |
| JP | 2003052752 A | 2/2003 |
| JP | 2006510456 A | 3/2006 |
| JP | 2008509786 A | 4/2008 |
| JP | 2009136349 A | 6/2009 |
| JP | 2011-015707 | 1/2011 |
| JP | 2012075638 A | 4/2012 |
| JP | 5399174 B2 | 11/2013 |
| JP | 2013244256 A | 12/2013 |
| JP | 2014070299 A | 4/2014 |
| JP | 2014-097257 | 5/2014 |
| JP | 2014515986 A | 7/2014 |
| JP | 2014-188042 | 10/2014 |
| JP | 2014234345 A | 12/2014 |
| KR | 100988698 B1 | 10/2010 |
| RU | 2388860 C2 | 5/2010 |
| WO | 9716751 A1 | 5/1997 |
| WO | 03057117 A1 | 7/2003 |
| WO | WO201286730 | 6/2012 |
| WO | WO 2003-015681 | 2/2013 |
| WO | WO201318846 | 2/2013 |
| WO | WO 2013-084977 | 6/2013 |
| WO | WO201399625 | 7/2013 |
| WO | WO2013145966 | 10/2013 |
| WO | 2015000774 A1 | 1/2015 |
| WO | WO 2017/105997 A1 | 6/2017 |
| WO | WO2017110695 | 6/2017 |
| WO | 2020226951 A1 | 11/2020 |

OTHER PUBLICATIONS

U.S. Appl. No. 15/221,626, filed Jul. 28, 2016, Arman Ashraf, et al.
U.S. Appl. No. 15/221,628, filed Jul. 28, 2016, Arman Ashraf, et al.
U.S. Appl. No. 15/879,474, filed Feb. 5, 2018, Arman Ashraf, et al.
U.S. Appl. No. 15/879,477, filed Feb. 5, 2018, Arman Ashraf, et al.
U.S. Appl. No. 15/879,480, filed Jan. 25, 2018, Arman Ashraf, et al.
U.S. Appl. No. 15/879,485, filed Jan. 25, 2018, Arman Ashraf, et al.
U.S. Appl. No. 15/881,910, filed Jan. 29, 2018, Arman Ashraf, et al.
U.S. Appl. No. 16/019,724, filed Jun. 29, 2018, Arman Ashraf, et al.
U.S. Appl. No. 16/019,785, filed Jun. 29, 2018, Arman Ashraf, et al.
Written Opinion, PCT/US2016/044349, dated Sep. 23, 2016.
All Office Actions, U.S. Appl. No. 16/214,526.
All Office Actions, U.S. Appl. No. 17/076,847.
All Office Actions: U.S. Appl. No. 17/529,345.
Unpublished U.S. Appl. No. 17/629,345, filed Nov. 18, 2021, to Arman Ashraf et al.
All Office Actions, U.S. Appl. No. 15/493,170, filed Apr. 21, 2017.
All Office Actions; U.S. Appl. No. 17/213,873, filed Mar. 26, 2021.
Extended EP Search Report and Written Opinion for 22179135.3 dated Oct. 5, 2022, 7 Pages.
All Office Actions; U.S. Appl. No. 18/192,741, filed Mar. 30, 2023.
Unpublished U.S. Appl. No. 18/192,741, filed Mar. 30, 2023, to Arman Ashraf et al.
All Office Actions; U.S. Appl. No. 18/301,526, filed Apr. 17, 2023.
Unpublished U.S. Appl. No. 18/301,526, filed Apr. 17, 2023, to Arman Ashraf et al.
PCT International Search Report U.S. Appl. No. 15/221,624 dated Sep. 23, 2016—6 pages.
All Office Actions U.S. Appl. No. 15/221,625.
All Office Actions U.S. Appl. No. 15/221,626.
All Office Actions U.S. Appl. No. 15/221,628.
PCT International Search Report Application U.S. Appl. No. 15/879,474 dated Apr. 11, 2018—5 pages.
PCT International Search Report Application U.S. Appl. No. 15/879,480 dated Apr. 11, 2018—5 pages.
All Office Actions Application U.S. Appl. No. 15/840,455.
All Office Actions Application U.S. Appl. No. 15/879,474.
All Office Actions Application U.S. Appl. No. 15/879,477.
All Office Actions Application U.S. Appl. No. 15/879,480.

(56) References Cited

OTHER PUBLICATIONS

All Office Actions Application U.S. Appl. No. 15/879,485.
All Office Actions Application U.S. Appl. No. 15/881,910.
All Office Actions Application U.S. Appl. No. 16/019,724.
All Office Actions Application U.S. Appl. No. 16/019,785.
Dec. 13, 2017 Arman Ashraf, et al.
Feb. 5, 2018 Arman Ashraf, et al.
Jan. 25, 2018 Arman Ashraf, et al.
Jan. 29, 2018 Arman Ashraf, et al.
Jun. 29, 2018 Arman Ashraf, et al.

* cited by examiner

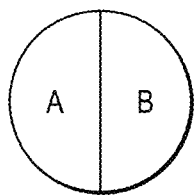 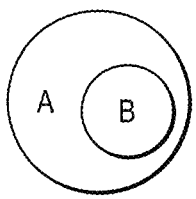 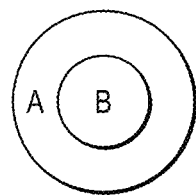
FIG. 5A  FIG. 5B  FIG. 5C
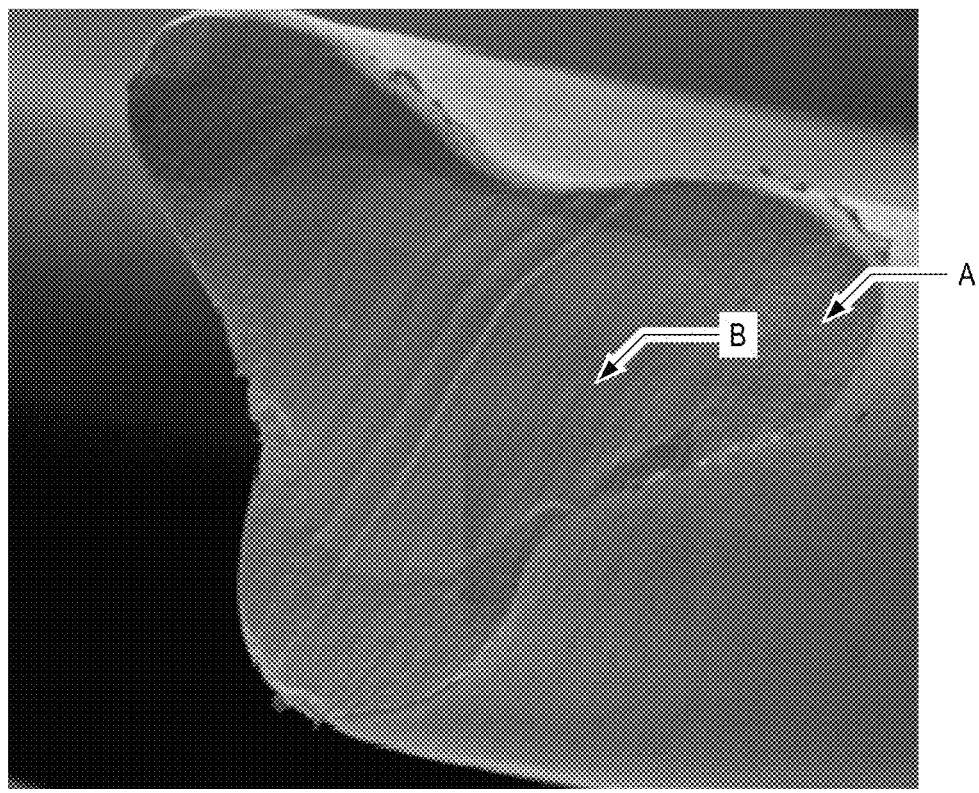
FIG. 6

PACKAGE OF ABSORBENT ARTICLES UTILIZING A SHAPED NONWOVEN

TECHNICAL FIELD

This invention relates to shaped, three-dimensional nonwoven fabrics and articles made with shaped, three-dimensional nonwoven fabrics.

BACKGROUND OF THE INVENTION

Nonwoven fabrics are useful for a wide variety of applications, including absorbent personal care products, garments, medical applications, and cleaning applications. Nonwoven personal care products include infant care items such as diapers, child care items such as training pants, feminine care items such as sanitary napkins, and adult care items such as incontinence products, pads, and pants. Nonwoven garments include protective workwear and medical apparel such as surgical gowns. Other nonwoven medical applications include nonwoven wound dressings and surgical dressings. Cleaning applications for nonwovens include towels and wipes. Still other uses of nonwoven fabrics are well known. The foregoing list is not considered exhaustive.

Various properties of nonwoven fabrics determine the suitability of nonwoven fabrics for different applications. Nonwoven fabrics may be engineered to have different combinations of properties to suit different needs. Variable properties of nonwoven fabrics include liquid-handling properties such as wettability, distribution, and absorbency, strength properties such as tensile strength and tear strength, softness properties, durability properties such as abrasion resistance, and aesthetic properties. The physical shape of a nonwoven fabric also affects the functionality and aesthetic properties of the nonwoven fabric. Nonwoven fabrics are initially made into sheets which, when laid on a flat surface, may have a substantially planar, featureless surface or may have an array of surface features such as aperture or projections, or both. Nonwoven fabrics with apertures or projections are often referred to as three-dimensional shaped nonwoven fabrics. The present disclosure relates to three-dimensional shaped nonwoven fabrics.

Despite prior advances in the art of nonwoven fabrics, there remains a need for improved nonwoven fabrics having three-dimensional surface features.

Further, there remains a need for processes and equipment for manufacturing improved nonwoven fabrics having three-dimensional surface features.

Further, there remains a need for articles, including absorbent articles, utilizing improved nonwoven fabrics having three-dimensional surface features.

Further, there remains a need for absorbent articles utilizing nonwoven fabrics having three-dimensional surface features and which can be packaged in a compressed form while minimizing the loss of the three-dimensional surface features when opened from the package.

Further, there remains a need for absorbent articles utilizing soft, spunbond nonwoven fabrics having three-dimensional surface features that have reduced fuzzing properties when in use.

Additionally, there remains a need for packages of absorbent articles comprising soft nonwoven materials that have a reduced in-bag stack height compared to conventional absorbent article packages so the packages are convenient for caregivers to handle and store and so that manufacturers enjoy low distribution costs without a loss of aesthetics clarity, absorbency, or softness of the as-made absorbent article.

SUMMARY OF THE INVENTION

A package of personal care articles is disclosed. Each of the personal care articles has a nonwoven substrate as a component. The nonwoven substrate can have a first surface defining a plane of the first surface and a non-regular pattern of a plurality of three-dimensional features extending outwardly from the plane of the of the first surface. The non-regular pattern can include a first zone of first three-dimensional features and a second zone of second three-dimensional features, wherein in at least one of the first or second zones of the plurality of three-dimensional features has a first three-dimensional feature having a first intensive property and a second three-dimensional feature having a second, different intensive property. The personal care articles can be compressed in the package.

BRIEF DESCRIPTION OF THE DRAWINGS

FIG. 5A is a schematic drawing illustrating the cross-section of a filament made with a primary component A and a secondary component B in a side-by-side arrangement.

FIG. 5B is a schematic drawing illustrating the cross-section of a filament made with a primary component A and a secondary component B in an eccentric sheath/core arrangement.

FIG. 5C is a schematic drawing illustrating the cross-section of a filament made with a primary component A and a secondary component B in a concentric sheath/core arrangement.

FIG. 6 is a perspective view photograph of a tri-lobal, bicomponent fiber.

DETAILED DESCRIPTION OF THE INVENTION

The present disclosure provides a shaped nonwoven fabric directly formed on a shaped forming belt with continuous spunbond filaments in a single forming process. The fabric of the present disclosure can assume a shape which corresponds to the shape of the forming belt. A fabric of the present disclosure made on a forming belt of the present disclosure in a method of the present disclosure can be particularly beneficial for use in personal care articles, garments, medical products, and cleaning products.

The beneficial features of the nonwoven fabric will be described in some embodiments herein in the context of an overall area of the nonwoven fabric. The overall area can be an area determined by dimensions suitable for certain uses, for which the various features of the invention provide beneficial properties. For example, the overall area of a fabric can be that of a fabric having dimensions making it suitable for use as a topsheet, backsheet nonwoven, acquisition layer, distribution layer, or other component layer for a diaper, or a topsheet, backsheet nonwoven, acquisition layer, distribution layer, or other component layer for a sanitary napkin, a topsheet, backsheet nonwoven, acquisition layer, distribution layer, or other component layer for an adult incontinent pad or pant, or a pad for a floor cleaning implement. Thus, the overall area can be based on width and length dimensions ranging from 10 cm wide to 50 cm wide and from 15 cm long to 100 cm long, resulting in overall areas of from 150 $cm^2$ to 500 $cm^2$. The aforementioned ranges include as if explicitly stated every integer dimension between the range boundaries. By way of example, an overall area of 176 $cm^2$ defined by a width of 11 cm and a length of 16 cm is disclosed in the above ranges. As will be understood from the description herein, the overall area of a shaped nonwoven fabric may be a smaller area than the area of the web of nonwoven fabric of which it is a part when it is commercially made. That is, in a given commercially made web of nonwoven fabric, there can be a plurality of shaped nonwoven fabrics of the invention, each of the shaped nonwoven fabrics of the invention having an overall area less than the area of the web on which it is made.

Figure 1:
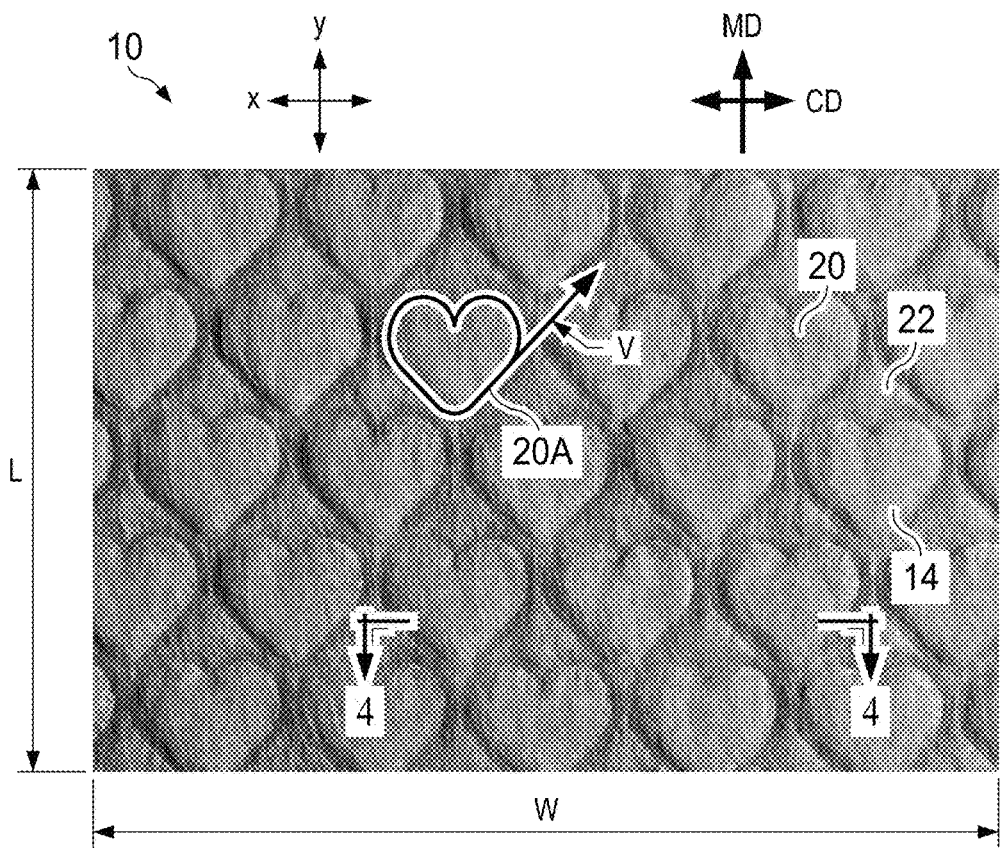
FIG. 1 is a photograph of an embodiment of the present disclosure.
Figure 2:
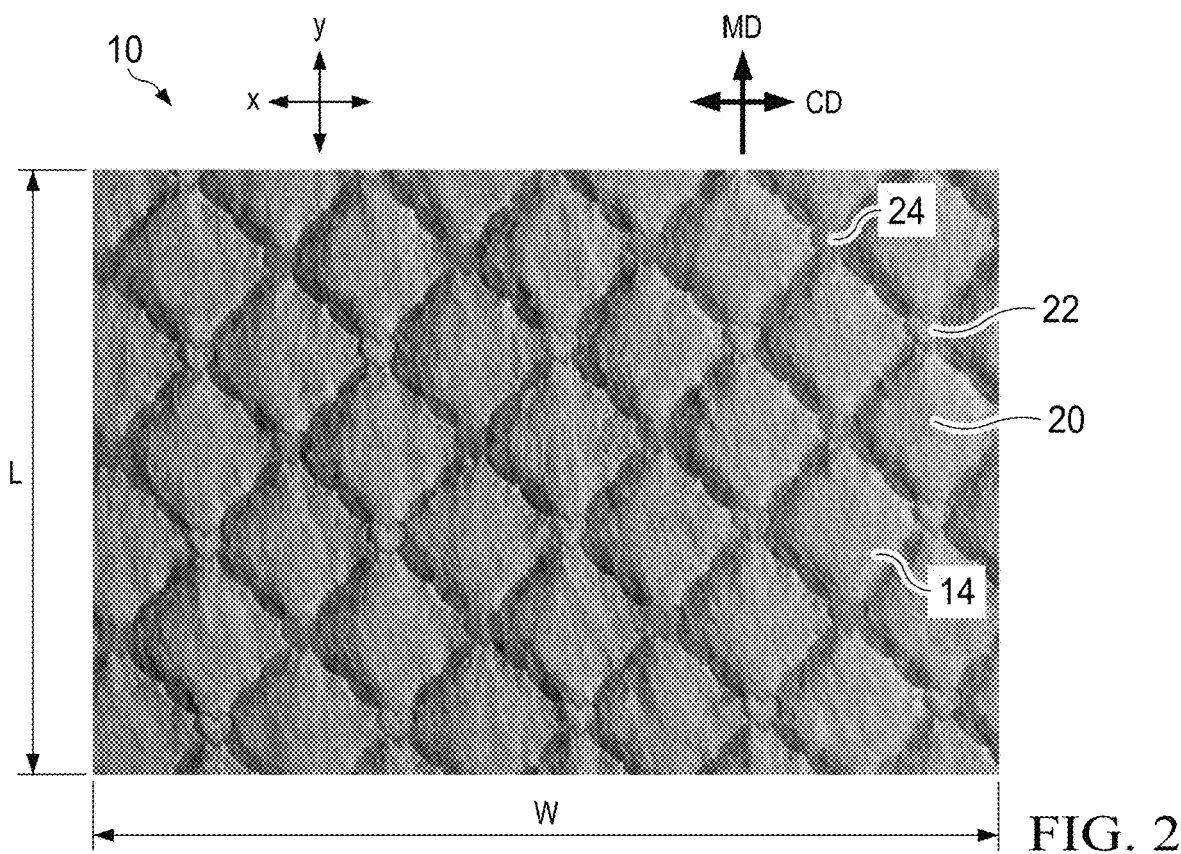
FIG. 2 is a photograph of an embodiment of the present disclosure.
Figure 3:
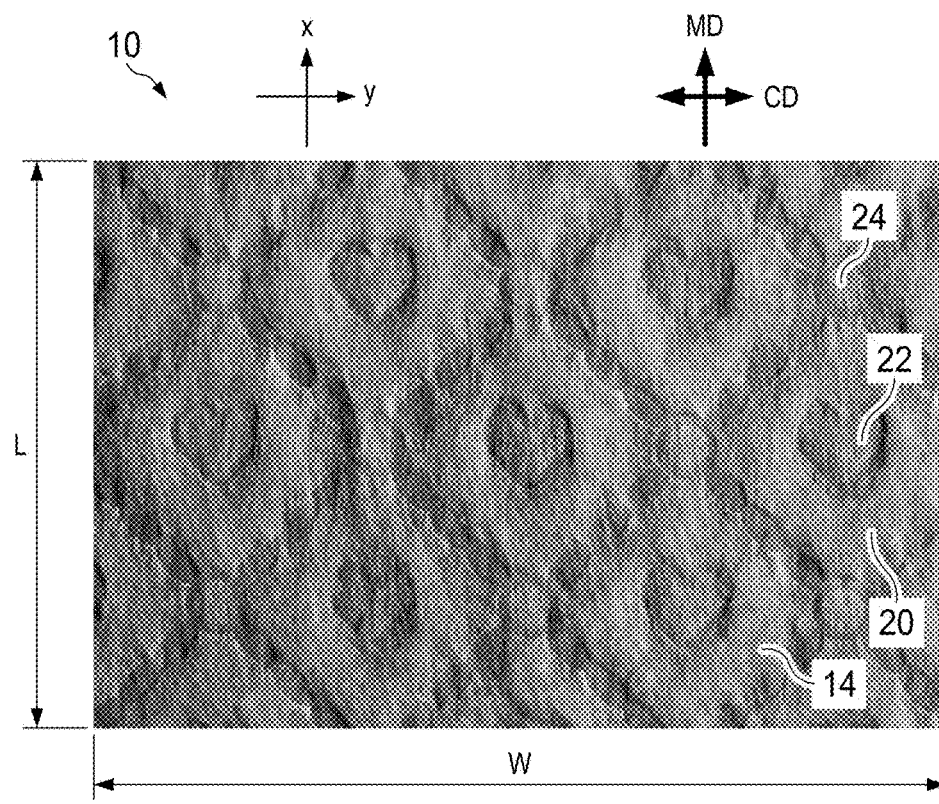
FIG. 3 is a photograph of an embodiment of the present disclosure.
Figure 4:
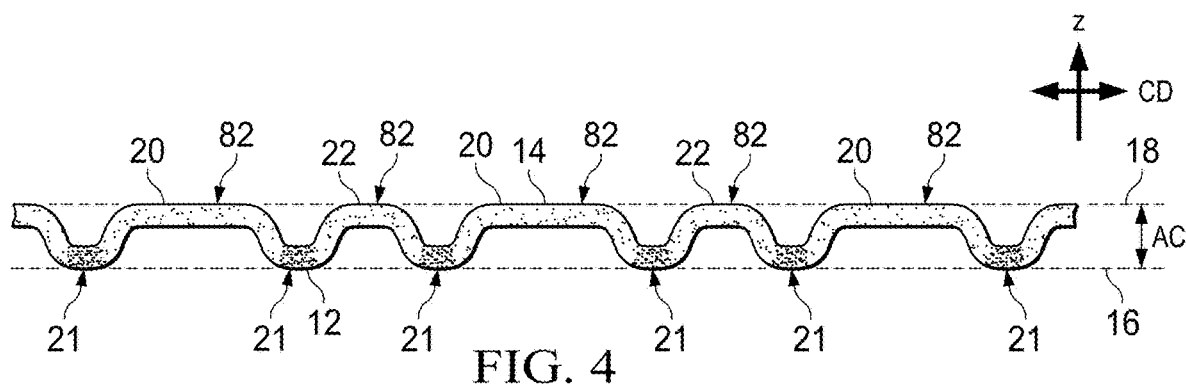
FIG. 4 is a cross-section of a portion of a fabric of the present disclosure as indicated in FIG. 1.

Photographs of representative embodiments of shaped nonwoven fabrics 10 are shown in FIGS. 1-3. The shaped nonwoven fabric 10 can be a spunbond nonwoven substrate having a first surface 12 and a second surface 14. In FIGS. 1-3, second surface 14 is facing the viewer and is opposite the first surface 12, which is unseen but is depicted in FIG. 4. The term "surface" is used broadly to refer to the two sides of a web for descriptive purposes, and is not intended to infer any necessary flatness or smoothness. Although the shaped nonwoven fabric 10 is soft and flexible, it will be described in a flattened condition the context of one or more X-Y planes parallel to the flattened condition, and which correspond in web-making technology to the plane of the cross-machine direction, CD, and machine direction, MD, respectively, as shown in FIGS. 1-3. The length, L, in the MD and the width, W, in the CD determine the overall area A for the fabric 10. As shown in FIG. 4, which is a cross section of a portion of the fabric 10 shown in FIG. 1, for descriptive purposes the three-dimensional features of the shaped nonwoven fabric are described as extending outwardly in a Z-direction from an X-Y plane of the first surface 16 (see, FIG. 4). In an embodiment, a maximum dimension of three-dimensional features in the Z-direction can define the maximum distance between the plane of the first surface 16 and an X-Y plane of the second surface 18, which distance can be measured as the average caliper AC of the shaped nonwoven fabric 10. The average caliper can be determined via optical, non-contact means, or it can be determined by instruments involving spaced apart flat plates that measure the caliper of the nonwoven placed between them under a predetermined pressure. It is not necessary that all the three-dimensional features have the same Z-direction maximum dimension, but a plurality of three-dimensional features can have substantially the same Z-direction maximum dimension determined by the spinning process and the properties of the forming belt, discussed below.

As shown in FIGS. 1-4, the fabric 10 can have a regular, repeating pattern of a plurality of discrete, recognizably different three-dimensional features, including a first three-dimensional feature 20 and a second three-dimensional feature 22, and a third three-dimensional feature 24, as shown in FIGS. 2 and 3. For example, in FIG. 1, heart-shaped first three-dimensional feature 20 is recognizably different from the smaller, generally triangular-shaped second three-dimensional feature 22. The recognizable differences can be visual, such as recognizably different sizes and/or shapes.

The three-dimensional features of the fabric 10 are formed by spinning fibers directly onto a forming belt having a pattern of corresponding three-dimensional features. In one sense the fabric 10 is molded onto a forming belt that determines the shapes of the three-dimensional features of the fabric 10. However, importantly, as described herein, the apparatus and method of the invention produce the fabric 10 such that in addition to taking the shape of the forming belt, because of the attributes of the forming belt and the apparatus for forming the fabric is imparted with beneficial properties for use in personal care articles, garments, medical products, and cleaning products. Specifically, because of the nature of the forming belt and other apparatus elements, as described below, the three-dimensional features of the fabric 10 have intensive properties that can differ from feature to feature in ways that provide for beneficial properties of the fabric 10 when used in personal care articles, garments, medical products, and cleaning products. For example, first three-dimensional feature 20 can have a basis weight or density that is different from the basis weight or density of second three-dimensional feature 22, and both can have a basis weight or density that is different from that of third three-dimensional feature 24, providing for beneficial aesthetic and functional properties related to fluid acquisition, distribution and/or absorption in diapers or sanitary napkins.

The intensive property differential between the various three-dimensional features of fabric 10 is believed to be due to the fiber distribution and compaction resulting from the apparatus and method described below. The fiber distribution occurs during the fiber spinning process, as opposed to, for example, a post making process such as hydroentangling or embossing processes. Because the fibers are free to move during the spinning process, with the movement determined by the nature of the features and air permeability of the forming belt and other processing parameters, the fibers are believed to be more stable and permanently formed in fabric 10.

As can be seen in FIGS. 1-3 and as understood from the description herein, the distinct three-dimensional features can be bounded by relatively higher density (with respect to the interior of a three-dimensional feature) regions that can be in the form of a closed figure (such as the heart shape in FIGS. 1 and 3, and the diamond shape of FIGS. 2 and 3). The closed figure can be a curvilinear closed figure such as the heart shape in FIGS. 1 and 3. The relatively higher density regions can be the regions of the fabric 10 that are most closely adjacent in the Z-direction to first surface 12, such as regions 21 as shown in FIG. 4, and with can lie at least partially in or on first plane 16 when in a flattened condition. For example, as shown in FIG. 1, first three-dimensional feature 20 is heart shaped, and as indicated as one exemplary first three-dimensional feature 20A is defined by a curvilinear closed heart-shaped element. A curvilinear element can be understood as a linear element having at any point along its length a tangential vector V, with the closed shape being such that the tangential vector V has both MD and CD components that change values over greater than 50% of the length of the linear element of the closed figure. Of course, the figure need not be entirely 100% closed, but the linear element can have breaks that do not take away from the overall impression of a closed figure. As discussed below in the context of the forming belt, the relatively higher density curvilinear closed heart-shaped element is formed by a corresponding closed heart-shaped raised element on the forming belt to make the closed figure of a heart on fabric 10. In a repeating pattern, the individual shapes (in the case of first three-dimensional feature in FIG. 1, a heart shape) can result in aesthetically pleasing, soft, pillowy features across the overall area OA of the second surface 14 of fabric 10. In an embodiment in which the fabric 10 is used as a topsheet for a diaper or sanitary napkin, the second surface 14 of fabric 10 can be body-facing to deliver superior aesthetic and performance benefits related to softness, compression resistance, and fluid absorption.

Specifically, in the regular repeating pattern of closed, three-dimensional features shown in FIG. 1-3, it is believed, without being bound by theory, that the dimensions of the various features, the average basis weight of the entire fabric 10 across its overall area, and other processing parameters described below which define the differing intensive properties contribute to a beneficial improvement in compression recovery. It is believed that the plurality of relatively closely spaced, relatively small, and relatively pillowy three-dimensional features act as springs to resist compression and recover once a compressive force is removed. Compression recovery is important in topsheets, backsheet nonwovens, acquisition layers, distribution layers, or other component layers of personal care articles such as diapers, sanitary napkins, or adult incontinent pads, diapers, or pants for example, because such articles are typically packaged and folded in compressed conditions. Manufacturers of personal care products desire to retain most, if not all of the as-made caliper for aesthetic and performance purposes. The three-dimensionality of formed features provide important aesthetic benefits due to the look and feel of softness and pleasing appearance of crisp, well-defined shapes, including very small shapes such as the small hearts shown in FIG. 2. The three-dimensional features also provide for softness during use, improved absorbency, less leakage, and overall improved in-use experience. But the necessary compression during folding, packaging, shipping and storing of the personal care articles can cause permanent loss of caliper of a topsheet, backsheet nonwovens, acquisition layers, distribution layers, or other component layers of the absorbent article thereby degrading the as-made functional benefits. We have found unexpectedly the nonwoven fabrics of the present disclosure retain to a significant degree their as made three-dimensional features even after undergoing compression packaging and distribution in a compression packaged state.

Table 1 below shows compression recovery data for two embodiments of the present disclosure. Example 1 corresponds to the fabric 10 shown in FIG. 1 and made on a forming belt as described with reference to FIGS. 12 and 14. Example 2 corresponds to the fabric 10 shown in FIG. 2 and made on a forming belt as described with reference to FIGS. 15 and 16. As can be seen from the data, the fabrics 10 of the invention show a significant benefit with respect to compression recovery when measured by the Compression Aging Test. In a form, packages of the absorbent articles having the compression recovery characteristics of the present disclosure can have a reduced in-bag stack height yet still deliver the aesthetic, absorbency, and softness benefits of the as made diaper; or as if it were never compression packaged. This invention provides for reduced in-bag stack height packages which allow caregivers to easily handle and store the packages while also providing manufacturers with reduced distribution costs, both achieved while maintaining as made aesthetics clarity, absorbency, or softness performance of the absorbent article.

Example 1

A bicomponent spunbond nonwoven fabric that was produced by spinning a 50:50 ratio of polyethylene sheath (Aspun-6850-A obtained from Dow chemical company) and polypropylene core (PH-835 obtained from LyondellBasell) in a trilobal fiber configuration, as shown in FIG. 6, which is a scanning electron micrograph showing a cross section of a bicomponent trilobal fiber. The nonwoven fabric was spun on a forming belt having a repeating pattern as described in FIG. 12 as described below with respect to FIGS. 7 and 8 moving at a linear speed of about 25 meters per minute to an average basis weight of 30 grams per square meter with a repeating pattern of heart shapes as shown in FIG. 1. Fibers of the fabric were further bonded on first side 12 by heated compaction rolls 70, 72 (described below) at 130° C., and being wound on to a reel at winder 75.

Example 2

A bicomponent spunbond nonwoven fabric was produced by spinning a 50:50 ratio of polyethylene sheath (Aspun-6850-A obtained from Dow chemical company) and polypropylene core (PH-835 obtained from LyondellBasell) in a trilobal fiber configuration, as shown in FIG. 6, which is a scanning electron micrograph showing a cross section of a bicomponent trilobal fiber. The nonwoven fabric was spun on a forming belt having a repeating pattern as described in FIG. 16 as described below with respect to FIGS. 7 and 8 moving at a linear speed of about 25 meters per minute to form a fabric 10 having an average basis weight of 30 grams per square meter with a repeating pattern of diamond shapes as shown in FIG. 2. Fibers of the fabric were further bonded on first side 12 by heated compaction rolls 70, 72 (described below) at 130° C.

meters/minute, and can be from about 2,000 to about 7,000 meters/minute, and can be from about 2,500 to about 5,000 meters/minute. Spinning speeds can affect the brittleness of the spun fiber, and, in general, the higher the spinning speed, the less brittle the fiber. Continuous fibers can be produced through spunbond methods or meltblowing processes.

A fabric of the present disclosure can include continuous multicomponent polymeric filaments comprising a primary polymeric component and a secondary polymeric component. The filaments can be continuous bicomponent filaments comprising a primary polymeric component A and an secondary polymeric component B. The bicomponent filaments have a cross-section, a length, and a peripheral surface. The components A and B can be arranged in substantially distinct zones across the cross-section of the bicomponent filaments and can extend continuously along the length of the bicomponent filaments. The secondary component B constitutes at least a portion of the peripheral surface of the bicomponent filaments continuously along the length of the bicomponent filaments. The polymeric components A and B can be melt spun into multicomponent fibers on conventional melt spinning equipment. The equipment will be chosen based on the desired configuration of the multicomponent. Commercially available melt spinning equipment is available from Hills, Inc. located in Melbourne, Florida. The temperature for spinning range from about 180° C. to about 230° C. The processing temperature is determined by the chemical nature, molecular weights and concentration of each component. The bicomponent spunbond filaments can have an average diameter from about 6 to about 40 microns, and preferably from about 12 to about 40 microns.

TABLE 1

| | | 4 KPa (~96 mm IBSH) | | 14 KPa (~84 mm IBSH) | | 35 KPa ~68 mm IBSH) | |
|---|---|---|---|---|---|---|---|
| 3-D Nonwoven | Fresh (Nonwoven off the roll) Caliper | Caliper after Compression | Percent Caliper Retention (%) | Caliper after Compression | Percent Caliper Retention (%) | Caliper after Compression | Percent Caliper Retention (%) |
| Example 1 | 0.45 | 0.38 | 84.44 | 0.35 | 77.78 | 0.34 | 75.56 |
| Example 2 | 0.43 | 0.36 | 83.72 | 0.36 | 83.72 | 0.31 | 72.09 |

Compression Recovery

As can be seen from Table 1, fabrics 10 of the invention retain significant amounts of caliper after compression at relatively high pressures. For example, the Example 1 and Example 2 samples retain greater than 70% of their original average caliper after being tested by the Compression Aging Test at a pressure of 35 KPa. The Compression Aging Test is a simulation of the conditions a nonwoven fabric would encounter if packaged in a high compression packaging of diapers and then remain in such a state during distribution to a consumer and then the package finally opened by a consumer.

The present disclosure can utilize the process of melt spinning. In melt spinning, there is no mass loss in the extrudate. Melt spinning is differentiated from other spinning, such as wet or dry spinning from solution, where a solvent is being eliminated by volatilizing or diffusing out of the extrudate resulting in a mass loss.

Spinning can occur at from about 150° C. to about 280°, or, in some embodiments, at from about 190° to about 230°. Fiber spinning speeds can be greater than 100 meters/minute, and can be from about 1,000 to about 10,000

The components A and B can be arranged in either a side-by-side arrangement as shown in FIG. 5A or an eccentric sheath/core arrangement as shown in FIG. 5B to obtain filaments which exhibit a natural helical crimp. Alternatively, the components A and B can be arranged in a concentric sheath core arrangement as shown in FIG. 5C. Additionally, the component A and B can be arranged in multi-lobal sheath core arrangement as shown in FIG. 6. Other multicomponent fibers can be produced by using the compositions and methods of the present disclosure. The bicomponent and multicomponent fibers may be segmented pie, ribbon, islands-in-the-sea configuration, or any combination thereof. The sheath may be continuous or non-continuous around the core. The ratio of the weight of the sheath to the core is from about 5:95 to about 95:5. The fibers of the present disclosure may have different geometries that include round, elliptical, star shaped, rectangular, and other various eccentricities.

Methods for extruding multicomponent polymeric filaments into such arrangements are well-known to those of ordinary skill in the art.

A wide variety of polymers are suitable to practice the present disclosure including polyolefins (such as polyethylene, polypropylene and polybutylene), polyesters, polyamides, polyurethanes, elastomeric materials and the like. Non-limiting examples of polymer materials that can be spun into filaments include natural polymers, such as starch, starch derivatives, cellulose and cellulose derivatives, hemicellulose, hemicelluloses derivatives, chitin, chitosan, polyisoprene (cis and trans), peptides, polyhydroxyalkanoates, and synthetic polymers including, but not limited to, thermoplastic polymers, such as polyesters, nylons, polyolefins such as polypropylene, polyethylene, polyvinyl alcohol and polyvinyl alcohol derivatives, sodium polyacrylate (absorbent gel material), and copolymers of polyolefins such as polyethylene-octene or polymers comprising monomeric blends of propylene and ethylene, and biodegradable or compostable thermoplastic polymers such as polylactic acid filaments, polyvinyl alcohol, filaments, and polycaprolactone filaments. In one example, thermoplastic polymer selected from the group consisting of: polypropylene, polyethylene, polyester, polylactic acid, polyhydroxyalkanoate, polyvinyl alcohol, polycaprolactone, styrene-butadiene-styrene block copolymer, styrene-isoprene-styrene block copolymer, polyurethane, and mixtures thereof. In another example, the thermoplastic polymer is selected from the group consisting of: polypropylene, polyethylene, polyester, polylactic acid, polyhydroxyalkanoate, polyvinyl alcohol, polycaprolactone, and mixtures thereof. Alternatively, the polymer can comprise one derived from monomers which are biobased such as bio-polyethylene or bio-polypropylene.

Primary component A and secondary component B can be selected so that the resulting bicomponent filament is providing improved nonwoven bonding and substrate softness. Primary polymer component A has melting temperature which is lower than the melting temperature of secondary polymer component B.

Primary polymer component A can comprise polyethylene or random copolymer of propylene and ethylene. Secondary polymer component B can comprise polypropylene or random copolymer of propylene and ethylene. Polyethylenes include linear low density polyethylene and high density polyethylene. In addition, secondary polymer component B may comprise additives for enhancing the natural helical crimp of the filaments, lowering the bonding temperature of the filaments, and enhancing the abrasion resistance, strength and softness of the resulting fabric.

Inorganic fillers such as the oxides of magnesium, aluminum, silicon, and titanium may be added as inexpensive fillers or processing aides. Other inorganic materials include hydrous magnesium silicate, titanium dioxide, calcium carbonate, clay, chalk, boron nitride, limestone, diatomaceous earth, mica glass quartz, and ceramics.

The filaments of the present invention also contain a slip additive in an amount sufficient to impart the desired haptics to the fiber. As used herein "slip additive" or "slip agent" means an external lubricant. The slip agent when melt-blended with the resin gradually exudes or migrates to the surface during cooling or after fabrication, hence forming a uniform, invisibly thin coating thereby yielding permanent lubricating effects. The slip agent is preferably a fast bloom slip agent, and can be a hydrocarbon having one or more functional groups selected from hydroxide, aryls and substituted aryls, halogens, alkoxys, carboxylates, esters, carbon unsaturation, acrylates, oxygen, nitrogen, carboxyl, sulfate and phosphate.

During the making or in a post-treatment or even in both, the three dimensional nonwovens of the present invention can be treated with surfactants or other agents to either hydrophilize the web or make it hydrophobic. This is standard practice for nonwovens used in absorbent articles. For example, a web used for a topsheet may be treated with a hydrophilizing material or surfactant so as to make it permeable to body exudates such as urine. For other absorbent articles, the topsheet may remain at its naturally hydrophobic state or made even more hydrophobic through the addition of a hydrophobizing material or surfactant.

Suitable materials for preparing the multicomponent filaments of the fabric of the present disclosure include PH-835 polypropylene obtained from LyondellBasell and Aspun-6850-A polyethylene obtained from Dow chemical company.

When polyethylene is component A (sheath) and polypropylene is component B (core), the bicomponent filaments may comprise from about 5 to about 95% by weight polyethylene and from about 95 to about 5% polypropylene. The filaments can comprise from about 40 to about 60% by weight polyethylene and from about 60 to about 40% by weight polypropylene.

Figure 7:
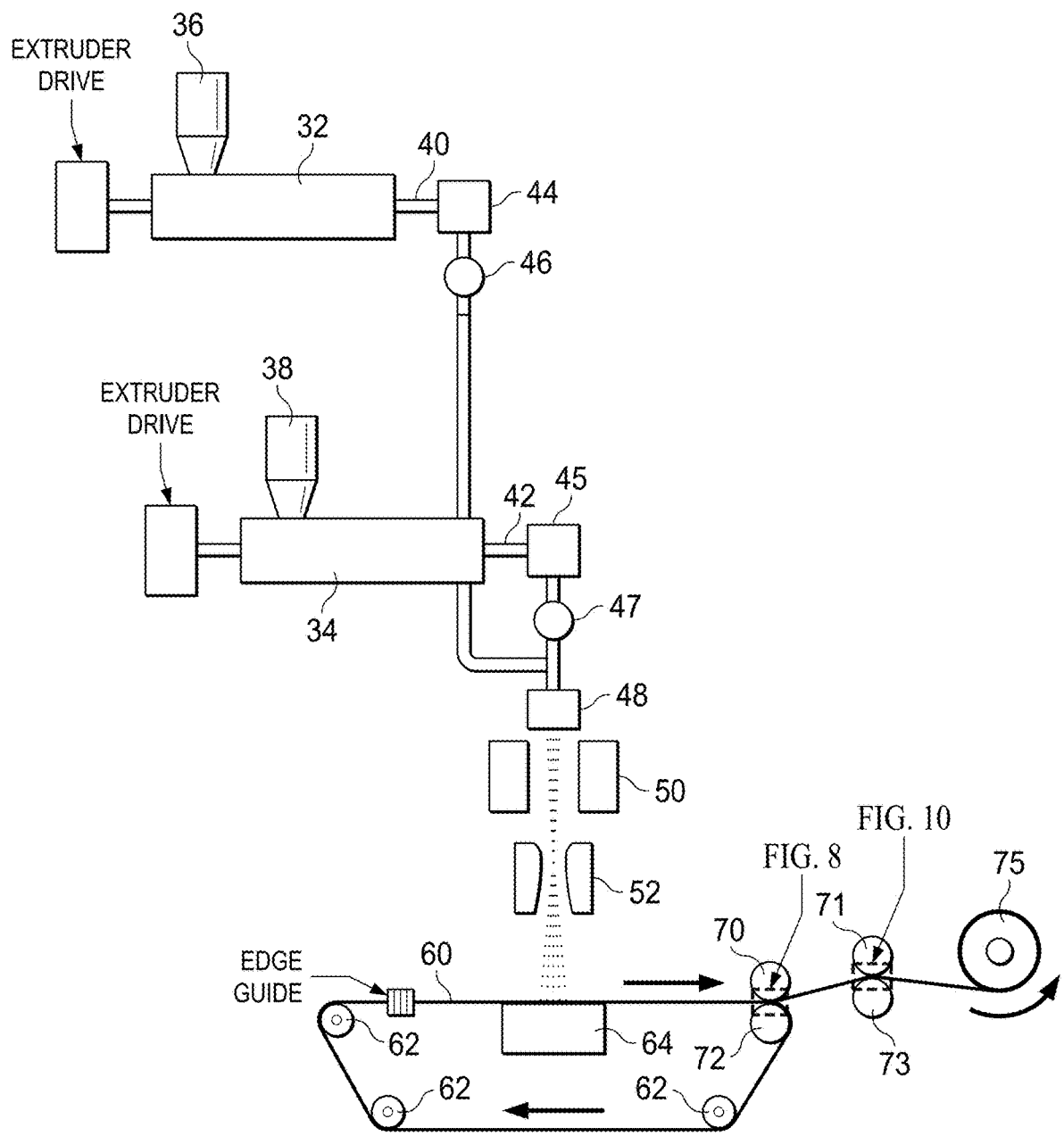
FIG. 7 is a schematic representation of an apparatus for making a fabric of the present disclosure.

Turning to FIG. 7, a representative process line 30 for preparing fabrics 10 of the present disclosure is disclosed. The process line 30 is arranged to produce a fabric of bicomponent continuous filaments, but it should be understood that the present disclosure comprehends nonwoven fabrics made with monocomponent or multicomponent filaments having more than two components. Bicomponent filaments may be trilobal.

The process line 30 includes a pair of extruders 32 and 34 for separately extruding the primary polymer component A and the secondary polymer component B. Polymer component A is fed into the respective extruder 32 from a first hopper 36 and polymer component B is fed into the respective extruder 34 from a second hopper 38. Polymer components A and B can be fed from the extruders 32 and 34 through respective polymer conduits 40 and 42 to filters 44 and 45 and melt pumps 46 and 47, which pump the polymer into a spin pack 48. Spinnerets for extruding bicomponent filaments are well-known to those of ordinary skill in the art and thus are not described here in detail.

Generally described, the spin pack 48 includes a housing which includes a plurality of plates stacked one on top of the other with a pattern of openings arranged to create flow paths for directing polymer components A and B separately through the spinneret. The spin pack 48 has openings arranged in one or more rows. The spinneret openings form a downwardly extending curtain of filaments when the polymers are extruded through the spinneret. For the purposes of the present disclosure, spinnerets may be arranged to form sheath/core or side-by-side bicomponent filaments illustrated in FIGS. 5A, 5B, and 5C, as well as non-round fibers, such as tri-lobal fibers as shown in FIG. 6. Moreover, the fibers may be monocomponent comprising one polymeric component such as polypropylene.

The process line 30 also includes a quench blower 50 positioned adjacent the curtain of filaments extending from the spinneret. Air from the quench air blower 50 quenches the filaments extending from the spinneret. The quench air can be directed from one side of the filament curtain or both sides of the filament curtain.

An attenuator 52 is positioned below the spinneret and receives the quenched filaments. Fiber draw units or aspirators for use as attenuators in melt spinning polymers are well-known. Suitable fiber draw units for use in the process of the present disclosure include a linear fiber attenuator of the type shown in U.S. Pat. No. 3,802,817 and eductive guns of the type shown in U.S. Pat. No. 3,692,618 and U.S. Pat. No. 3,423,266, the disclosures of which are incorporated herein by reference.

Generally described, the attenuator 52 includes an elongate vertical passage through which the filaments are drawn by aspirating air entering from the sides of the passage and flowing downwardly through the passage. A shaped, endless, at least partially foraminous, forming belt 60 is positioned below the attenuator 52 and receives the continuous filaments from the outlet opening of the attenuator 52. The forming belt 60 is a belt and travels around guide rollers 62. A vacuum 64 positioned below the forming belt 60 where the filaments are deposited draws the filaments against the forming surface. Although the forming belt 60 is shown as a belt in FIG. 8, it should be understood that the forming belt can also be in other forms such as a drum. Details of particular shaped forming belts are explained below.

In operation of the process line 30, the hoppers 36 and 38 are filled with the respective polymer components A and B. Polymer components A and B are melted and extruded by the respective extruders 32 and 34 through polymer conduits 40 and 42 and the spin pack 48. Although the temperatures of the molten polymers vary depending on the polymers used, when polyethylene and polypropylene are used as primary component A and secondary component B respectively, the temperatures of the polymers can range from about 190° C. to about 240° C.

As the extruded filaments extend below the spinneret, a stream of air from the quench blower 50 at least partially quenches the filaments, and, for certain filaments, to induce crystallization of molten filaments. The quench air can flow in a direction substantially perpendicular to the length of the filaments at a temperature of about 0° C. to about 35° C. and a velocity from about 100 to about 400 feet per minute. The filaments can be quenched sufficiently before being collected on the forming belt 60 so that the filaments can be arranged by the forced air passing through the filaments and forming surface. Quenching the filaments reduces the tackiness of the filaments so that the filaments do not adhere to one another too tightly before being bonded and can be moved or arranged on the forming belt during collection of the filaments on the forming belt and formation of the web.

After quenching, the filaments are drawn into the vertical passage of the attenuator 52 by a flow of the fiber draw unit. The attenuator is can be positioned 30 to 60 inches below the bottom of the spinneret.

The filaments can be deposited through the outlet opening of the attenuator 52 onto the shaped, traveling forming belt 60. As the filaments are contacting the forming surface of the forming belt 60, the vacuum 64 draws the air and filaments against the forming belt 60 to form a nonwoven web of continuous filaments which assumes a shape corresponding to the shape of the forming surface. As discussed above, because the filaments are quenched, the filaments are not too tacky and the vacuum can move or arrange the filaments on the forming belt 60 as the filaments are being collected on the forming belt 60 and formed into the fabric 10.

The process line 30 further includes one or more bonding devices such as the cylinder-shaped compaction rolls 70 and 72, which form a nip through which the fabric can be compacted, i.e., calendared, and which can be heated to bond fibers as well. One or both of compaction rolls 70, 72 can be heated to provide enhanced properties and benefits to the fabric 10 by bonding portions of the fabric. For example, it is believed that heating sufficient to provide thermal bonding improves the fabric's 10 tensile properties. The compaction rolls may be pair of smooth surface stainless steel rolls with independent heating controllers. The compaction rolls may be heated by electric elements or hot oil circulation. The gap between the compaction rolls can be hydraulically controlled to impose desired pressure on the fabric as it passes through the compaction rolls on the forming belt. In an embodiment, with a forming belt caliper of 1.4 mm, and a spunbond nonwoven having a basis weight of 30 gsm, the nip gap between the compaction rolls 70 and 72 can be about 1.4 mm.

Figure 8:
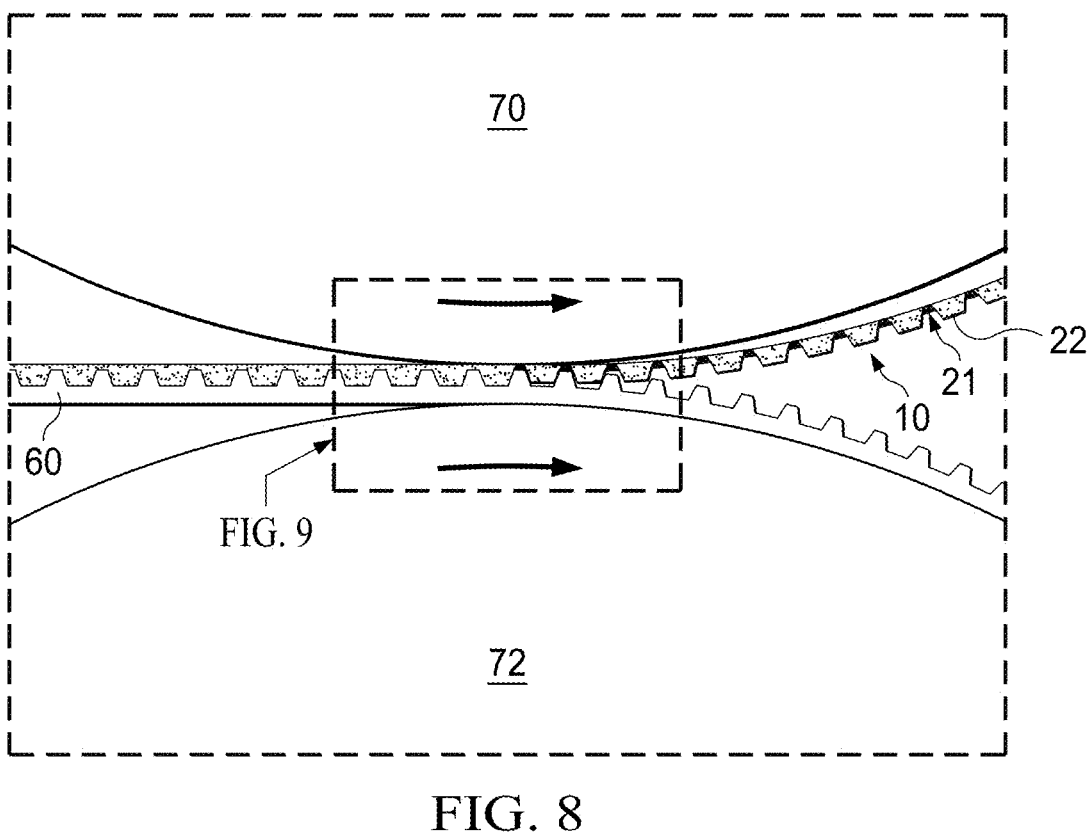
FIG. 8 is a detail of a portion of the apparatus for bonding a portion of a fabric of the present disclosure.
Figure 9:
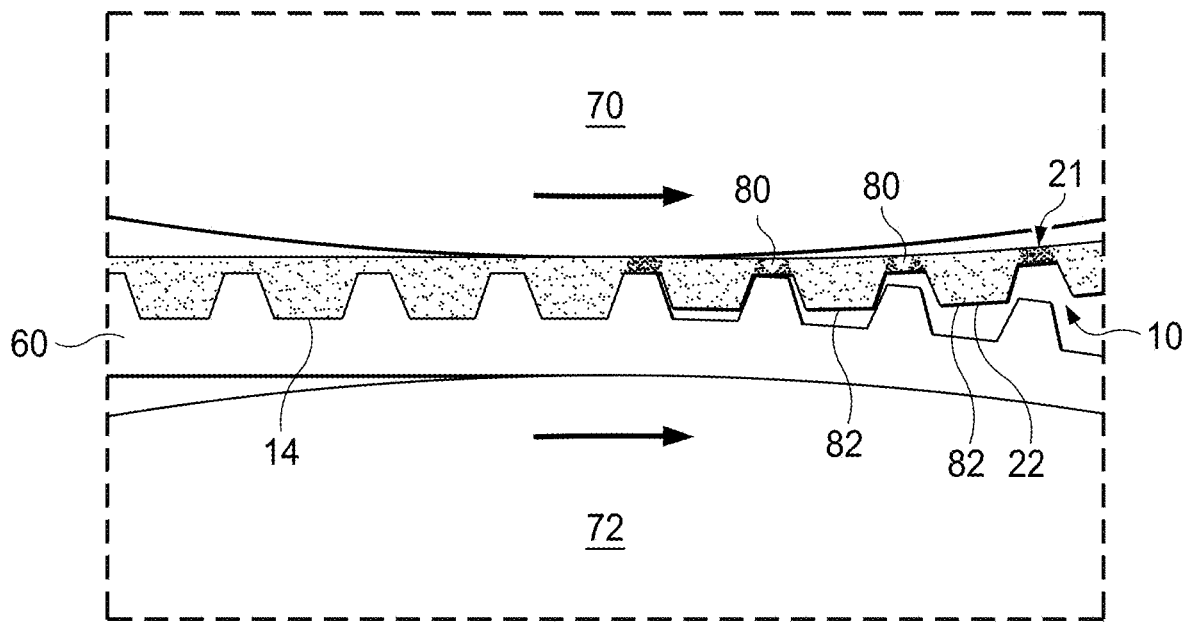
FIG. 9 is a further detail of a portion of the apparatus for bonding a portion of a fabric of the present disclosure.
Figure 11:
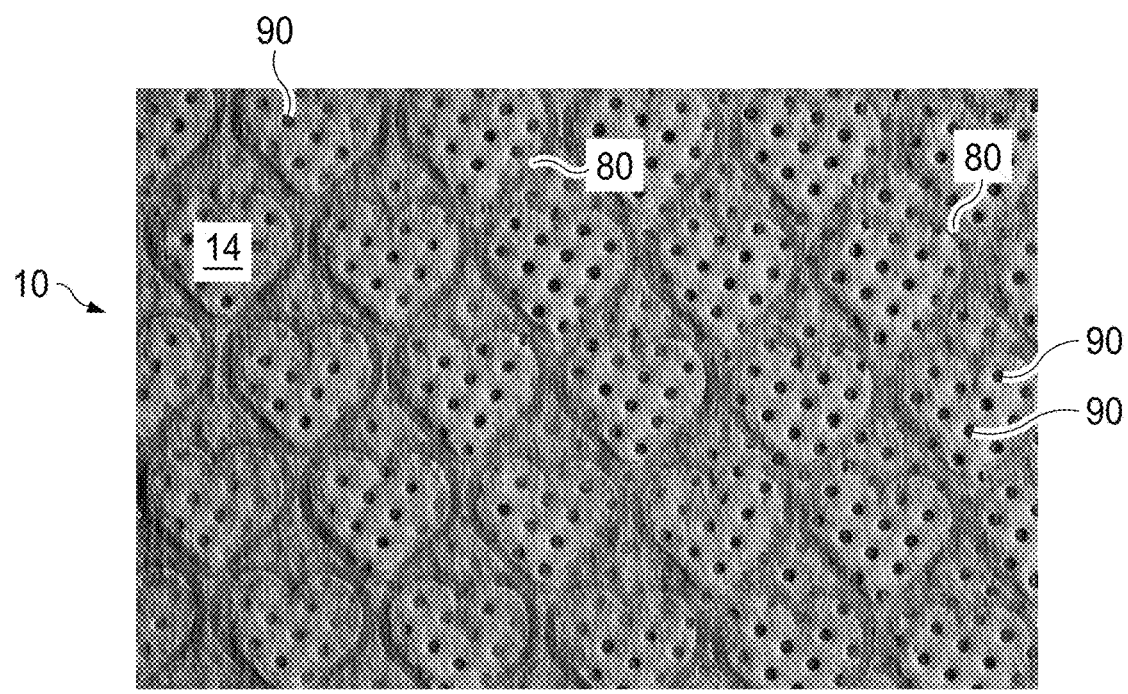
FIG. 11 is a photograph of an embodiment of the present disclosure.

In an embodiment, upper compaction roll 70 can be heated sufficient to melt bond fibers on the first surface 12 of the fabric 10, to impart strength to the fabric so that it can be removed from forming belt 60 without losing integrity. As shown in FIGS. 8 and 9, for example, as rolls 70 and 72 rotate in the direction indicated by the arrows, belt 60 with the spunbond fabric laid down on it enter the nip formed by rolls 70 and 72. Heated roll 70 can heat the portions of fabric 10 that are pressed against it by the raised resin elements of belt 60, i.e., in regions 21, to create bonded fibers 80 on at least first surface 12 of fabric 10. As can be understood by the description herein, the bonded regions so formed can take the pattern of the raised elements of forming belt 60. For example, the bonded areas so formed can be a substantially continuous network or a substantially semi-continuous network on first surface 12 of regions 21 that make the same pattern as the hearts of FIG. 1 and FIG. 11. By adjusting temperature and dwell time, the bonding can be limited primarily to fibers closest to first surface 12, or thermal bonding can be achieved to second surface 14 as shown in FIG. 11 (which also shows point bonds 90, discussed more fully below). Bonding can also be a discontinuous network, for example, as point bonds 90, discussed below.

The raised elements of the forming belt 60 may be selected to establish various network characteristics of the forming belt and the bonded regions of the nonwoven substrate 11 or nonwoven fabric 10. The network corresponds to the resin making up the raised elements of the forming belt 60 and may comprise substantially continuous, substantially semi-continuous, discontinuous, or combinations thereof options. These networks may be descriptive of the raised elements of the forming belt 60 as it pertains to their appearance or make-up in the X-Y planes of the forming belt 60 or the three dimensional features comprising the nonwoven substrate 11 or nonwoven fabric 10 of the present invention.

"Substantially continuous" network refers to an area within which one can connect any two points by an uninterrupted line running entirely within that area throughout the line's length. That is, the substantially continuous network has a substantial "continuity" in all directions parallel to the first plane and is terminated only at edges of that region. The term "substantially," in conjunction with continuous, is intended to indicate that while an absolute continuity can be achieved, minor deviations from the absolute continuity may be tolerable as long as those deviations do not appreciably affect the performance of the fibrous structure (or a molding member) as designed and intended.

"Substantially semi-continuous" network refers an area which has "continuity" in all, but at least one, directions parallel to the first plane, and in which area one cannot connect any two points by an uninterrupted line running entirely within that area throughout the line's length. The semi-continuous framework may have continuity only in one direction parallel to the first plane. By analogy with the continuous region, described above, while an absolute continuity in all, but at least one, directions is preferred, minor deviations from such a continuity may be tolerable as long as those deviations do not appreciably affect the performance of the fibrous structure.

"Discontinuous" network refer to discrete, and separated from one another areas that are discontinuous in all directions parallel to the first plane.

Figure 10:
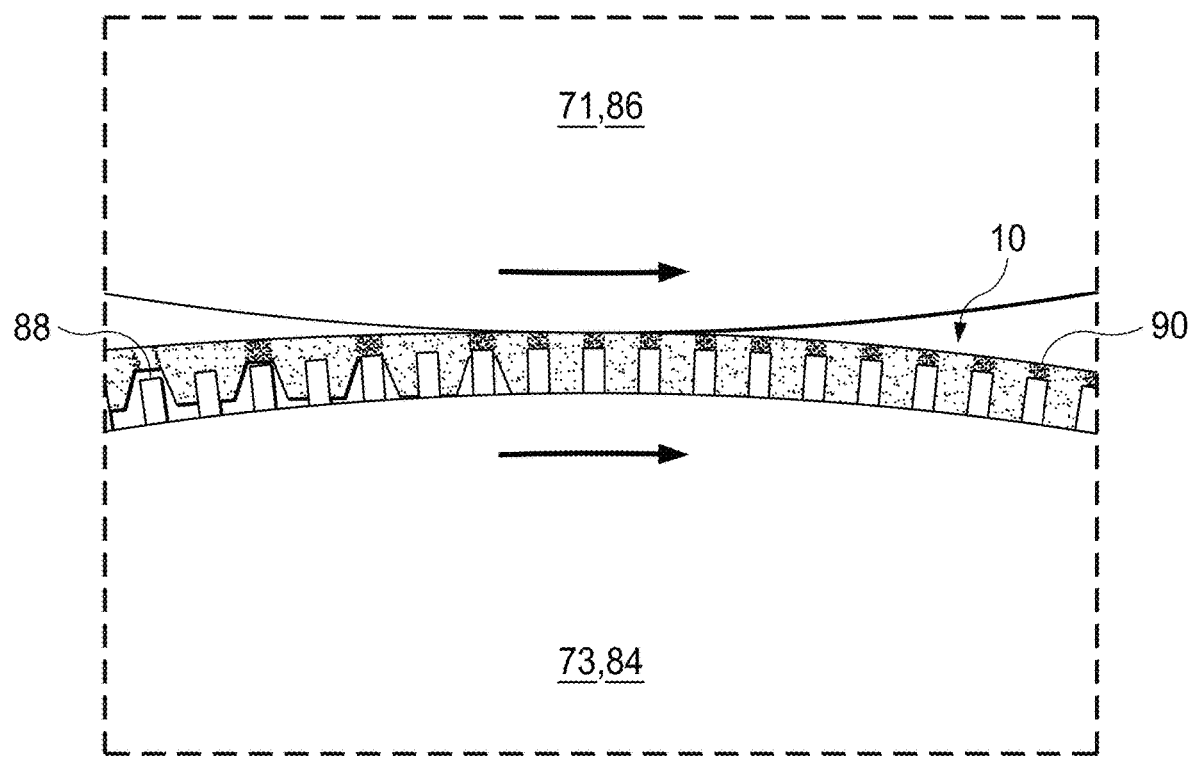
FIG. 10 is a detail of a portion of the apparatus for optional additional bonding of a portion of a fabric of the present disclosure.

After compaction, the fabric can leave the forming belt 60 and be calendared through a nip formed by calendar rolls 71, 73, after which the fabric can be wound onto a reel. As shown in the schematic cross section of FIG. 10, the calendar rolls can be stainless steel rolls having an engraved pattern roll 84 and a smooth roll 86. The engraved roll can have raised portions 88 that can provide for additional compaction and bonding to the fabric 10. Raised portions 88 can be a regular pattern of relatively small spaced apart "pins" that form a pattern of relatively small point bonds 90 in the nip of calendar rolls 71 and 73. The percent of point bonds in the fabric 10 can be from 3% to 30% or from 7% to 20%. The engraved pattern can be a plurality of closely spaced, regular, generally cylindrically-shaped, generally flat-topped pin shapes, with pin heights being in a range from ranging 0.5 mm to 5 mm and preferably from 1 mm to 3 mm. Pin bonding calendar rolls can form closely spaced, regular point bonds 90 in fabric 10, as shown in FIG. 11. Further bonding can be by hot-air through bonding, for example.

As shown in FIG. 11, in an embodiment, heated compaction roll 70 can form a bond pattern, which can be a substantially continuous network bond pattern 80 (e.g., interconnected heart shaped bonds) on first surface 12 of fabric 10 (not shown in FIG. 11, as it faces away from the viewer), and engraved calendar roll 73 can form relatively small point bonds 90 on second surface 14 of fabric 10. The point bonds 90 secure loose fibers that would otherwise be prone to fuzzing or pilling during use of the fabric 10. The advantage of the resulting structure of fabric 10 is most evident when used as a topsheet in a personal care article such as a diaper or sanitary napkin. In use in a personal care article, the first surface 12 of fabric 10 can be relatively flat (relative to second surface 14) and have a relatively large amount of bonding due to the heated compaction roll forming bonds 80 at the areas of the fabric pressed by the raised elements of forming belt 60. This bonding gives the fabric 10 structural integrity, but can be relatively stiff or rough to the skin of a user. Therefore, the first surface 12 of the fabric 10 can be oriented in a diaper or sanitary napkin to face the interior of the article, i.e., away from the body of the wearer. Likewise, the second surface 14 can be body facing in use, and in contact with the body. The relatively small point bonds 90 are less likely to be perceived visually or tactiley by the user, and the relatively soft three-dimensional features remain visually free of fuzzing and pilling while feeling soft to the body in use. Further bonding can be used instead of, or in addition to, the above mentioned bonding.

Forming belt 60 can be made according to the methods and processes described in U.S. Pat. No. 6,610,173, issued to Lindsay et al. on Aug. 26, 2003, or U.S. Pat. No. 5,514,523 issued to Trokhan et al. on May 7, 1996, or U.S. Pat. No. 6,398,910 issued to Burazin et al. on Jun. 4, 2002, or US Pub. No. 2013/0199741, published in the name of Stage et al. on Aug. 8, 2013, each with the improved features and patterns disclosed herein for making spunbond nonwoven webs. The Lindsay, Trokhan, Burazin and Stage disclosures describe belts that are representative of papermaking belts made with cured resin on a woven reinforcing member, which belts, with improvements, can be utilized in the present disclosure as described herein.

Forming belt 60 having improved three-dimensional features and patterns for making spunbond nonwoven webs can also be made by the following methods and processes and/or on the following apparatuses, including with modifications as desired for structures taught herein: rotary screen processes as taught in U.S. Pat. No. 7,799,382 issued to Payne et al. on Sep. 21, 2010; polymer extrusion as taught in US 2007-0170610 by Payne et al., published July 26, or US 20072005-028018 by Sayers et al., published Dec. 22, 2005; resin system grafting as taught in U.S. Pat. No. 7,105,465 issued to Patel et al. on Sep. 12, 2006; perforated film as taught in U.S. Pat. No. 8,815,057 issued to Eberhardt et al. on Aug. 26, 2014; successive layer treatment as taught in US 2006-0019567 by Sayers, published Jan. 26, 2006; polymeric droplet deposition as taught in U.S. Pat. No. 7,005,044 issued to Kramer et al. on Feb. 28, 2006; polymeric droplet deposition with a sacrificial material as taught in U.S. Pat. No. 7,014,735 issued to Kramer et al. on Mar. 21, 2006; air permeable film technology as taught by U.S. Pat. No. 8,454,800 issued to Mourad et al. on Jun. 4, 2013 or U.S. Pat. No. 8,822,009 issued to Riviere et al. on Sep. 9, 2014; multilayer belt structures as taught in US 2016-0090692 by Eagles et al., published Mar. 31, 2016; laser etching as taught by U.S. Pat. No. 8,758,569 issued to Aberg et al. on Jun. 24, 2014 or U.S. Pat. No. 8,366,878 issued to Klerelid et al. on Feb. 5, 2013; extruded mesh technology as taught in US 2014-0272269 by Hansen, published Sep. 18, 2014; nonwoven belts as described in US 2008-0199655 by Monnerie et al., published Aug. 21, 2008; and additive manufacturing methods and processes as taught in US 2015-0102526A1 by Ward et al., published Apr. 16, 2015, or US 2016-0159007 by Miller et al., published Jun. 9, 2016, or WO 2016-085704 by Burazin et al., published Nov. 17, 2016, or US 2016-0185041 by Lisagor et al., published Jun. 30, 2016.

Figure 12:
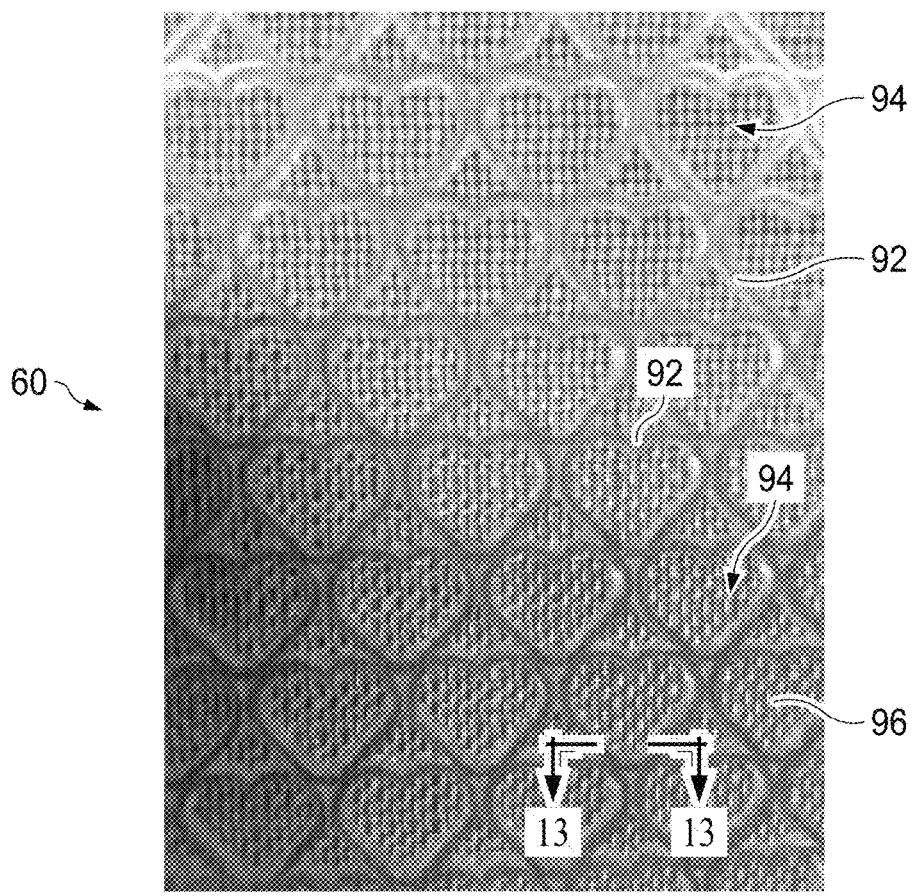
FIG. 12 is a photograph of a portion of a forming belt useful for the present disclosure.

An example of a forming belt 60 of the type useful in the present disclosure and which can be made according to the disclosure of U.S. Pat. No. 5,514,523, is shown in FIG. 12. As taught therein, a reinforcing member 94 (such as a woven belt of filaments 96) is thoroughly coated with a liquid photosensitive polymeric resin to a preselected thickness. A film or negative mask incorporating the desired raised element pattern repeating elements (e.g., FIG. 14) is juxtaposed on the liquid photosensitive resin. The resin is then exposed to light of an appropriate wave length through the film, such as UV light for a UV-curable resin. This exposure to light causes curing of the resin in the exposed areas (i.e., white portions or non-printed portions in the mask). Uncured resin (resin under the opaque portions in the mask) is removed from the system leaving behind the cured resin forming the pattern illustrated, for example, the cured resin elements 92 shown in FIG. 12. Other patterns can also be formed, as discussed herein.

Figure 13:
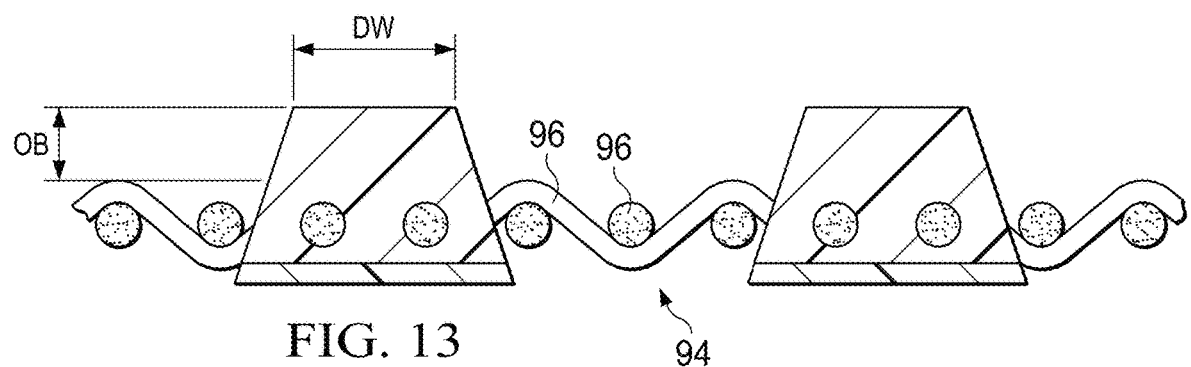
FIG. 13 is a cross-sectional depiction of a portion of the forming belt shown in FIG. 12.
Figure 14:
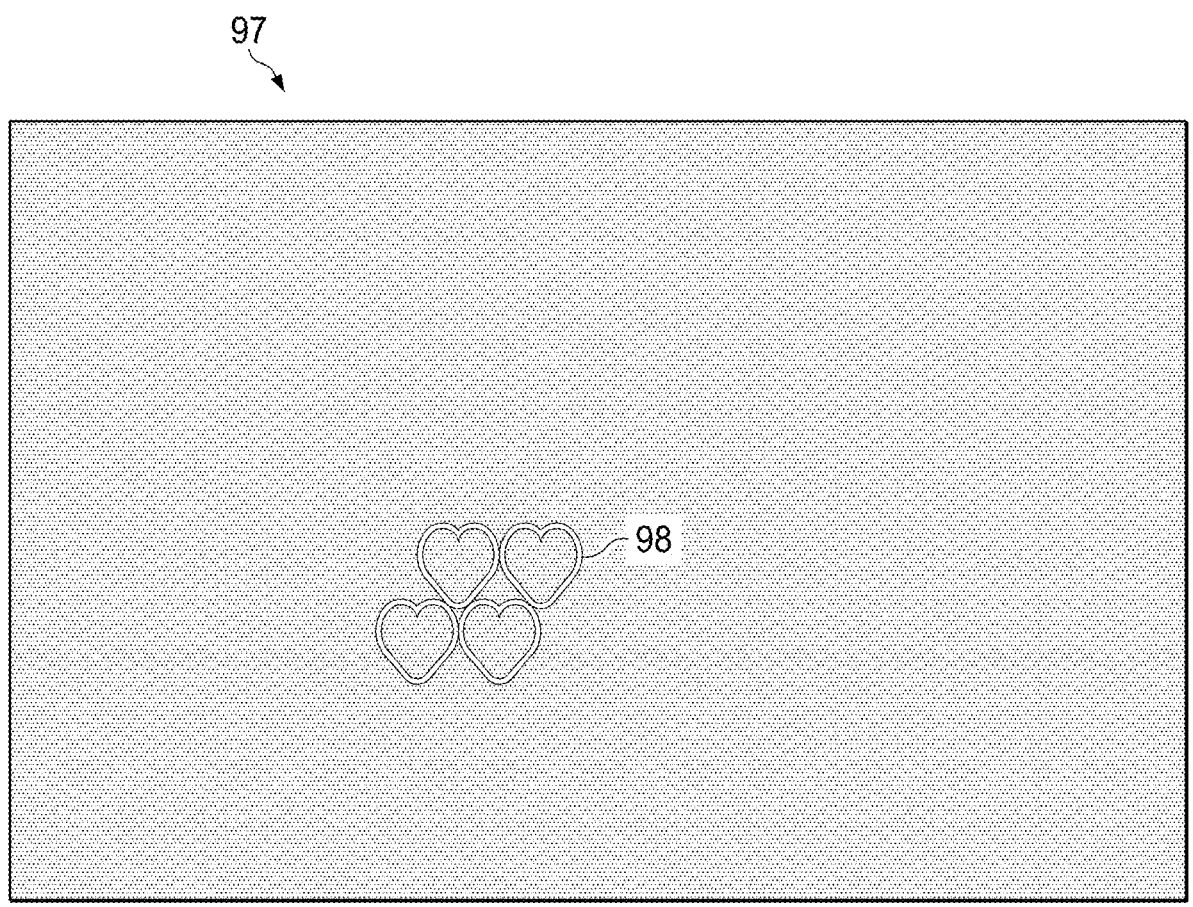
FIG. 14 is an image of a portion of a mask utilized to make the forming belt shown in FIG. 12.

FIG. 12 shows a portion of a forming belt 60 useful for making the fabric 10 shown in FIG. 1. As shown, the forming belt 60 can include cured resin elements 92 on a woven reinforcing member 94. The reinforcing member 94 can be made of woven filaments 96 as is known in the art of papermaking belts, including resin coated papermaking belts. The cured resin elements can have the general structure depicted in FIG. 12, and are made by the use of a mask 97 having the dimensions indicated in FIG. 14. As shown in schematic cross-section in FIG. 13, cured resin elements 92 flow around and are cured to "lock on" to reinforcing member 94 and can have a width at a distal end DW of about 0.020 inch to about 0.060 inch, or from about 0.025 inch to about 0.030 inch, and a total height above the reinforcing member 94, referred to as over burden, OB, of about 0.030 inch to about 0.120 inch or about 0.50 to about 0.80 inch, or about 0.060 inch. FIG. 14 represents a portion of a mask 97 showing the design and representative dimensions for one repeat unit of the repeating hearts design in the fabric 10 shown in FIG. 1. The white portion 98 is transparent to UV light, and in the process of making the belt, as described in U.S. Pat. No. 5,514,523, permits UV light to cure an underlying layer of resin which is cured to form the raised elements 92 on the reinforcing member 94. After the uncured resin is washed away, the forming belt 60 having a cured resin design as shown in FIG. 12 is produced by seaming the ends of a length of the belt, the length of which can be determined by the design of the apparatus, as depicted in FIG. 7.

Figure 15:
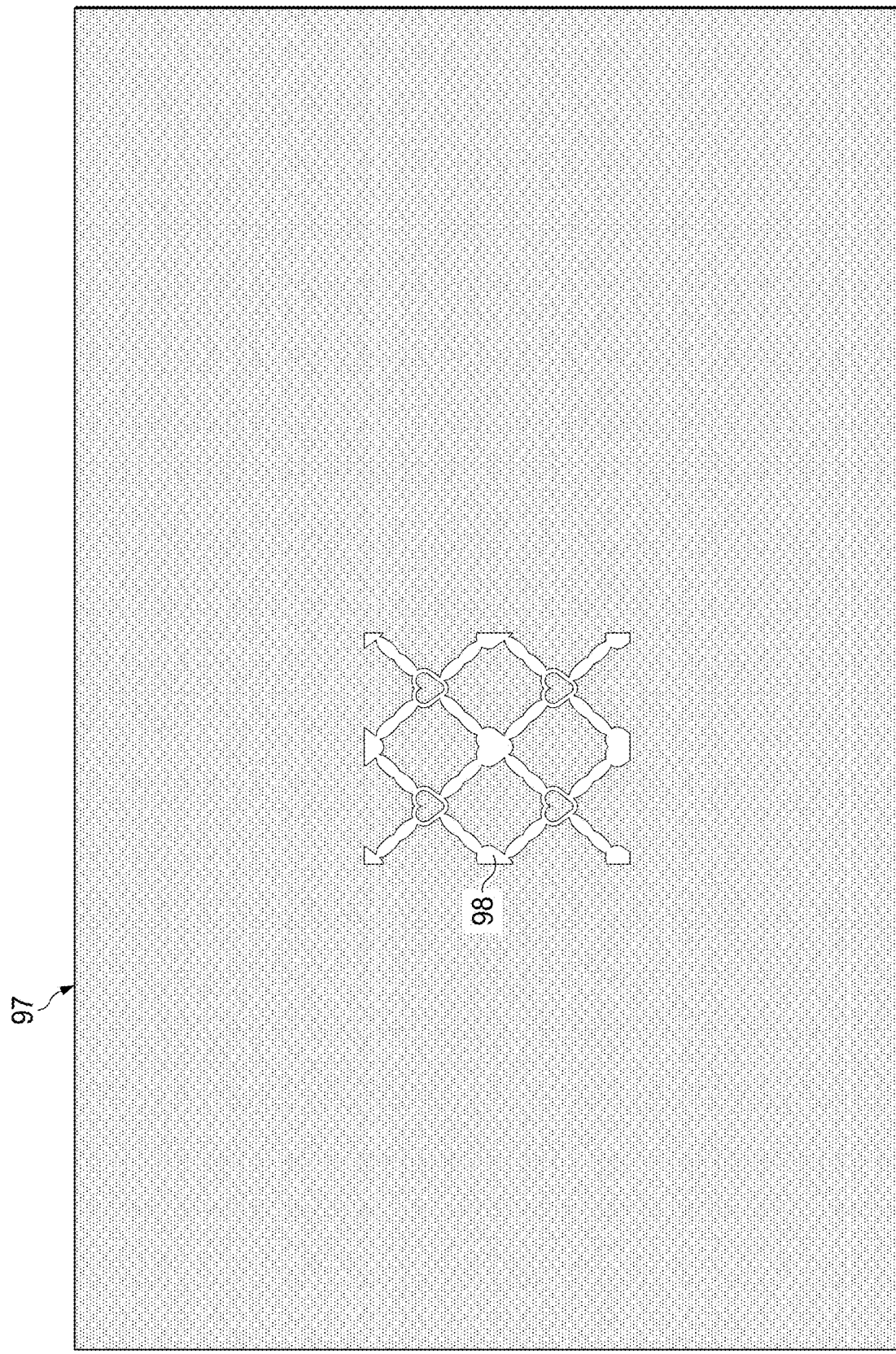
FIG. 15 is an image of a portion of a mask utilized to make the forming belt shown in FIG. 16.
Figure 16:
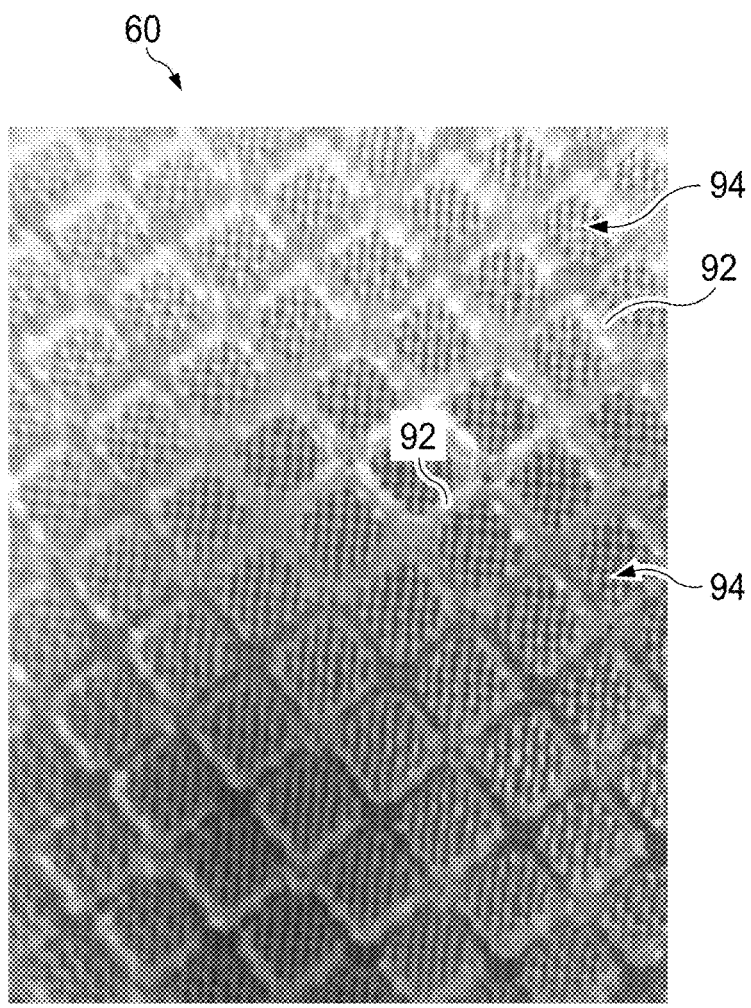
FIG. 16 is a photograph of a portion of a forming belt useful for the present disclosure.

In like manner, FIG. 15 represents a portion of a mask 97 showing the design for one repeat unit of the repeating design in the fabric 10 shown in FIG. 2. The white portion 98 is transparent to UV light, and in the process of making the belt permits UV light to cure an underlying layer of resin which is cured to the reinforcing member 94. After the uncured resin is washed away, the forming belt 60 having a cured resin design as shown in FIG. 16 is produced by seaming the ends of a length of the belt, the length of which can be determined by the design of the apparatus, as depicted in FIG. 7.

Figure 17:
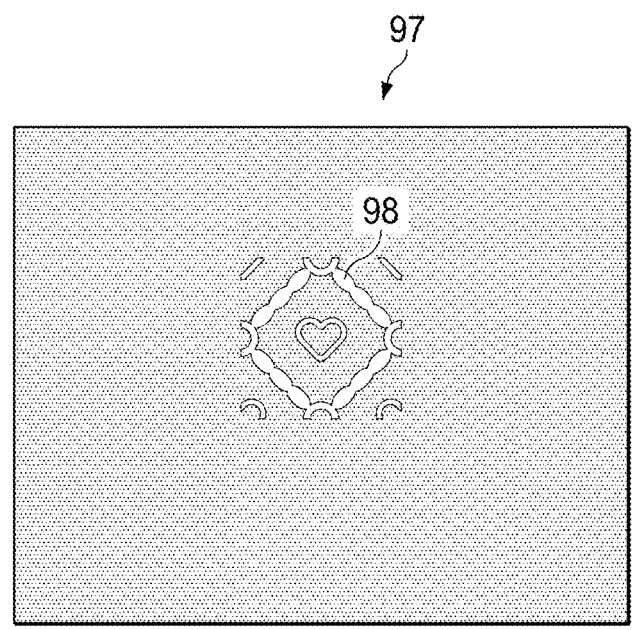
FIG. 17 is an image of a portion of a mask utilized to make the forming belt shown in FIG. 18.
Figure 18:
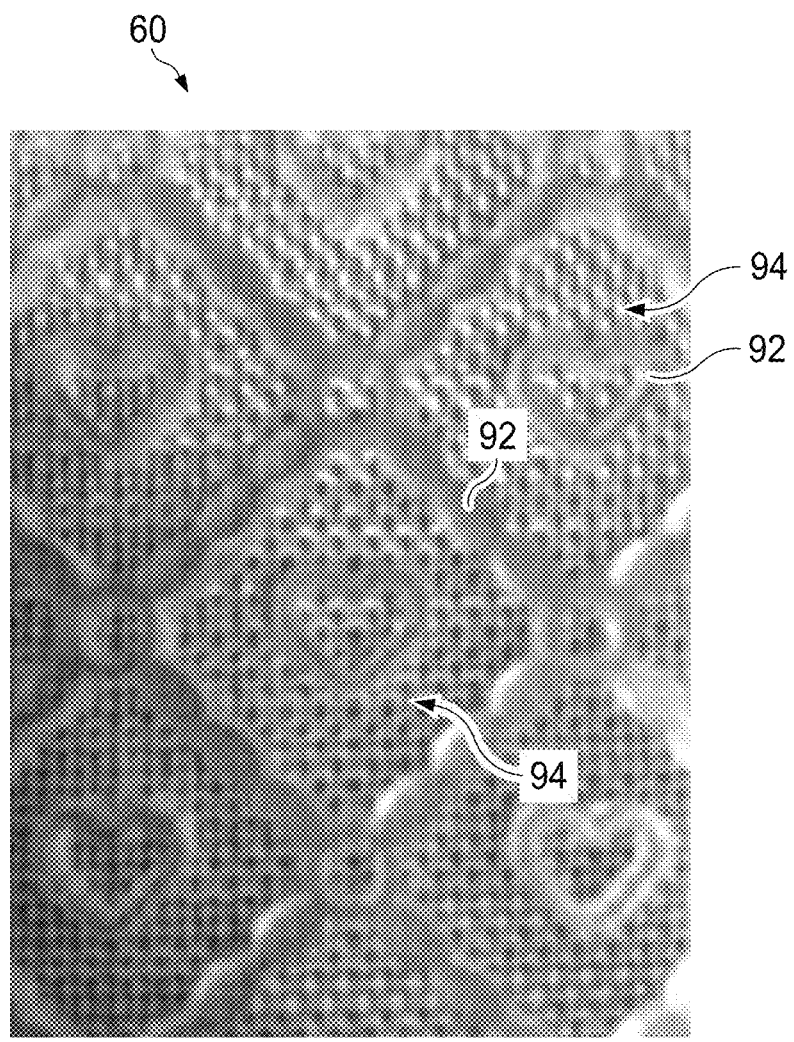
FIG. 18 is a photograph of a portion of a forming belt useful for the present disclosure.

Further, in another non-limiting example, FIG. 17 represents a portion of a mask showing the design for one repeat unit of the repeating design in the fabric 10 shown in FIG. 18. The white portion 98 is transparent to UV light, and in the process of making the belt permits UV light to cure an underlying layer of resin which is cured to the reinforcing member 94. After the uncured resin is washed away, the forming belt 60 having a cured resin design as shown in FIG. 18 is produced by seaming the ends of a length of fabric 10.

Figure 19:
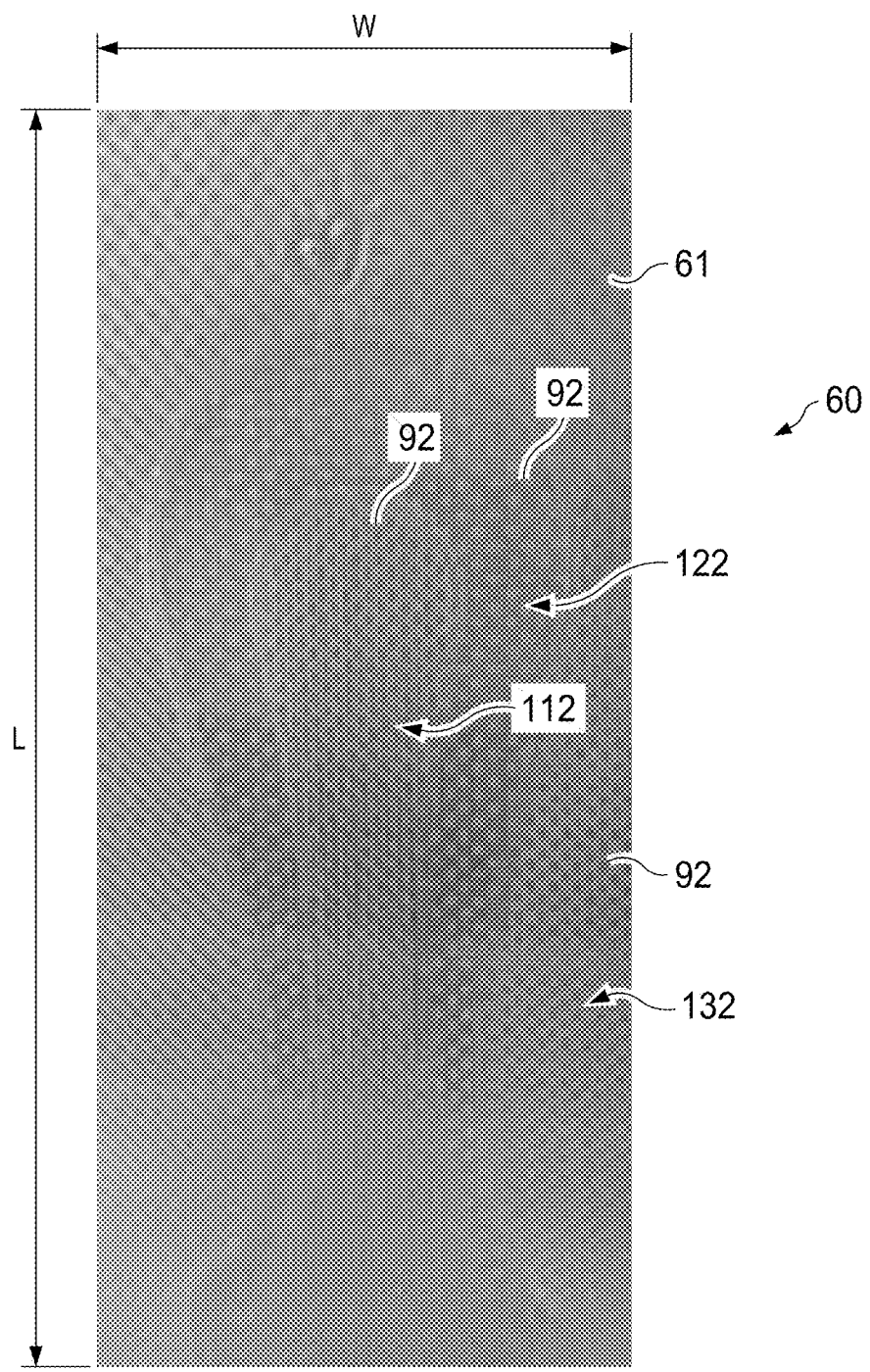
FIG. 19 is a photograph of a portion of a forming belt useful for the present disclosure.
Figure 20:
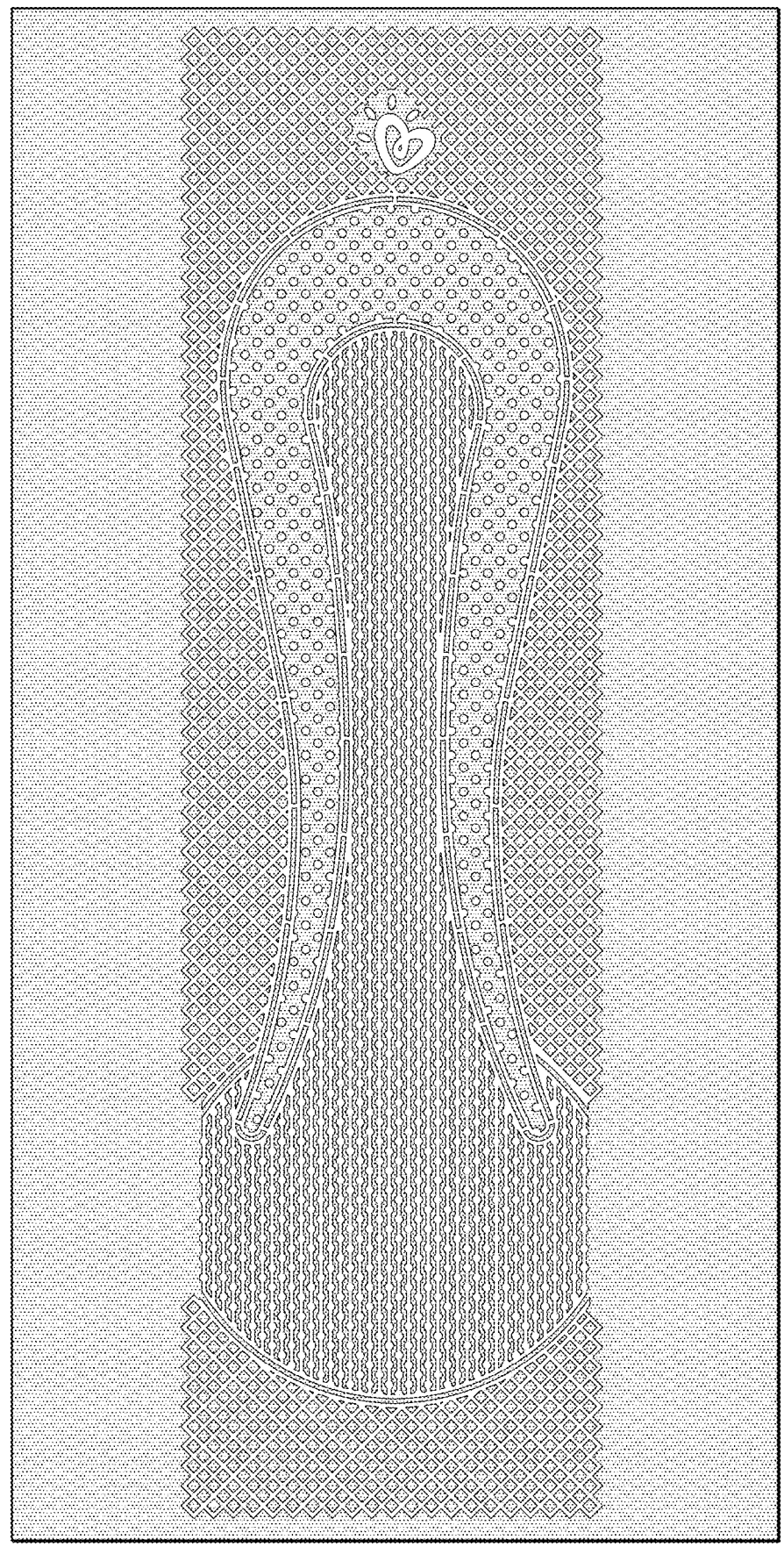
FIG. 20 an image of a mask utilized to make the forming belt shown in FIG. 19.

Another example of a portion of a forming belt 60 of the type useful in the present disclosure is shown in FIG. 19. The portion of the forming belt 60 shown in FIG. 19 is a discrete belt pattern 61 that can have a length L and width W corresponding to the length L and width W of the overall area OA of a nonwoven fabric 10. That is, the forming belt 60 can have discrete belt patterns 61 (as discussed more fully with reference to FIG. 22 below), each having a discrete belt pattern overall area DPOA that corresponds to the overall area OA of the nonwoven fabric 10. FIG. 20 represents a portion of a mask showing the design for one repeat unit of the repeating design in the fabric 10 shown in FIG. 21. The white portion 98 is transparent to UV light, and in the process of making the belt permits UV light to cure an underlying layer of resin which is cured to the reinforcing member 94. After the uncured resin is washed away, the forming belt 60 having a cured resin design as shown in FIG. 19 is produced by seaming the ends of a length of the belt.

The portion of the forming belt shown in FIG. 19 illustrates another benefit of the present disclosure. The portion of a forming belt 60 shown in FIG. 19 can make a fabric 10 shown in FIG. 21. The fabric 10 shown in FIG. 21 can have width W and length L dimensions and an overall area OA making it suitable for use as a topsheet in a disposable diaper, for example. The fabric 10 made on a forming belt 60 as exemplified in FIG. 19 differs from that shown in FIGS. 1-3 in that the pattern of three-dimensional features formed by the discrete resin elements 92 on forming belt 60 are not in a regular, repeating pattern across the entire overall area. Rather, the pattern of three-dimensional raised elements in the discrete belt pattern overall area DPOA can be described as an irregular pattern encompassing distinct portions referred to as zones. The distinction between zones can be visual, i.e., a visually discernible difference, or in the fabric 10 the distinction can produce a difference in intensive properties such as basis weight or density, or combinations of visual and intensive properties. A visually discernible difference exists if an observer in ordinary conditions (20/20 vision, lighting sufficient to read by, for example) can visually discern a pattern difference between the zones, such as the first zone 112 and the second zone 122.

Figure 21:
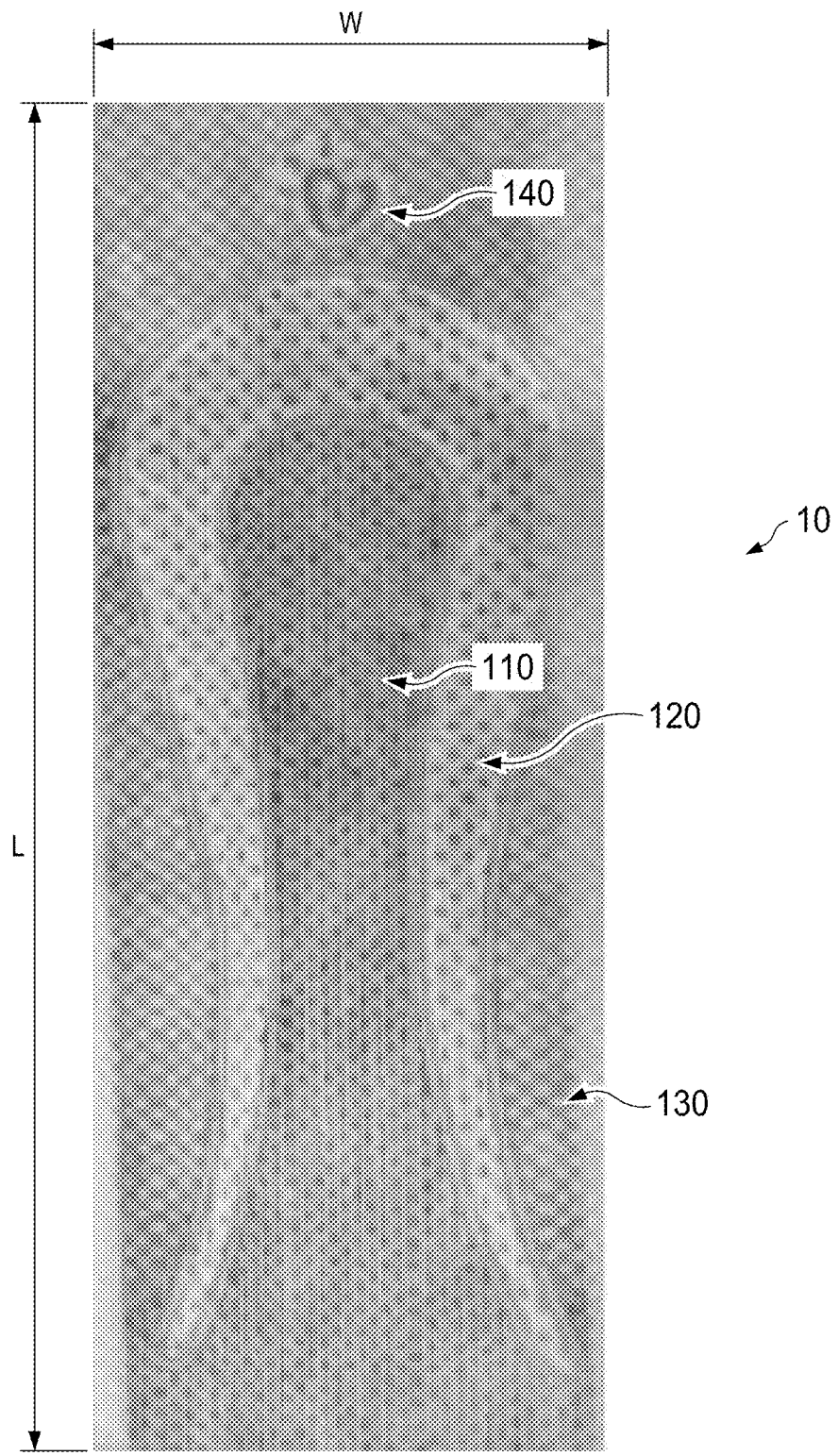
FIG. 21 is a photograph of a fabric of the present disclosure made on the forming belt shown in FIG. 19.

The fabric 10 can also have visually discernible zones corresponding to the zones of the forming belt. As shown in FIG. 21, for example, fabric 10 can have at least two, three, or four visually discernible zones. A first zone 110, having first pattern of three-dimensional features and first average intensive properties, can have a first area generally centrally located within the overall area OA. A second zone 120, having second pattern of three-dimensional features and second average intensive properties, can have a second area distributed generally about, and in an embodiment, completely surrounding, the first zone 110 within the overall area OA. A third zone 130, having third pattern of three-dimensional features and third average intensive properties, can have a third area distributed generally about, and in an embodiment, completely surrounding, the second zone 120 within the overall area OA. A fourth zone 140, having fourth three-dimensional features and fourth average intensive properties, can have a fourth area positioned within the overall area OA in any location, such as at a front area of a topsheet, such as the heart design shown in FIG. 21. In general, there can be n zones, with n being a positive integer. Each of the n zones can have an nth pattern of three-dimensional features and an nth area and nth average intensive properties.

The visually discernible zones as shown in FIG. 21 may comprise visually discernible three-dimensional features. These distinct three-dimensional features may be bounded by relatively higher density (with respect to the interior of a three-dimensional feature) regions that may be in the form of a closed figure, such as the heart shape in FIGS. 1 and 3, and the diamond shape of FIGS. 2 and 3.

As can be understood, rather than having a constant repeating pattern that is uniform across the entire forming belt, the forming belt 60 of the present disclosure allows the production of a nonwoven web that can have repeats of irregular discrete belt patterns 61, each discrete belt pattern 61 being like the discrete belt pattern shown in FIG. 19. The discrete belt patterns 61 each can be used to form one fabric 10 having an overall area OA suitable for use in a disposable absorbent article, such as diaper or sanitary napkin, for example. The fabrics 10 can be produced sequentially, i.e., in line, and, optionally sequentially in parallel lanes, each lane being a sequential line of fabrics 10. The sequential line of fabrics 10 can be produced in a machine direction along an axis parallel to the machine direction. The nonwoven web can then be slit or otherwise cut to size to produce fabrics 10 utilized as a topsheets in disposable absorbent articles, such as diapers or sanitary napkins.

In an embodiment, the pattern within each discrete belt pattern overall area DPOA can be the same or different. That is, the sequentially spaced discrete belt patterns can be substantially identical, or they can differ in visual appearance and/or in the intensive properties produced in nonwoven substrates produced thereon. For example, as shown schematically in FIG. 22, the pattern of three-dimensional raised elements in first forming zone 112 of discrete belt pattern 61A can be different from the pattern of three-dimensional raised elements in first forming zone 112 of discrete belt pattern 61B. The forming belt 60 thus offers flexibility in producing nonwoven webs 10 suitable for use in consumer goods, including disposable absorbent articles. For example, in one package of diapers, the topsheets of at least two diapers can be different because they were produced sequentially in a spunbond process as described herein, with sequential discrete belt patterns having different patterns of zones. In an embodiment, the topsheet or backsheet nonwoven pattern for one size of diaper can be different from the topsheet or backsheet nonwoven of another size of diaper, thereby giving a caretaker a visual clue as to the size of a diaper. Likewise, sanitary napkins can utilize a fabric 10 for a topsheet, with the visual pattern of three-dimensional features denoting the absorbency of the sanitary napkin. In any event, the various patterns of fabrics 10 can be produced on a single belt by making the discrete belt patterns different as desired.

Figure 22:
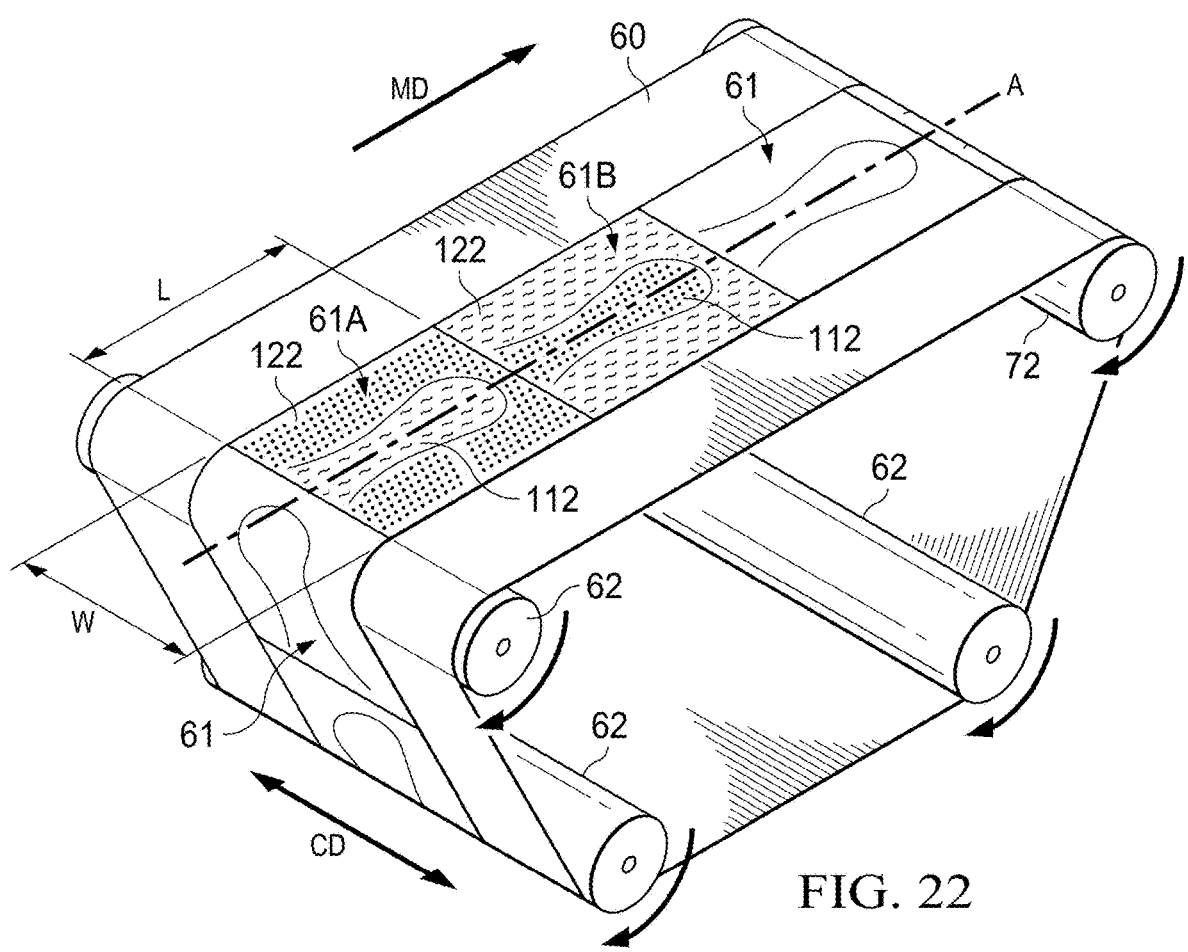
FIG. 22 is a perspective schematic view of a forming belt of the present disclosure.

Thus, the invention can be described, with reference to FIG. 22, as a forming belt having an axis A parallel to a longitudinal direction which is a machine direction. The forming belt 60 can have a plurality of discrete belt patterns 61 ordered in at least one sequential relationship with respect to the longitudinal direction. Each discrete belt pattern 61 can have a discrete belt pattern overall area DPOA defined, in a rectangular-shaped pattern, by a length L and width W, as indicated with respect to discrete belt pattern 61A. Each discrete belt pattern within its overall area DPOA can have a first forming zone 112 having a first pattern of three-dimensional raised elements extending outwardly from the plane of the of the first surface and a second forming zone 122 having second three-dimensional raised elements extending outwardly from the plane of the of the first surface. The first forming zone can have a first air permeability value and the second forming zone can have a second air permeability value, and the first air permeability value can be different from the second air permeability value. The pattern within each sequentially ordered discrete belt pattern overall area DPOA can be the same or different.

By way of example, and referring to the discrete belt pattern 61 of forming belt 60 shown in FIG. 19, and the fabric 10 shown in FIG. 21, the following properties were determined. First zone 110 of fabric 10 can have an average basis weight of about 5 gsm to about 30 gsm; the second zone 120 can have an average basis weight of about 50 gsm to about 70 gsm; and the third zone 130 can have an average basis weight of about 25 gsm to about 60 gsm. The difference in basis weight from one zone to another can be attributed to a difference in air permeability of the forming belt 60. In the embodiment used to make the fabric 10 shown in FIG. 20, in which the basis weights for zones 110, 120, and 130, are 15 gsm, 53 gsm and 25 gsm, respectively, the air permeability of the respective zones 112, 122, and 132 of the forming belt 60 are 379 cfm, 805 cfm, and 625 cfm, respectively. Thus, by varying air permeability in zones in forming belt 10, the intensive properties of average basis weight and average density in zones can be facilitated across the overall area of fabric 10.

Figure 23:
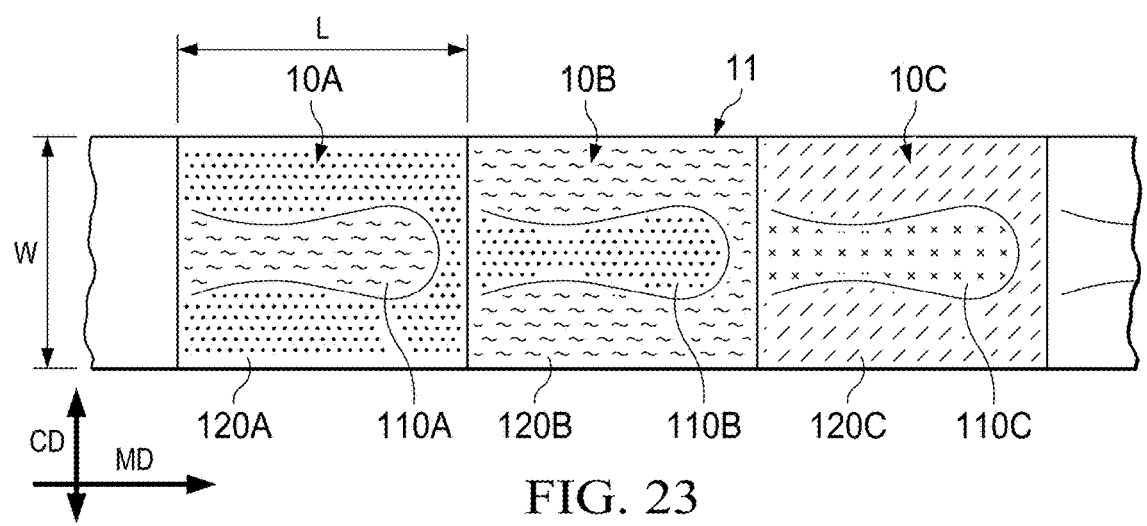
FIG. 23 is plan view of a nonwoven substrate including nonwoven fabrics of the present disclosure.

As can be understood from the description of the forming belt 60 described in FIG. 22, and with reference to FIG. 23, in an embodiment the nonwoven substrate 11 made on belt 60 can be described as a nonwoven substrate 11 having a plurality of portions described herein as fabrics 10 ordered in at least one sequential relationship with respect to the longitudinal direction, i.e., the machine direction when made on forming belt 60. FIG. 23 is a schematic representation of a spunbond nonwoven substrate 11 showing the sequentially ordered fabrics 10, each fabric 10 having a different pattern within the various zones. Each fabric 10 can have an overall area OA defined, in a rectangular-shaped pattern, by a length L and width W. Each sequentially disposed fabric 10 can have within its overall area OA at least a first zone 110, having a first pattern of three-dimensional features and first average intensive properties, and a first area located within the overall area OA; a second zone 120, having a second pattern of three-dimensional features and second average intensive properties, having a second area located within the overall area OA. Optionally, more zones, e.g., a third zone 130, having third pattern of three-dimensional features and third average intensive property and having a third area within the overall area OA can be present. As shown in the exemplary schematic representation of FIG. 23, the first pattern 110A of fabric 10A can be different from the first pattern 110B of fabric 10B, and can be different from first pattern 110C of fabric 10C. The same can be true for second zones 120A, 120B, and 120C.

In general, the sequentially ordered fabrics 10 of the nonwoven substrate 11 made on forming belt 60 can vary in their respective overall areas, intensive properties, and visual appearances. A common intensive property is an intensive property possessed by more than one zone (with respect to zonal patterns, such as that shown in FIG. 21) or region (for regular repeating patterns, such as that shown in FIG. 1). Such intensive properties of the fibrous structure can be average values, and can include, without limitation, density, basis weight, elevation, and opacity. For example, if a density is a common intensive property of two differential zones or regions, a value of the density in one zone or region can differ from a value of the density in the other zone or region. Zones (such as, for example, a first zone and a second zone) are identifiable areas distinguishable from one another by distinct intensive properties averaged within the zone.

Figure 24:
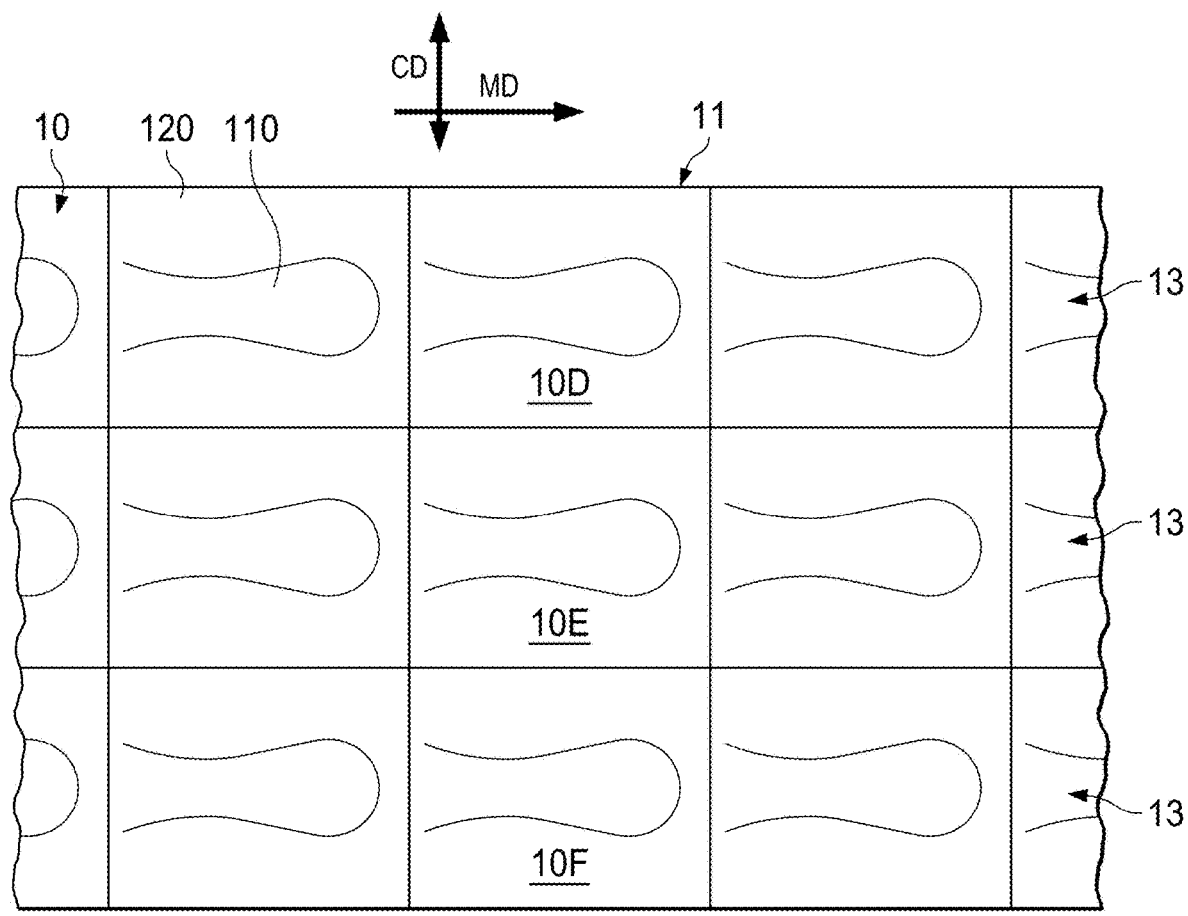
FIG. 24 is plan view of a nonwoven substrate including nonwoven fabrics of the present disclosure.

Once produced, the individual fabrics 10 can be cut to size and utilized for their intended purposes, such as for topsheets in disposable absorbent articles. For example, a disposable diaper 1006 in a flattened orientation is shown in FIG. 24. One fabric 10 is cut to the appropriate overall area and adhered into the diaper 1006 by means known in the art. Fabrics 10 can be cut prior to being assembled into a diaper 1006, or during the diaper making process the nonwoven substrate 11 can be brought together with other diaper components in web form, and cut to size after assembly.

As can be understood with reference to FIG. 24, in an embodiment the nonwoven substrate 11 made on belt 60 can be described as a nonwoven fabric 11 having a plurality of portions described herein as fabrics 10 ordered in at least one sequential relationship with respect to the longitudinal direction, i.e., the machine direction when made on forming belt 60, in at least one side-by-side relationship, i.e., in the cross machine direction when made on forming belt 60. FIG. 24 is a schematic representation of a spunbond nonwoven substrate 11 showing the sequentially ordered fabrics 10 in adjacent machine direction lanes 13, adjacent lanes having the side-by each fabrics 10, called out in FIG. 24 as 10D, 10E, and 10F. Each fabric 10 can have an overall area OA defined, in a rectangular-shaped pattern, by a length L and width W. Each sequentially disposed fabric 10 can have within its overall area OA at least a first zone 110, having a first pattern of three-dimensional features and first average intensive properties, and a first area located within the overall area OA; a second zone 120, having a second pattern of three-dimensional features and second average intensive properties, having a second area located within the overall area OA. Optionally, more zones, e.g., a third zone 130, having third pattern of three-dimensional features and third average intensive property and having a third area within the overall area OA can be present. Each fabric 10 in side-by-side lanes can be substantially identical, or they can be different with respect to size, visual appearance, and/or intensive properties. Once produced, the nonwoven substrate 11 can be reeled for slitting into lanes for processing into consumer products, or slit and then reeled.

By way of representative sample to compare basis weight differentials in a fabric 10 made with a regular, repeating, uniform pattern and a fabric 10 made with a non-uniform, zonal pattern, the fabric 10 of Example 1 was compared with a fabric having a pattern similar to that shown in FIG. 21, and referred to as Example 3. Example 3 is a bicomponent spunbond nonwoven web produced on the apparatus disclosed herein by spinning 50:50 ratio of polyethylene sheath (Aspun-6850-A obtained from Dow chemical company) and polypropylene core (PH-835 obtained from LyondellBasell) in a trilobal fiber configuration. The spunbond, bicomponent, trilobal fibers were laid down on a forming belt 60 moving at a linear speed of about 25 meters per minute to an average basis weight of 30 grams per square meter on a forming belt with a zonal pattern as shown in FIG. 19. The second substrate was formed under identical conditions, but had at least one section having a regular, repeating, uniform pattern on a forming belt as shown in FIG. 16, from which basis weight was determined. Fiber spinning conditions, through-put, forming belt line speed and compaction roll bonding temperature were identical for both substrates.

Example 3

A bicomponent spunbond nonwoven fabric that was produced by spinning a 50:50 ratio of polyethylene sheath (Aspun-6850-A obtained from Dow chemical company) and polypropylene core (PH-835 obtained from LyondellBasell) in a trilobal fiber configuration to an average basis weight of 30 grams per square meter. A nonwoven fabric was produced as described with respect to FIGS. 7 and 8 moving at a forming belt linear speed of about 25 meters per minute to form a fabric having zonal pattern as shown in FIG. 20. Fibers of the fabric were further bonded on first side 12 by heated compaction rolls 70, 72 at 130° C., and the fabric was wound on to a reel at winder 75.

Example 4

A bicomponent spunbond nonwoven fabric that was produced by spinning a 50:50 ratio of polyethylene sheath (Aspun-6850-A obtained from Dow chemical company) and polypropylene core (PH-835 obtained from LyondellBasell) in a trilobal fiber configuration to an average basis weight of 30 grams per square meter. A nonwoven fabric was produced as described with respect to FIGS. 7 and 8 moving at a forming belt linear speed of about 25 meters per minute to form a fabric having repeating (non-zonal) pattern as shown in FIG. 2. Fibers of the fabric were further bonded on first side 12 by heated compaction rolls 70, 72 at 130° C., and being wound on to a reel at winder 75.

Figure 25A:
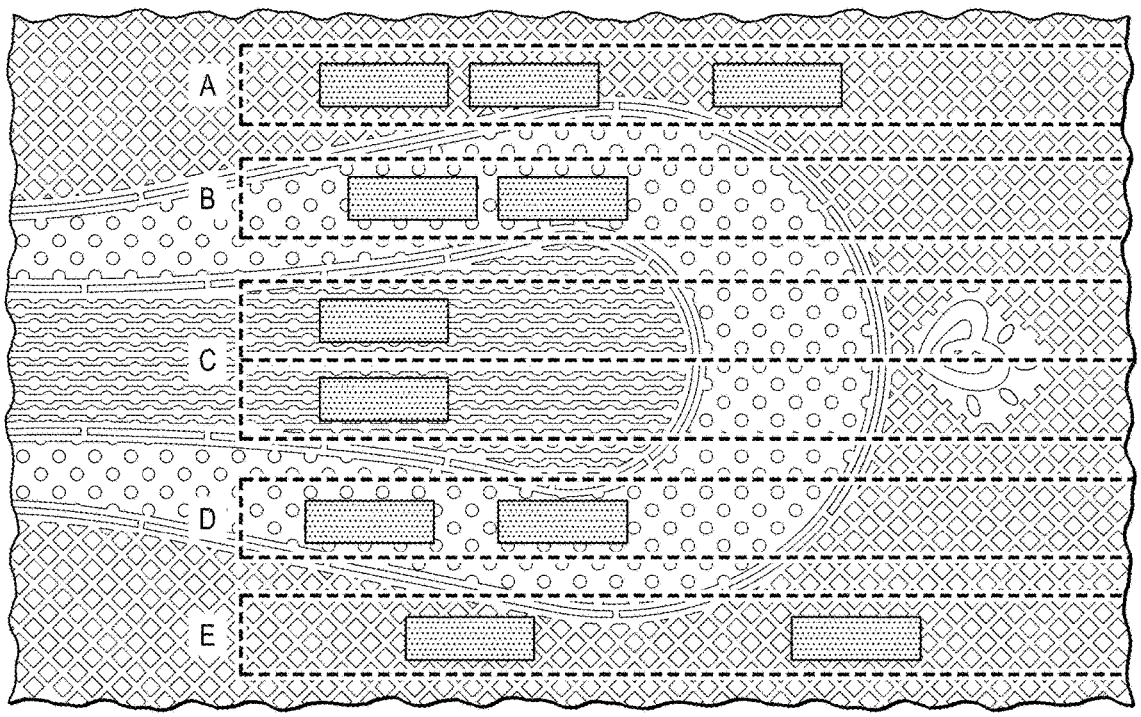
FIG. 25A is a plan view of a fabric of the present disclosure with portions removed for measurement of local basis weight.
Figure 25B:
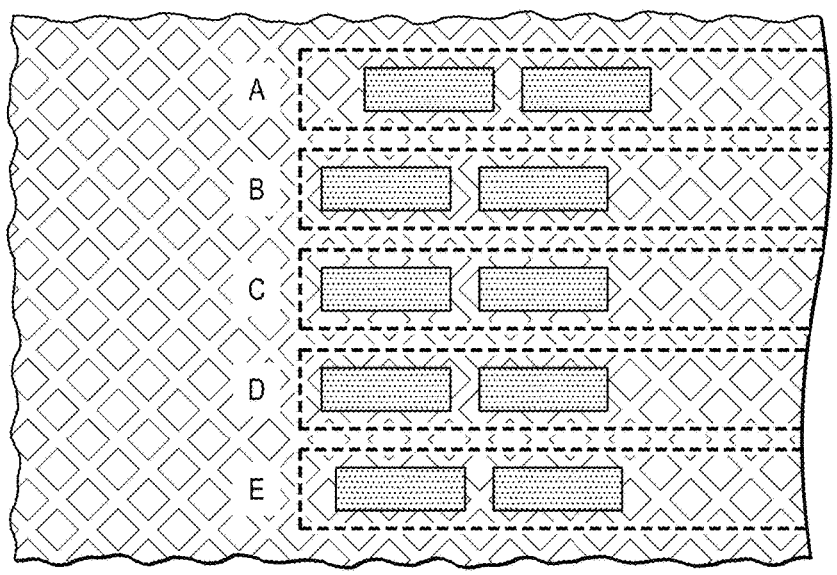
FIG. 25B is a plan view of a fabric of the present disclosure with portions removed for measurement of local basis weight.
Figure 26:
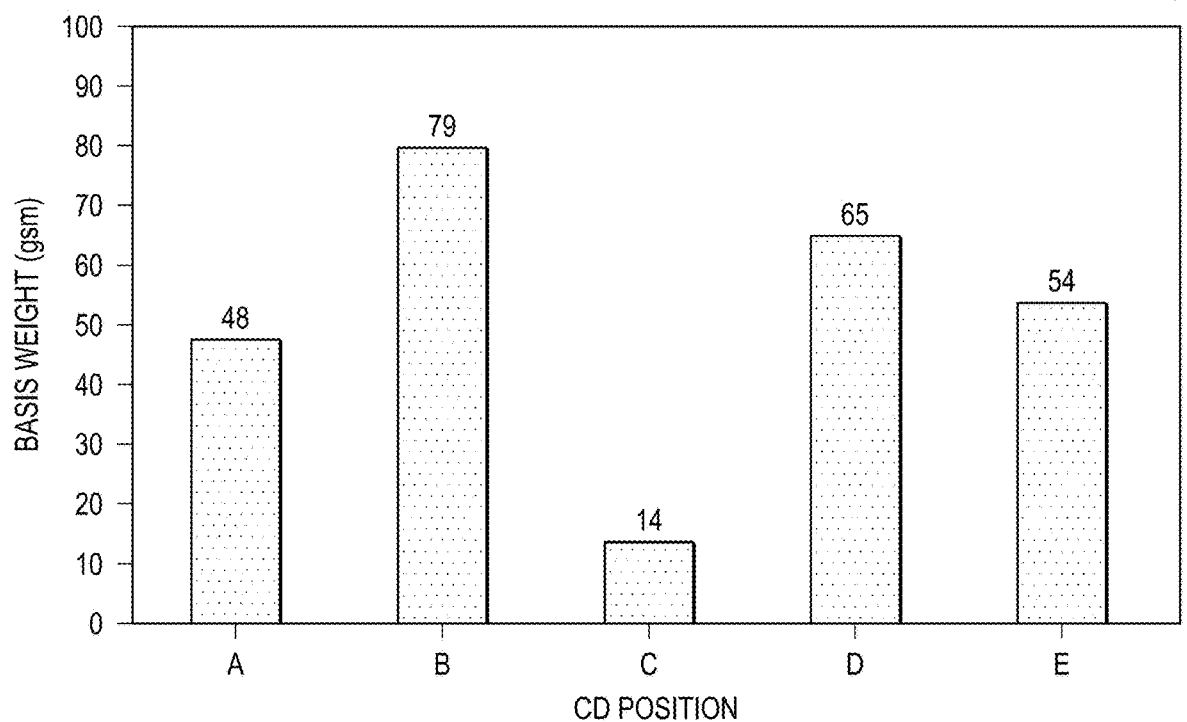
FIG. 26 is a graphical representation of cross-directional variation in basis weight in a fabric of the present disclosure.

Table 2 below shows average local basis weight, measured according to the Localized Basis Weight test method herein, and averaged over 10 samples. The samples for measurement were taken from the fabrics as shown in FIGS. 25A and 25B, in which the dark rectangles are where a 3 cm$^2$ sample was removed for measurement. As can be seen, the fabrics are labeled across the cross-direction (CD) as A-E. The measurements shown not only a significant difference in basis weight between zones of the zonal fabric, but a CD distribution which is depicted graphically in FIG. 26.

TABLE 2

Measured Average Basis Weight distribution in fabric 10 in grams per square meter (gsm)

| Region as Depicted in FIG. 25 | Example 3: Zonal Fabric Basis Weights | Example 4: Non-zonal Fabric Basis weights |
| --- | --- | --- |
| A | 48 gsm | 43 gsm |
| B | 79 gsm | 37 gsm |
| C | 14 gsm | 32 gsm |
| D | 65 gsm | 36 gsm |
| E | 54 gsm | 36 gsm |

As can be seen in Table 2, fabrics 10 made on forming belts 60 having zones of differing air permeability demonstrate substantial variation in fiber laydown and thus basis weights within the CD of fabric 10 suggesting the ability for fibers to travel with air into high permeability zones. The non-zonal, regular repeating pattern fabric 10 exhibits approximately the same basis weights within the CD of fabric.

In addition to differences in air permeability of the various zones of the forming belt 60, the structure of forming belt 60 can affect other intensive properties of zones in the fabric 10, such as average caliper, average softness, average compression resistance, and fluid absorption properties.

Another aspect of this invention relates to spunbond commercial lines where multiple beams are utilized for improved laydown opacity and uniformity of the fabric. In some cases, there the apparatus can include triple spunbond beams (known in the art as "SSS") and may be combined with meltblown (M), for example, in an apparatus known as an "SSMMS" spunbond line.

By calendaring the fabric 10 to have point bonds 90, fuzzing can be reduced. Fuzzing refers to the tendency of fibers to become loose and removed from the fabric 10. Loosening and removal can be because of frictional engagement with manufacturing equipment during production of disposable absorbent articles, or another surface, such as the skin of a person interacting with the fabric 10. In some uses, such as for topsheets in disposable absorbent articles, fuzzing is a negative consumer phenomena. But bonding fibers in place can also be a consumer negative as it can produce roughness on the surface of an otherwise soft nonwoven substrate. We have found expectedly the nonwoven fabrics substrates and nonwoven fabrics of the present disclosure can endure an increase in bonding (and a consequent decrease in fuzzing) with minimal loss in softness. Bonding can be accomplished by relatively closely spaced point bonds 90, with the spacing being determined by the desired level of fuzzing reduction. Bonding can also be achieved by known methods for chemically or thermally bonding nonwoven fibers, such as thermal bonding, ultrasonic bonding, pressure bonding, latex adhesive bonding, and combinations of such methods. Fuzz reduction by bonding is illustrated with respect to Examples 5 and 6 below.

Example 5

Figure 36:
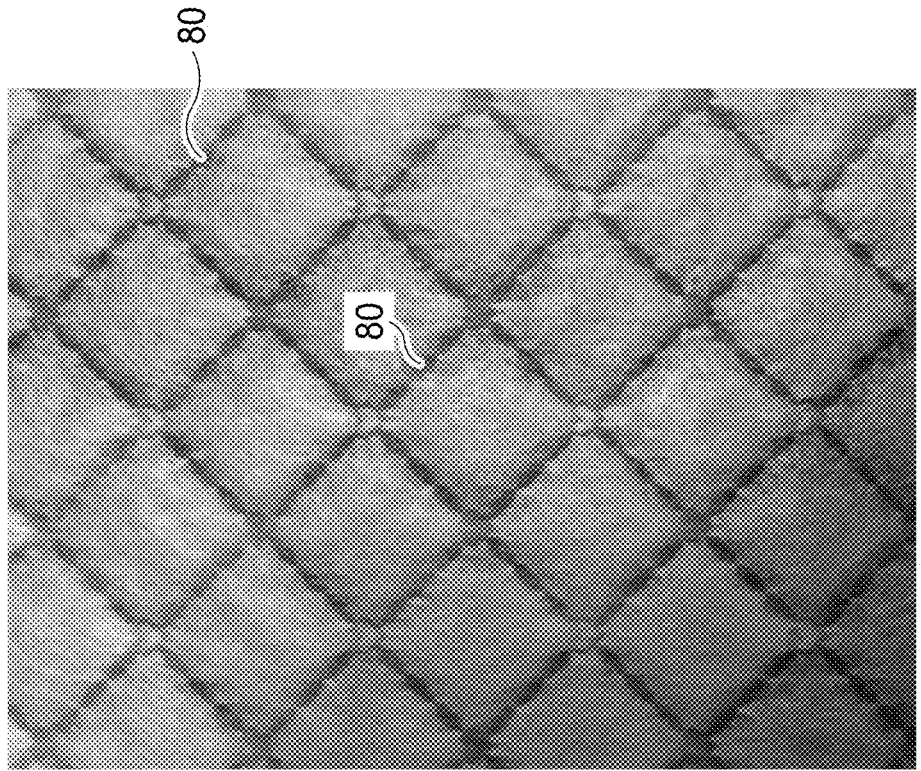
FIG. 36 is a photograph of an embodiment of the present disclosure.

A bicomponent spunbond nonwoven fabric was produced by spinning a 50:50 ratio of polyethylene sheath (Aspun-6850-A obtained from Dow chemical company) and polypropylene core (PH-835 obtained from LyondellBasell) in a trilobal fiber configuration to an average basis weight of about 30 grams per square meter on a forming belt as described with respect to FIGS. 7 and 8 moving at a linear speed of about 25 meters per minute to form a fabric having the repeating pattern as shown in FIG. 36 Fibers of the fabric were further bonded on first side 12 by compaction rolls 70, 72 with compaction roll 70 heated to 130° C. to form substantially continuous bonds 80.

Example 6

Figure 37:
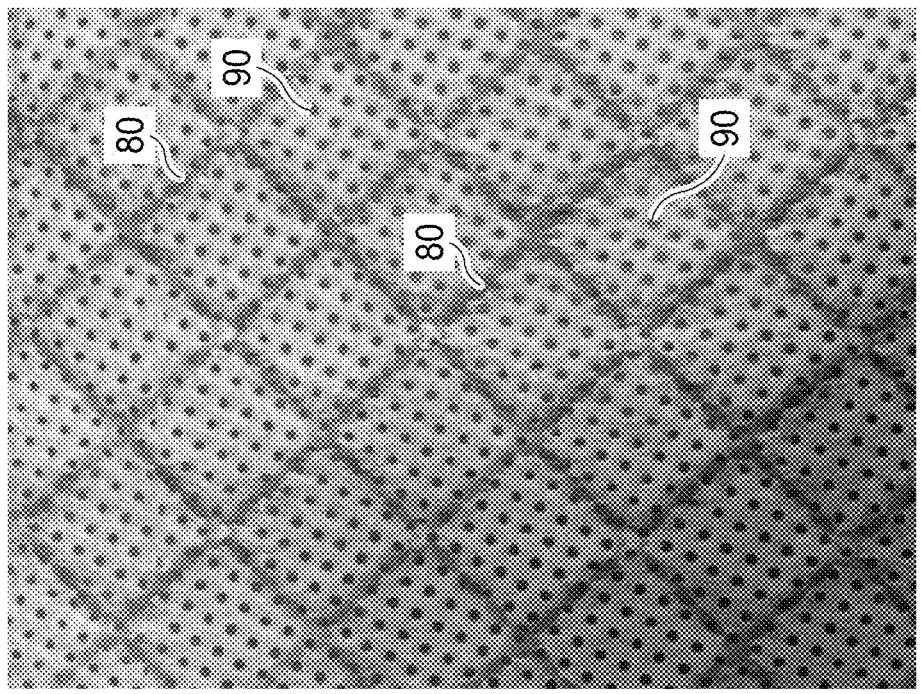
FIG. 37 is a photograph of an embodiment of the present disclosure.

A bicomponent spunbond nonwoven fabric was produced by spinning a 50:50 ratio of polyethylene sheath (Aspun-6850-A obtained from Dow chemical company) and polypropylene core (PH-835 obtained from LyondellBasell) in a trilobal fiber configuration to an average basis weight of about 30 grams per square meter on a forming belt as described with respect to FIGS. 7 and 8 moving at a linear speed of about 25 meters per minute to form a fabric having the repeating pattern described with respect FIG. 37 Fibers of the fabric were further bonded on first side 12 by compaction rolls 70, 72 with compaction roll 70 heated to 130° C. to form substantially continuous bonds 80. Fibers of the fabric were further calendar bonded at calendar rolls 71, 73, with roll 73 being an engraved roll having raised portions 88 in the form of pins with 1.25 mm pin height and 0.62 mm open gap in a 10% point bonding pattern. The roll 73 was heated to 135C to form point bonds 90 on second side 14 of fabric 10, as shown in FIG. 11.

The fabrics 10 of Examples 5 and 6 differed only in the absence or presence of point bonds 90. The second side 14 of the fabrics 10 underwent fuzz testing according to the Fuzz Level Test to determine the effectiveness of the point bonds in securing fibers to the surface of the fabric. The results of fuzz testing of Examples 5 and 6 are shown in Table 3.

TABLE 3

MD Fuzz Results

| Sample No. | MD Fuzz Value (mg/cm$^2$) |
|---|---|
| Example 5 | 0.36 |
| Example 6 | 0.19 |

As shown above, the point bonds 90 result in a dramatic decrease in the MD Fuzz Value. It unexpectedly retained its softness, absorbency, and aesthetic benefits in spite of the bonding treatment and now also has the desired resistance to fuzz upon consumer use.

Packages

The absorbent articles of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Accordingly, packages of the absorbent articles of the present disclosure may have an In-Bag Stack Height of less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

Figure 27:
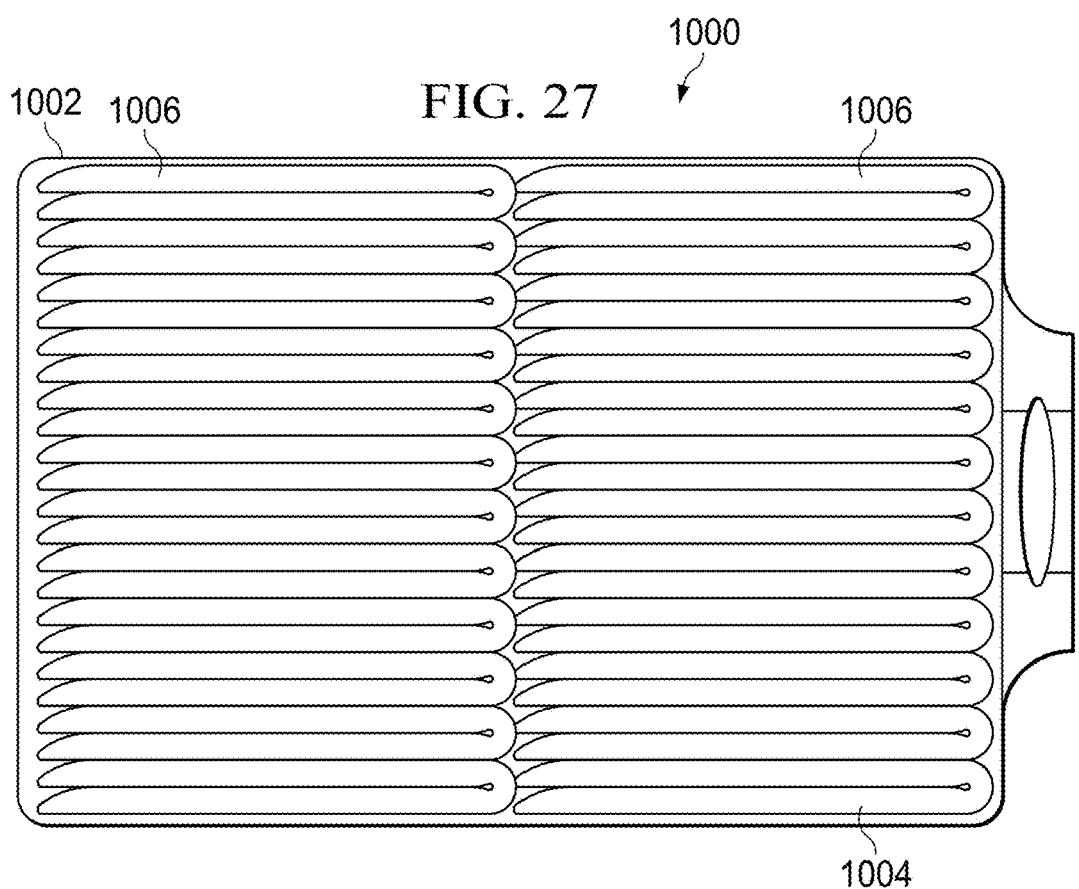
FIG. 27 is a schematic view of a package of the present disclosure.

FIG. 27 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006.

General Description of an Absorbent Article

Figure 28:
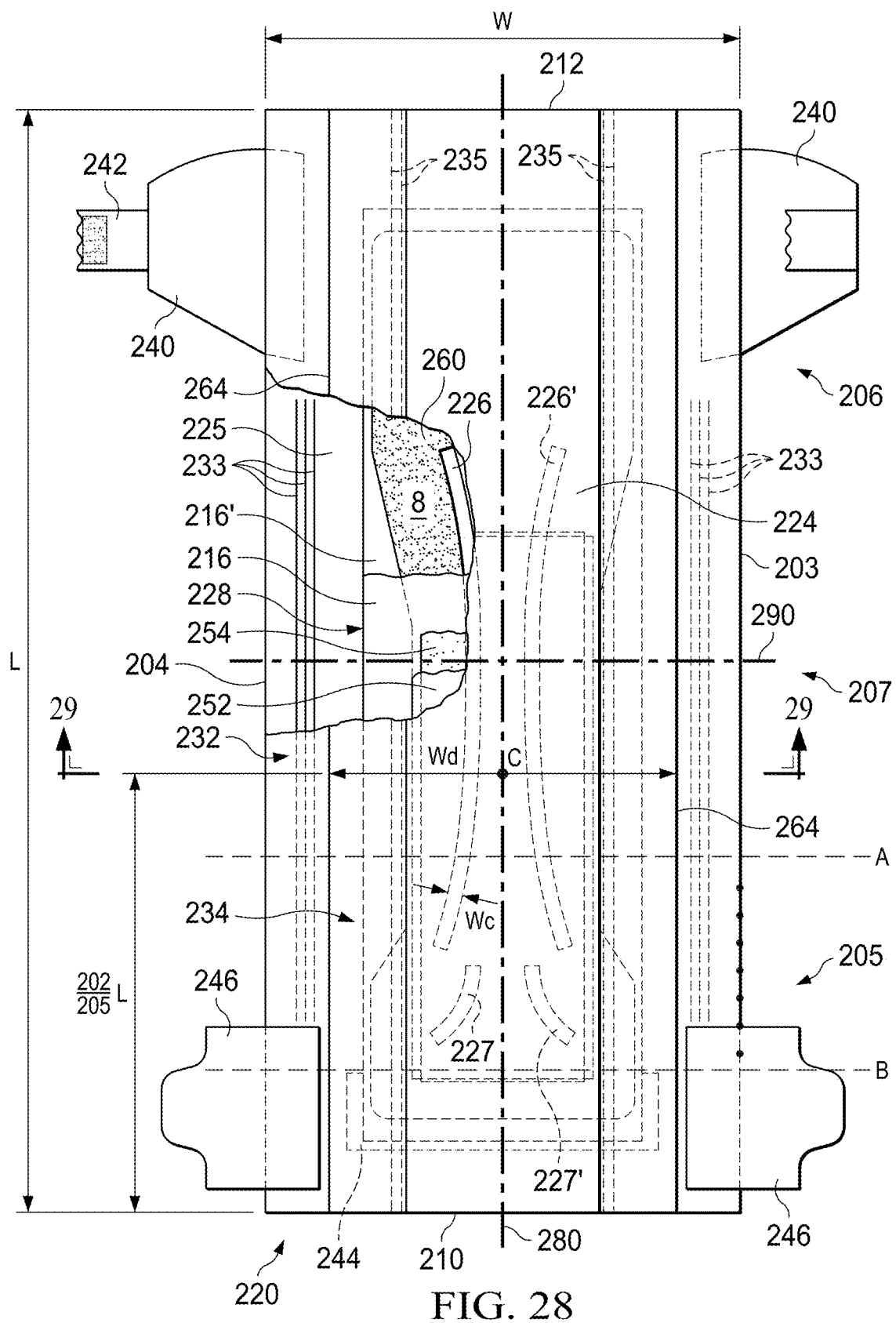
FIG. 28 is a plan view of an absorbent article of the present disclosure.
Figure 29:
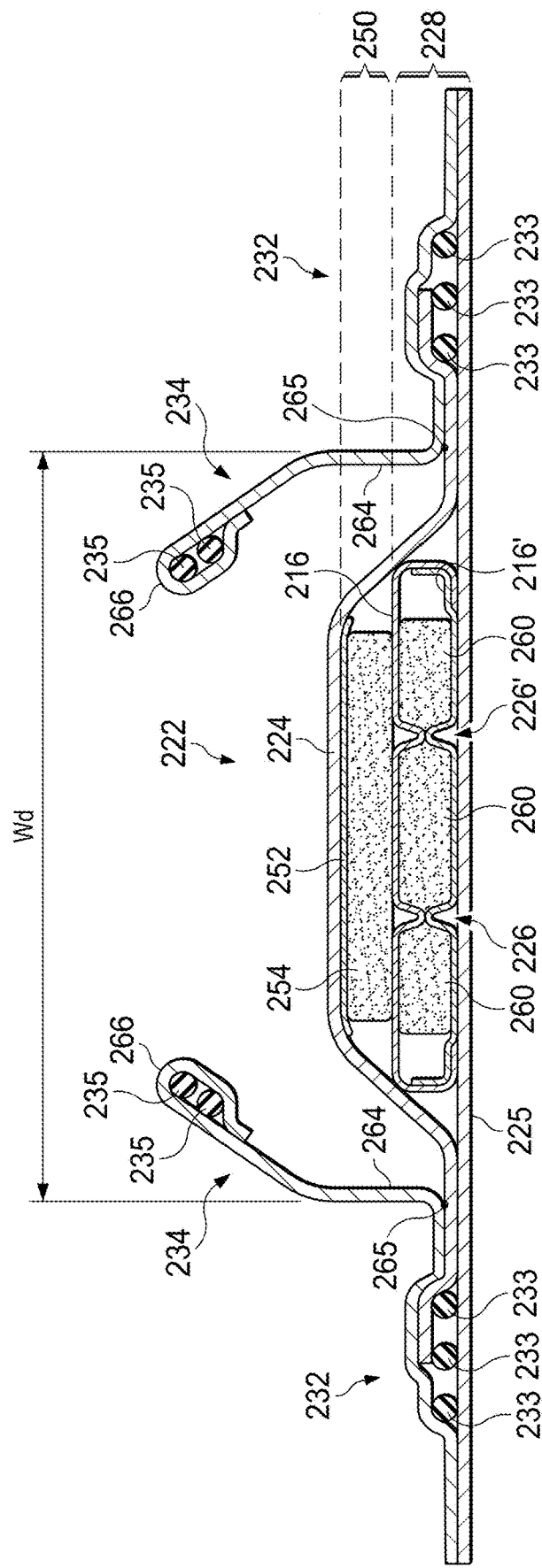
FIG. 29 is a plan view of an absorbent article of the present disclosure
Figure 30:
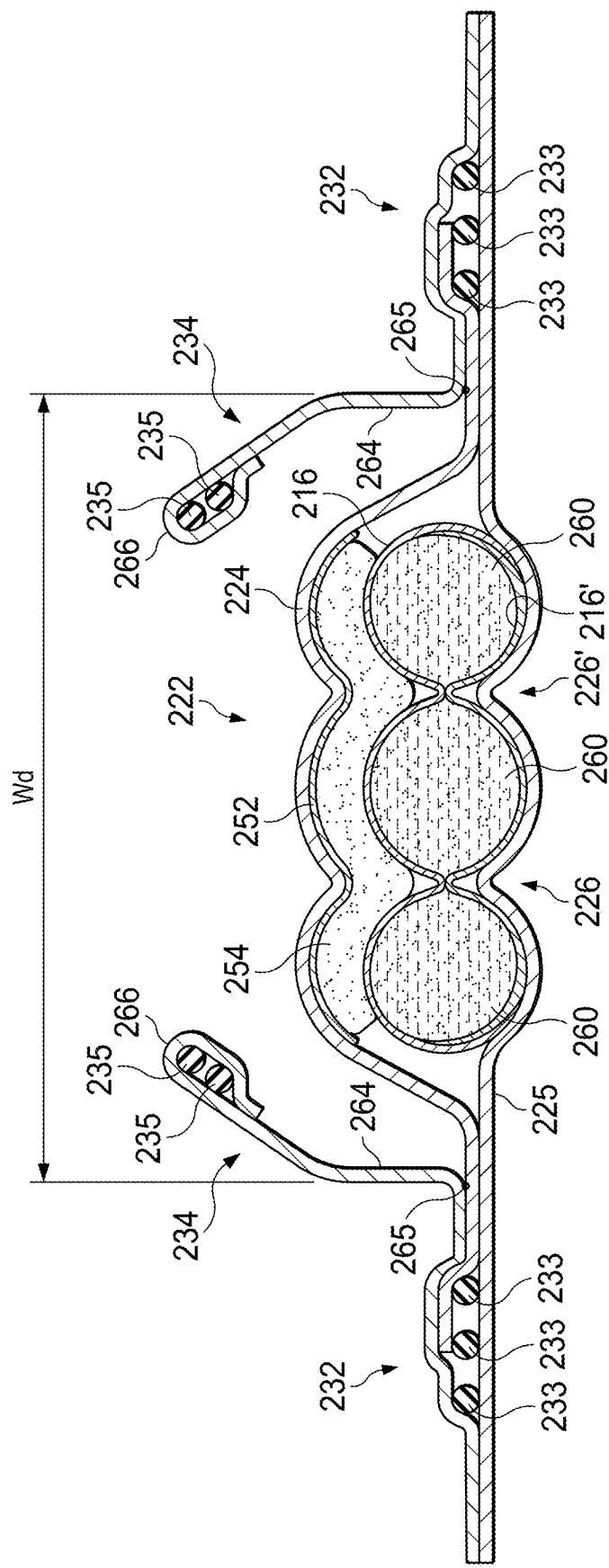
FIG. 30 is a cross sectional view of Section 29-29 of FIG. 28.

The three-dimensional nonwoven fabrics 10 of the present disclosure can be utilized as a component of absorbent articles, such as diapers, child care items such as training pants, feminine care items such as sanitary napkins, and adult care items such as incontinence products, pads, and pants An example absorbent article in the form of a diaper 220 is represented in FIGS. 28-30. FIG. 28 is a plan view of the example diaper 220, in a flat, laid-out state, with portions of the structure being cut-away to more clearly show the construction of the diaper 220. The wearer-facing surface of the diaper 220 of FIG. 28 is facing the viewer. This diaper 220 is shown for illustration purpose only as the three-dimensional nonwoven materials of the present disclosure may be used as one or more components of an absorbent article, such as the topsheet, the acquisition layer, the topsheet and the acquisition layer, or the topsheet and the acquisition and/or the distribution system ("ADS"). In any event the three-dimensional nonwoven materials of the present disclosure may be liquid permeable.

The absorbent article 220 may comprise a liquid permeable material or topsheet 224, a liquid impermeable material or backsheet 225, an absorbent core 228 positioned at least partially intermediate the topsheet 224 and the backsheet 225, and barrier leg cuffs 234. The absorbent article may also comprise an ADS 250, which in the example represented comprises a distribution layer 254 and an acquisition layer 252, which will be further discussed below. The absorbent article 220 may also comprise elasticized gasketing cuffs 232 comprising elastics 233 joined to a chassis of the absorbent article, typically via the topsheet and/or backsheet, and substantially planar with the chassis of the diaper.

Figure 31:
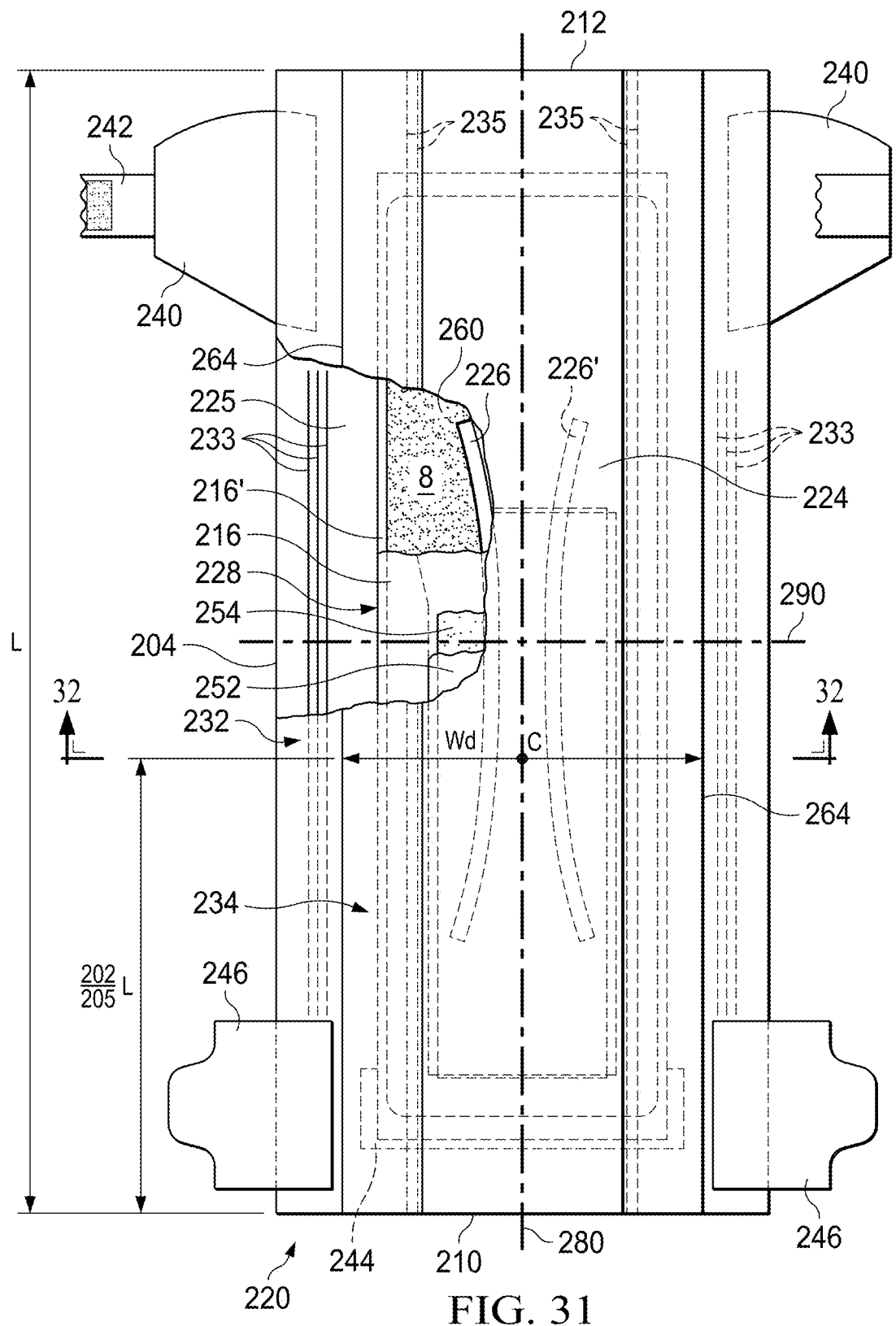
FIG. 31 is a plan view of an absorbent article of the present disclosure.

FIGS. 28 and 31 also show typical taped diaper components such as a fastening system comprising tabs 242 attached towards the rear edge of the article and cooperating with a landing zone 244 on the front of the absorbent article. The absorbent article may also comprise other typical elements, which are not represented, such as a rear elastic waist feature, a front elastic waist feature, transverse barrier cuff(s), and/or a lotion application, for example.

The absorbent article 220 comprises a front waist edge 210, a rear waist edge 212 longitudinally opposing the front waist edge 210, a first side edge 203, and a second side edge 204 laterally opposing the first side edge 203. The front waist edge 210 is the edge of the article which is intended to be placed towards the front of the user when worn, and the rear waist edge 212 is the opposite edge. The absorbent article 220 may have a longitudinal axis 280 extending from the lateral midpoint of the front waist edge 210 to a lateral midpoint of the rear waist edge 212 of the article and dividing the article in two substantially symmetrical halves relative to the longitudinal axis 280, with the article placed flat, laid-out and viewed from above as in FIG. 28. The absorbent article 220 may also have a lateral axis 290 extending from the longitudinal midpoint of the first side edge 203 to the longitudinal midpoint of the second side edge 204. The length, L, of the article may be measured along the longitudinal axis 280 from the front waist edge 210 to the rear waist edge 212. The width, W, of the absorbent article may be measured along the lateral axis 290 from the first side edge 203 to the second side edge 204. The absorbent article may comprise a crotch point C defined herein as the point placed on the longitudinal axis at a distance of two fifth (2/5) of L starting from the front edge 210 of the article 220. The article may comprise a front waist region 205, a rear waist region 206, and a crotch region 207. The front waist region 205, the rear waist region 206, and the crotch region 207 may each define ⅓ of the longitudinal length, L, of the absorbent article.

The topsheet 224, the backsheet 225, the absorbent core 228, and the other article components may be assembled in a variety of configurations, in particular by gluing or heat embossing, for example.

The absorbent core 228 may comprise an absorbent material comprising at least 80% by weight, at least 85% by weight, at least 90% by weight, at least 95% by weight, or at least 99% by weight of superabsorbent polymers, and a core wrap enclosing the superabsorbent polymers. The core wrap may typically comprise two materials, substrates, or nonwoven materials 216 and 216' for the top side and the bottom side of the core. These types of cores are known as airfelt-free cores. The core may comprise one or more channels, represented in FIG. 28 as the four channels 226, 226' and 227, 227'. The channels 226, 226', 227, and 227' are optional features. Instead, the core may not have any channels or may have any number of channels.

These and other components of the example absorbent articles will now be discussed in more details.

Topsheet

In the present disclosure, the topsheet (the portion of the absorbent article that contacts the wearer's skin and receives the fluids) may be formed of a portion of, or all of, one or more of the three-dimensional nonwoven materials described herein and/or have one or more of the nonwoven materials positioned thereon and/or joined thereto, so that the nonwoven material(s) contact(s) the wearer's skin. Other portions of the topsheet (other than the three-dimensional nonwoven materials) may also contact the wearer's skin. The three-dimensional nonwoven materials may be positioned as a strip or a patch on top of the typical topsheet 224. Alternatively, the three-dimensional nonwoven material may only form a central CD area of the topsheet. The central CD area may extend the full MD length of the topsheet or less than the full MD length of the topsheet.

The topsheet 224 may be joined to the backsheet 225, the absorbent core 228 and/or any other layers as is known to those of skill in the art. Usually, the topsheet 224 and the backsheet 225 are joined directly to each other in some locations (e.g., on or close to the periphery of the absorbent article) and are indirectly joined together in other locations by directly joining them to one or more other elements of the article 220.

The topsheet 224 may be compliant, soft-feeling, and non-irritating to the wearer's skin. Further, a portion of, or all of, the topsheet 224 may be liquid permeable, permitting liquids to readily penetrate through its thickness. Furthermore, a portion of, or all of, the topsheet 224 may be treated with surfactants or other agents to either hydrophilize the web or make it hydrophobic. Any portion of the topsheet 224 may be coated with a lotion and/or a skin care composition as is generally disclosed in the art. The topsheet 224 may also comprise or be treated with antibacterial agents.

Backsheet

The backsheet 225 is generally that portion of the absorbent article 220 positioned adjacent the garment-facing surface of the absorbent core 228 and which prevents, or at least inhibits, the fluids and bodily exudates absorbed and contained therein from soiling articles such as bedsheets and undergarments. The backsheet 225 is typically impermeable, or at least substantially impermeable, to fluids (e.g., urine). The backsheet may, for example, be or comprise a thin plastic film such as a thermoplastic film having a thickness of about 0.012 mm to about 0.051 mm. Other suitable backsheet materials may include breathable materials which permit vapors to escape from the absorbent article 220, while still preventing, or at least inhibiting, fluids from passing through the backsheet 225.

The backsheet 225 may be joined to the topsheet 224, the absorbent core 228, and/or any other element of the absorbent article 220 by any attachment methods known to those of skill in the art.

The absorbent article may comprise a backsheet comprising an outer cover or an outer cover nonwoven. An outer cover or outer cover nonwoven of the absorbent article 220 may cover at least a portion of, or all of, the backsheet 225 to form a soft garment-facing surface of the absorbent article. The outer cover or outer cover nonwoven may be formed of the high loft, three-dimensional nonwoven materials described herein. Alternatively, the outer cover or outer cover nonwoven may comprise one or more known outer cover materials. If the outer cover comprises one of the three-dimensional nonwoven materials of the present disclosure, the three-dimensional nonwoven material of the outer cover may or may not match (e.g., same material, same pattern) a three-dimensional nonwoven material used as the topsheet or the topsheet and the acquisition layer of the absorbent article. In other instances, the outer cover may have a printed or otherwise applied pattern that matches or visually resembles the pattern of the three-dimensional nonwoven materials used as the topsheet or the topsheet and the acquisition layer laminate of the absorbent article. The outer cover may be joined to at least a portion of the backsheet 225 through mechanical bonding, ultrasonic, thermal bonding, adhesive bonding, or other suitable methods of attachment.

Absorbent Core

The absorbent core is the component of the absorbent article that has the most absorbent capacity and that comprises an absorbent material and a core wrap or core bag enclosing the absorbent material. The absorbent core does not include the acquisition and/or distribution system or any other components of the absorbent article which are not either integral part of the core wrap or core bag or placed within the core wrap or core bag. The absorbent core may comprise, consist essentially of, or consist of, a core wrap, an absorbent material (e.g., superabsorbent polymers and little or no cellulose fibers) as discussed, and glue.

The absorbent core 228 may comprise an absorbent material with a high amount of superabsorbent polymers (herein abbreviated as "SAP") enclosed within the core wrap. The SAP content may represent 70%-100% or at least 70%, 75%, 80%, 85%, 90%, 95%, 99%, or 100%, by weight of the absorbent material, contained in the core wrap. The core wrap is not considered as absorbent material for the purpose of assessing the percentage of SAP in the absorbent core. The absorbent core may contain airfelt with or without superabsorbent polymers.

By "absorbent material" it is meant a material which has some absorbency property or liquid retaining properties, such as SAP, cellulosic fibers as well as synthetic fibers. Typically, glues used in making absorbent cores have no or little absorbency properties and are not considered as absorbent material. The SAP content may be higher than 80%, for example at least 85%, at least 90%, at least 95%, at least 99%, and even up to and including 100% of the weight of the absorbent material contained within the core wrap. This airfelt-free core is relatively thin compared to a conventional core typically comprising between 40-60% SAP by weight and a high content of cellulose fibers. The absorbent material may in particular comprises less than 15% weight percent or less than 10% weight percent of natural, cellulosic, or synthetic fibers, less than 5% weight percent, less than 3% weight percent, less than 2% weight percent, less than 1% weight percent, or may even be substantially free of natural, cellulosic, and/or synthetic fibers.

As referenced above, the airfelt-free cores with very little or no natural, cellulosic and/or synthetic fibers are quite thin compared to conventional cores, thereby making the overall absorbent article thinner than absorbent articles with cores comprising mixed SAP and cellulosic fibers (e.g., 40-60% cellulose fibers). This core thinness can lead to consumer perceptions of reduced absorbency and performance, although technically this is not the case. Presently, these thin cores have typically been used with substantially planer or apertured topsheets. Furthermore, absorbent articles having these thin airfelt-free cores have reduced capillary void space since there is little or no natural, cellulosic, or synthetic fibers in the cores. Thus, there may sometimes not be enough capillary void space in the absorbent article to fully accept multiple insults of bodily exudates or a single large insult.

To solve such problems, the present disclosure provides absorbent articles with these thin airfelt-free cores in combination with one of the high-loft, three-dimensional nonwoven materials described herein as a topsheet or as a topsheet and acquisition layer laminate. In such an instance, consumer perception of absorbency and performance, through the increased thickness of the absorbent article owing to the additional thickness provided by the high-loft, three-dimensional nonwoven material, is increased. Furthermore, the three-dimensional nonwoven materials, when used with these thin airfelt-free cores and as the topsheet or the topsheet and acquisition layer laminate, add capillary void space back into the absorbent articles, while still allowing for minimal stack heights, thereby passing cost savings onto consumers and manufactures. As such, the absorbent articles of the present disclosure may easily absorb multiple bodily exudate insults or single large insults owing to this increased capillary void space. Additionally, absorbent articles that comprise the nonwoven materials as the topsheet or the topsheet and acquisition layer laminate provide consumers with an aesthetically pleasing topsheet relative to a planer topsheet or an apertured topsheet with an increased thickness and thus the consumer perceptions of absorbency and performance.

Figure 32:
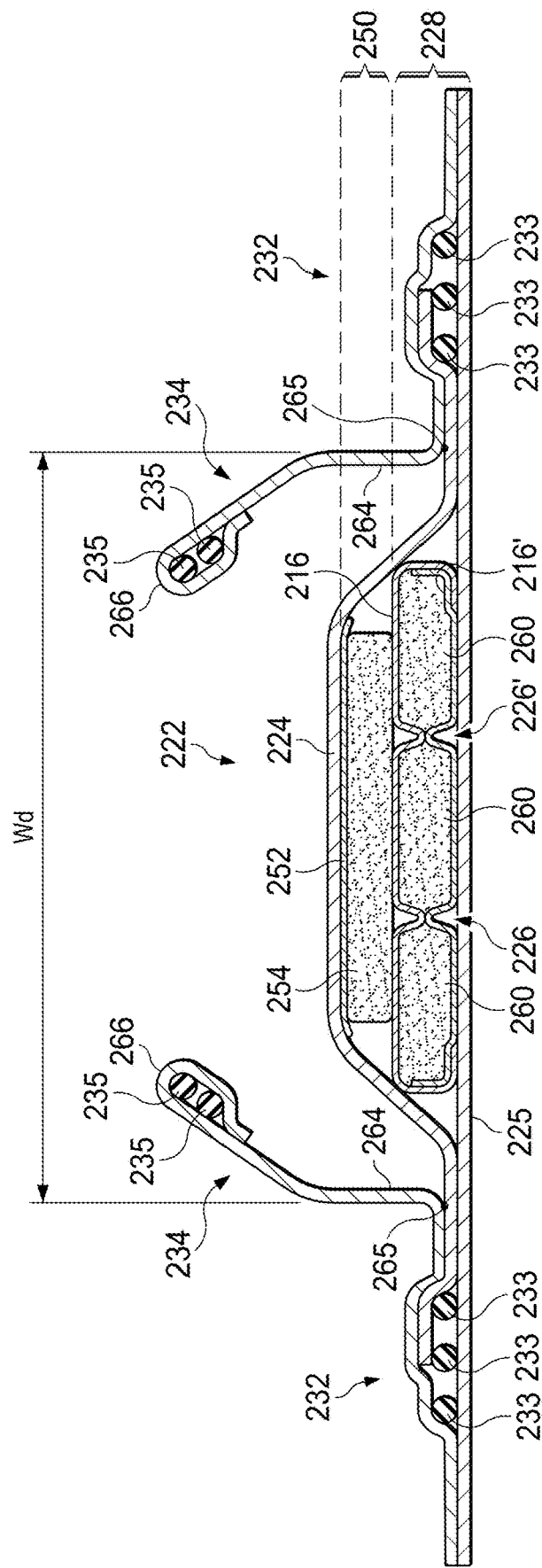
FIG. 32 is a cross sectional view of Section 32-32 of FIG. 31.
Figure 33:
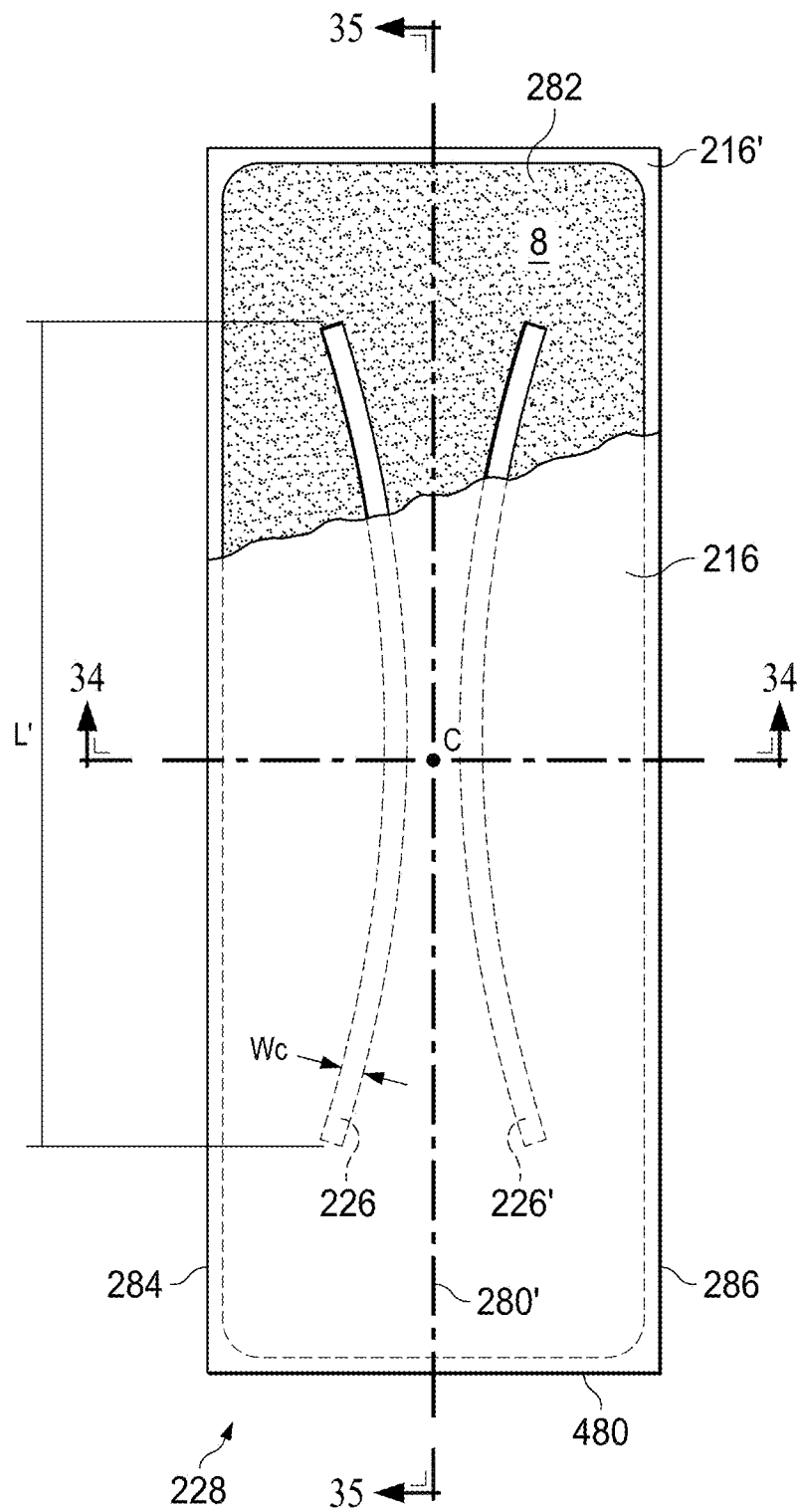
FIG. 33 is a plan view of an absorbent article of the present disclosure.
Figure 34:
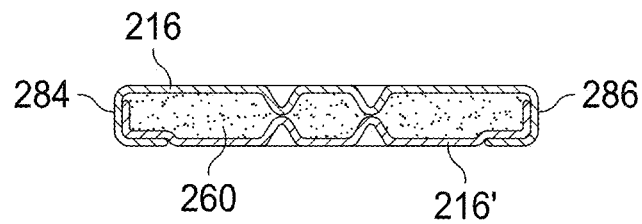
FIG. 34 is a cross sectional view of Section 34-34 of FIG. 33.
Figure 35:
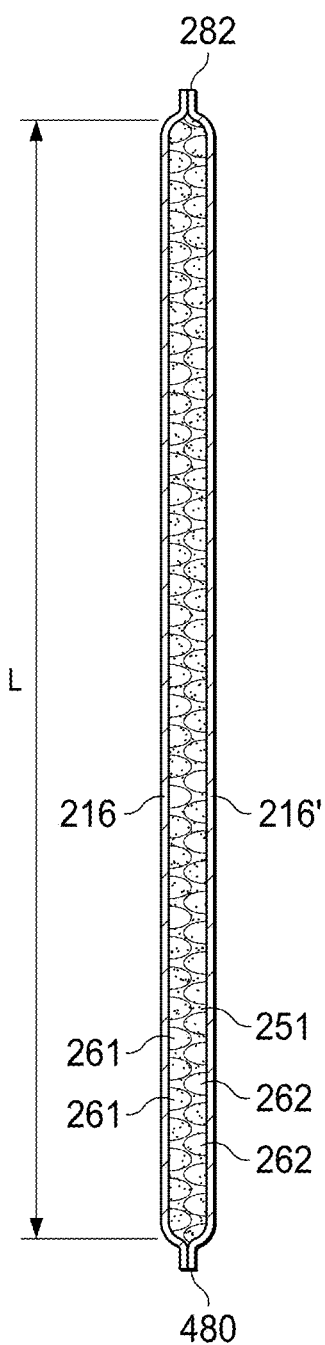
FIG. 35 is a cross sectional view of Section 35-35 of FIG. 33.

The example absorbent core 228 of the absorbent article 220 of FIGS. 31-32 is shown in isolation in FIGS. 33-35. The absorbent core 228 may comprises a front side 480, a rear side 282, and two longitudinal sides 284, 286 joining the front side 480 and the rear side 282. The absorbent core 228 may also comprise a generally planar top side and a generally planar bottom side. The front side 480 of the core is the side of the core intended to be placed towards the front waist edge 210 of the absorbent article. The core 228 may have a longitudinal axis 280' corresponding substantially to the longitudinal axis 280 of the absorbent article 220, as seen from the top in a planar view as in FIG. 28. The absorbent material may be distributed in higher amount towards the front side 480 than towards the rear side 282 as more absorbency may be required at the front in particular absorbent articles. The front and rear sides 480 and 282 of the core may be shorter than the longitudinal sides 284 and 286 of the core. The core wrap may be formed by two nonwoven materials, substrates, laminates, or other materials, 216, 216' which may be at least partially sealed along the sides 284, 286 of the absorbent core 228. The core wrap may be at least partially sealed along its front side 480, rear side 282, and two longitudinal sides 284, 286 so that substantially no absorbent material leaks out of the absorbent core wrap. The first material, substrate, or nonwoven 216 may at least partially surround the second material, substrate, or nonwoven 216' to form the core wrap, as illustrated in FIG. 34. The first material 216 may surround a portion of the second material 216' proximate to the first and second side edges 284 and 286.

The absorbent core may comprise adhesive, for example, to help immobilizing the SAP within the core wrap and/or to ensure integrity of the core wrap, in particular when the core wrap is made of two or more substrates. The adhesive may be a hot melt adhesive, supplied, by H.B. Fuller, for example. The core wrap may extend to a larger area than strictly needed for containing the absorbent material within.

The absorbent material may be a continuous layer present within the core wrap. Alternatively, the absorbent material may be comprised of individual pockets or stripes of absorbent material enclosed within the core wrap. In the first case, the absorbent material may be, for example, obtained by the application of a single continuous layer of absorbent material. The continuous layer of absorbent material, in particular of SAP, may also be obtained by combining two absorbent layers having discontinuous absorbent material application patterns, wherein the resulting layer is substantially continuously distributed across the absorbent particulate polymer material area, as disclosed in U.S. Pat. Appl. Pub. No. 2008/0312622A1 (Hundorf), for example. The absorbent core 228 may comprise a first absorbent layer and a second absorbent layer. The first absorbent layer may comprise the first material 216 and a first layer 261 of absorbent material, which may be 100% or less of SAP. The second absorbent layer may comprise the second material 216' and a second layer 262 of absorbent material, which may also be 100% or less of SAP. The absorbent core 228 may also comprise a fibrous thermoplastic adhesive material 251 at least partially bonding each layer of absorbent material 261, 262 to its respective material 216 or 216'. This is illustrated in FIGS. 34-35, as an example, where the first and second SAP layers have been applied as transversal stripes or "land areas" having the same width as the desired absorbent material deposition area on their respective substrate before being combined. The stripes may comprise different amounts of absorbent material (SAP) to provide a profiled basis weight along the longitudinal axis of the core 280. The first material 216 and the second material 216' may form the core wrap.

The fibrous thermoplastic adhesive material 251 may be at least partially in contact with the absorbent material 261, 262 in the land areas and at least partially in contact with the materials 216 and 216' in the junction areas. This imparts an essentially three-dimensional structure to the fibrous layer of thermoplastic adhesive material 251, which in itself is essentially a two-dimensional structure of relatively small thickness, as compared to the dimension in length and width directions. Thereby, the fibrous thermoplastic adhesive material may provide cavities to cover the absorbent material in the land areas, and thereby immobilizes this absorbent material, which may be 100% or less of SAP.

The thermoplastic adhesive used for the fibrous layer may have elastomeric properties, such that the web formed by the fibers on the SAP layer is able to be stretched as the SAP swell.

Superabsorbent Polymer (SAP)

The SAP useful with the present disclosure may include a variety of water-insoluble, but water-swellable polymers capable of absorbing large quantities of fluids.

The superabsorbent polymer may be in particulate form so as to be flowable in the dry state. Particulate absorbent polymer materials may be made of poly(meth)acrylic acid polymers. However, starch-based particulate absorbent polymer material may also be used, as well as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile.

The SAP may be of numerous shapes. The term "particles" refers to granules, fibers, flakes, spheres, powders, platelets and other shapes and forms known to persons skilled in the art of superabsorbent polymer particles. The SAP particles may be in the shape of fibers, i.e., elongated, acicular superabsorbent polymer particles. The fibers may also be in the form of a long filament that may be woven. SAP may be spherical-like particles. The absorbent core may comprise one or more types of SAP.

For most absorbent articles, liquid discharges from a wearer occur predominately in the front half of the absorbent article, in particular for a diaper. The front half of the article (as defined by the region between the front edge and a transversal line placed at a distance of half L from the front waist edge 210 or rear waist edge 212 may therefore may comprise most of the absorbent capacity of the core. Thus, at least 60% of the SAP, or at least 65%, 70%, 75%, 80%, or 85% of the SAP may be present in the front half of the absorbent article, while the remaining SAP may be disposed in the rear half of the absorbent article. Alternatively, the SAP distribution may be uniform through the core or may have other suitable distributions.

The total amount of SAP present in the absorbent core may also vary according to expected user. Diapers for newborns may require less SAP than infant, child, or adult incontinence diapers. The amount of SAP in the core may be about 5 to 60 g or from 5 to 50 g. The average SAP basis weight within the (or "at least one", if several are present) deposition area 8 of the SAP may be at least 50, 100, 200, 300, 400, 500 or more g/m². The areas of the channels (e.g., 226, 226', 227, 227') present in the absorbent material deposition area 8 are deduced from the absorbent material deposition area to calculate this average basis weight.

Core Wrap

The core wrap may be made of a single substrate, material, or nonwoven folded around the absorbent material, or may comprise two (or more) substrates, materials, or nonwovens which are attached to another. Typical attachments are the so-called C-wrap and/or sandwich wrap. In a C-wrap, as illustrated, for example, in FIGS. 29 and 34, the longitudinal and/or transversal edges of one of the substrates are folded over the other substrate to form flaps. These flaps are then bonded to the external surface of the other substrate, typically by gluing.

The core wrap may be formed by any materials suitable for receiving and containing the absorbent material. Typical substrate materials used in the production of conventional cores may be used, in particular paper, tissues, films, wovens or nonwovens, or laminates or composites of any of these.

The substrates may also be air-permeable (in addition to being liquid or fluid permeable). Films useful herein may therefore comprise micro-pores.

The core wrap may be at least partially sealed along all the sides of the absorbent core so that substantially no absorbent material leaks out of the core. By "substantially no absorbent material" it is meant that less than 5%, less than 2%, less than 1%, or about 0% by weight of absorbent material escape the core wrap. The term "seal" is to be understood in a broad sense. The seal does not need to be continuous along the whole periphery of the core wrap but may be discontinuous along part or the whole of it, such as formed by a series of seal points spaced on a line. A seal may be formed by gluing and/or thermal bonding.

If the core wrap is formed by two substrates 216, 216', four seals may be used to enclose the absorbent material 260 within the core wrap. For example, a first substrate 216 may be placed on one side of the core (the top side as represented in FIGS. 33-35) and extend around the core's longitudinal edges to at least partially wrap the opposed bottom side of the core. The second substrate 216' may be present between the wrapped flaps of the first substrate 216 and the absorbent material 260. The flaps of the first substrate 216 may be glued to the second substrate 216' to provide a strong seal. This so called C-wrap construction may provide benefits such as improved resistance to bursting in a wet loaded state compared to a sandwich seal. The front side and rear side of the core wrap may then also be sealed by gluing the first substrate and second substrate to another to provide complete encapsulation of the absorbent material across the whole of the periphery of the core. For the front side and rear side of the core, the first and second substrates may extend and may be joined together in a substantially planar direction, forming for these edges a so-called sandwich construction. In the so-called sandwich construction, the first and second substrates may also extend outwardly on all sides of the core and be sealed flat, or substantially flat, along the whole or parts of the periphery of the core typically by gluing and/or heat/pressure bonding. In an example, neither the first nor the second substrates need to be shaped, so that they may be rectangularly cut for ease of production but other shapes are also within the scope of the present disclosure.

The core wrap may also be formed by a single substrate which may enclose as in a parcel wrap the absorbent material and be sealed along the front side and rear side of the core and one longitudinal seal.

SAP Deposition Area

The absorbent material deposition area 208 may be defined by the periphery of the layer formed by the absorbent material 260 within the core wrap, as seen from the top side of the absorbent core. The absorbent material deposition area 208 may have various shapes, in particular, a so-called "dog bone" or "hour-glass" shape, which shows a tapering along its width towards the middle or "crotch" region of the core. In this way, the absorbent material deposition area 8 may have a relatively narrow width in an area of the core intended to be placed in the crotch region of the absorbent article, as illustrated in FIG. 28. This may provide better wearing comfort. The absorbent material deposition area 8 may also be generally rectangular, for example as shown in FIGS. 31-33, but other deposition areas, such as a rectangular, "T," "Y," "sand-hour," or "dog-bone" shapes are also within the scope of the present disclosure. The absorbent material may be deposited using any suitable techniques, which may allow relatively precise deposition of SAP at relatively high speed.

Channels

The absorbent material deposition area 208 may comprise at least one channel 226, which is at least partially oriented in the longitudinal direction of the article 280 (i.e., has a longitudinal vector component) as shown in FIGS. 28 and 29. Other channels may be at least partially oriented in the lateral direction (i.e., has a lateral vector component) or in any other direction. In the following, the plural form "channels" will be used to mean "at least one channel". The channels may have a length L' projected on the longitudinal axis 280 of the article that is at least 10% of the length L of the article. The channels may be formed in various ways. For example, the channels may be formed by zones within the absorbent material deposition area 208 which may be substantially free of, or free of, absorbent material, in particular SAP. In another example, the channels may be formed by zones within the absorbent material deposition area 208 where the absorbent material of the core comprises cellulose, airfelt, SAP, or combinations thereof and the channels may be substantially free of, or free of, absorbent material, in particular the SAP, cellulose, or airfelt In addition or alternatively, the channel(s) may also be formed by continuously or discontinuously bonding the top side of the core wrap to the bottom side of the core wrap through the absorbent material deposition area 208. The channels may be continuous, but it is also envisioned that the channels may be intermittent. The acquisition-distribution system or layer 250, or another layer of the article, may also comprise channels, which may or not correspond to the channels of the absorbent core.

In some instances, the channels may be present at least at the same longitudinal level as the crotch point C or the lateral axis 260 in the absorbent article, as represented in FIG. 28 with the two longitudinally extending channels 226, 226'. The channels may also extend from the crotch region 207 or may be present in the front waist region 205 and/or in the rear waist region 206 of the article.

The absorbent core 228 may also comprise more than two channels, for example, at least 3, at least 4, at least 5, or at least 6 or more. Shorter channels may also be present, for example in the rear waist region 206 or the front waist region 205 of the core as represented by the pair of channels 227, 227' in FIG. 28 towards the front of the article. The channels may comprise one or more pairs of channels symmetrically arranged, or otherwise arranged relative to the longitudinal axis 280.

The channels may be particularly useful in the absorbent core when the absorbent material deposition area is rectangular, as the channels may improve the flexibility of the core to an extent that there is less advantage in using a non-rectangular (shaped) core. Of course channels may also be present in a layer of SAP having a shaped deposition area.

The channels may be completely oriented longitudinally and parallel to the longitudinal axis or completely oriented transversely and parallel to the lateral axis, but also may have at least portions that are curved.

In order to reduce the risk of fluid leakages, the longitudinal main channels may not extend up to any of the edges of the absorbent material deposition area 208, and may therefore be fully encompassed within the absorbent material deposition area 208 of the core. The smallest distance between a channel and the closest edge of the absorbent material deposition area 208 may be at least 5 mm.

The channels may have a width Wc along at least part of their length which is at least 2 mm, at least 3 mm, at least 4 mm, up to for example 20 mm, 16 mm, or 12 mm, for example. The width of the channel(s) may be constant through substantially the whole length of the channel or may vary along its length. When the channels are formed by absorbent material-free zone within the absorbent material deposition area 208, the width of the channels is considered to be the width of the material free zone, disregarding the possible presence of the core wrap within the channels. If the channels are not formed by absorbent material free zones, for example mainly though bonding of the core wrap through the absorbent material zone, the width of the channels is the width of this bonding.

At least some or all of the channels may be permanent channels, meaning their integrity is at least partially maintained both in the dry state and in the wet state. Permanent channels may be obtained by provision of one or more adhesive materials, for example, the fibrous layer of adhesive material or construction glue that helps adhere a substrate with an absorbent material within the walls of the channel. Permanent channels may also be formed by bonding the upper side and lower side of the core wrap (e.g., the first substrate 216 and the second substrate 216') and/or the topsheet 224 to the backsheet 225 together through the channels. Typically, an adhesive may be used to bond both sides of the core wrap or the topsheet and the backsheet through the channels, but it is possible to bond via other known processes, such as pressure bonding, ultrasonic bonding, heat bonding, or combination thereof. The core wrap or the topsheet 224 and the backsheet 225 may be continuously bonded or intermittently bonded along the channels. The channels may advantageously remain or become visible at least through the topsheet and/or backsheet when the absorbent article is fully loaded with a fluid. This may be obtained by making the channels substantially free of SAP, so they will not swell, and sufficiently large so that they will not close when wet. Furthermore, bonding the core wrap to itself or the topsheet to the backsheet through the channels may be advantageous.

Barrier Leg Cuffs

The absorbent article may comprise a pair of barrier leg cuffs 34. Each barrier leg cuff may be formed by a piece of material which is bonded to the absorbent article so it may extend upwards from a wearer-facing surface of the absorbent article and provide improved containment of fluids and other body exudates approximately at the junction of the torso and legs of the wearer. The barrier leg cuffs are delimited by a proximal edge 64 joined directly or indirectly to the topsheet 224 and/or the backsheet 225 and a free terminal edge 266, which is intended to contact and form a seal with the wearer's skin. The barrier leg cuffs 234 extend at least partially between the front waist edge 210 and the rear waist edge 212 of the absorbent article on opposite sides of the longitudinal axis 280 and are at least present at the level of the crotch point (C) or crotch region. The barrier leg cuffs may be joined at the proximal edge 264 with the chassis of the article by a bond 265 which may be made by gluing, fusion bonding, or a combination of other suitable bonding processes. The bond 265 at the proximal edge 264 may be continuous or intermittent. The bond 265 closest to the raised section of the leg cuffs delimits the proximal edge 264 of the standing up section of the leg cuffs.

The barrier leg cuffs may be integral with the topsheet 224 or the backsheet 225 or may be a separate material joined to the article's chassis. Each barrier leg cuff 234 may comprise one, two or more elastic strings 235 close to the free terminal edge 266 to provide a better seal.

In addition to the barrier leg cuffs 234, the article may comprise gasketing cuffs 232, which are joined to the chassis of the absorbent article, in particular to the topsheet 224 and/or the backsheet 225 and are placed externally relative to the barrier leg cuffs. The gasketing cuffs 232 may provide a better seal around the thighs of the wearer. Each gasketing leg cuff may comprise one or more elastic strings or elastic elements 233 in the chassis of the absorbent article between the topsheet 224 and backsheet 225 in the area of the leg openings. All, or a portion of, the barrier leg cuffs and/or gasketing cuffs may be treated with a lotion or another skin care composition.

Acquisition-Distribution System

The absorbent articles of the present disclosure may comprise an acquisition-distribution layer or system 250 ("ADS"). One function of the ADS is to quickly acquire one or more of the fluids and distribute them to the absorbent core in an efficient manner. The ADS may comprise one, two or more layers, which may form a unitary layer or may remain as discrete layers which may be attached to each other. In an example, the ADS may comprise two layers: a distribution layer 254 and an acquisition layer 252 disposed between the absorbent core and the topsheet, but the present disclosure is not so limited.

In one example, the high loft, three-dimensional nonwoven materials of the present disclosure may comprise the topsheet and the acquisition layer as a laminate. A distribution layer may also be provided on the garment-facing side of the topsheet/acquisition layer laminate.

Carrier Layer

In an instance where the high loft, three-dimensional nonwoven materials of the present disclosure encompass a topsheet and acquisition layer laminate, the distribution layer may need to be supported by a carrier layer (not illustrated) that may comprise one or more nonwoven materials or other materials. The distribution layer may be applied to or positioned on the carrier layer. As such, the carrier layer may be positioned intermediate the acquisition layer and the distribution layer and be in a facing relationship with the acquisition layer and the distribution layer.

Distribution Layer

The distribution layer of the ADS may comprise at least 50% by weight of cross-linked cellulose fibers. The cross-linked cellulosic fibers may be crimped, twisted, or curled, or a combination thereof including crimped, twisted, and curled. This type of material is disclosed in U.S. Pat. Publ. No. 2008/0312622 A1 (Hundorf). The cross-linked cellulosic fibers provide higher resilience and therefore higher resistance to the first absorbent layer against the compression in the product packaging or in use conditions, e.g., under wearer weight. This may provide the core with a higher void volume, permeability, and liquid absorption, and hence reduced leakage and improved dryness.

The distribution layer comprising the cross-linked cellulose fibers of the present disclosure may comprise other fibers, but this layer may advantageously comprise at least 50%, or 60%, or 70%, or 80%, or 90%, or even up to 100%, by weight of the layer, of cross-linked cellulose fibers (including the cross-linking agents).

Acquisition Layer

If a three-dimensional nonwoven material of the present disclosure is provided as only the topsheet of an absorbent article, the ADS 250 may comprise an acquisition layer 252. The acquisition layer may be disposed between the distribution layer 254 and the topsheet 224. In such an instance, the acquisition layer 252 may be or may comprise a nonwoven material, such as a hydrophilic SMS or SMMS material, comprising a spunbonded, a melt-blown and a further spunbonded layer or alternatively a carded staple fiber chemical-bonded nonwoven. The nonwoven material may be latex bonded.

Fastening System

The absorbent article may comprise a fastening system. The fastening system may be used to provide lateral tensions about the circumference of the absorbent article to hold the absorbent article on the wearer as is typical for taped diapers. This fastening system may not be necessary for training pant articles since the waist region of these articles is already bonded. The fastening system may comprise a fastener such as tape tabs, hook and loop fastening components, interlocking fasteners such as tabs & slots, buckles, buttons, snaps, and/or hermaphroditic fastening components, although any other suitable fastening mechanisms are also within the scope of the present disclosure. A landing zone 244 is normally provided on the garment-facing surface of the front waist region 205 for the fastener to be releasably attached thereto.

Front and Rear Ears

The absorbent article may comprise front ears 246 and rear ears 240. The ears may be an integral part of the chassis, such as formed from the topsheet 224 and/or backsheet 226 as side panels. Alternatively, as represented on FIG. 28, the ears may be separate elements attached by gluing, heat embossing, and/or pressure bonding. The rear ears 240 may be stretchable to facilitate the attachment of the tabs 242 to the landing zone 244 and maintain the taped diapers in place around the wearer's waist. The rear ears 240 may also be elastic or extensible to provide a more comfortable and contouring fit by initially conformably fitting the absorbent article to the wearer and sustaining this fit throughout the time of wear well past when absorbent article has been loaded with fluids or other bodily exudates since the elasticized ears allow the sides of the absorbent article to expand and contract.

Elastic Waist Feature

The absorbent article 220 may also comprise at least one elastic waist feature (not represented) that helps to provide improved fit and containment. The elastic waist feature is generally intended to elastically expand and contract to dynamically fit the wearer's waist. The elastic waist feature may extend at least longitudinally outwardly from at least one waist edge of the absorbent core 228 and generally forms at least a portion of the end edge of the absorbent article. Disposable diapers may be constructed so as to have two elastic waist features, one positioned in the front waist region and one positioned in the rear waist region.

Color Signals

In a form, the absorbent articles of the present disclosure may have different colors in different layers, or portions thereof (e.g., the topsheet and the acquisition layer, the topsheet and the nonwoven core cover, a first portion and a second portion of a topsheet, a first portion and second portion of the acquisition layer). The different colors may be shade of the same color (e.g., dark blue and light blue) or may be actual different colors (e.g., purple and green). The different colors may have a Delta E in the range of about 1.5 to about 10, about 2 to about 8, or about 2 to about 6, for example. Other Delta E ranges are also within the scope of the present disclosure.

In an instance, various layers of the absorbent articles may be joined using a colored adhesive. The colored adhesive may be laid down on any suitable layer or layers in a pattern. The pattern of the adhesive may or may not complement the pattern of the topsheet. Such a pattern may increase the appearance of depth in an absorbent article. In certain instances, the colored adhesive may be blue.

In other instances, any of the layers may comprise indicia, such as a printed ink to aid in the appearance, depth impression, absorbency impression, or quality impression of the absorbent articles.

In other instances, the colors may be complimentary, or registered with, the patterns of three-dimensional features of the fabric 10 utilized as a component in an absorbent article. For example, a fabric having first and second zones of visually distinct patterns of three-dimensional features may also have printed thereon color to emphasize, highlight, contrast with, or otherwise change the visual appearance of the fabric 10. The color enhancements can be beneficial in communicating to a user of an absorbent article certain functional characteristics of the fabric 10 when in use. Thus color can be used in combination with structural, three-dimensional features in one component, or in combinations of components to deliver a visually distinctive absorbent article. For example, a secondary topsheet or acquisition layer may have printed thereon a pattern of color or colors that compliments the pattern of three-dimensional features of a fabric 10 utilized as a topsheet in an absorbent article. Another example is an absorbent article comprising 1) an absorbent core comprising a channel, 2) a topsheet with a three dimensional pattern registered or highlighting the channel or channels in the core, and 3) a graphic, colored component, printed ink, or indicia visible from the topsheet viewing (body contacting surface) or the backsheet viewing surface (garment facing surface) to further emphasize the functional features of the core channel or channels and the overall performance of the absorbent article.

Test Methods:
Compression Aging Test
Initial Caliper Measurement:
  Cut five 3 inch by 3 inch samples per nonwoven fabric to be measured.
  Number each sample from 1 to 5.
  Measure caliper at 0.5 kPa with Standard 65 mm foot using Thwing-Albert caliper tester according to standard procedures.
  Report initial caliper for each of the five samples.
  Report the average caliper of the five samples.
Aged Compression Method and Aged Caliper Measurement
  Stack the five samples in an alternating mode with each separated by a paper towel, the stack starting and ending with a Sample Number 1 and 5, respectively.
  Place the alternating stacked samples in an aluminum sample holder with an appropriate weight on top of the samples (4 KPa, 14 KPa or 35 KPa).
  Place the stacked samples with the weight in oven at 40° C. for 15 hours.
  Remove the weight after 15 hours, separate the samples and measure the caliper of each sample at 0.5 kPa with Standard 65 mm foot Thwing-Albert caliper tester according to standard procedures.
  Report aged caliper value for each of the five samples.
  Report the average aged caliper of the five samples.
Analysis Reports:
  Report average initial and aged calipers by position number
  Report Caliper Recovery Index:
    (Average Aged Caliper/Average Initial Caliper)*100
Localized Basis Weight Localized basis weight of the nonwoven fabric may be determined by several available techniques, but a simple representative technique involves a punch die having an area of 3.0 cm$^2$ which is used to cut a sample piece of the web from the selected region from the overall area of a nonwoven fabric. The sample piece is then weighed and divided by its area to yield the localized basis weight of the nonwoven fabric in units of grams per meter squared. Results are reported as a mean of 2 samples per selected region.

Fuzz Level Test

The Fuzz Level test is performed using a Sutherland Rub Tester (available from Thwing Albert Co, West Berlin, NJ) with an aluminum oxide cloth (extra smooth finish, 320 grit, 2 in. wide, 50 yard roll available from McMaster-Carr, Elmhurst, IL as part 8687A229 or equivalent) used as the abradant/receptor. After abrading a specimen, the aluminum oxide cloth and the specimen's surface are tape stripped using a fiber removal tape (3M #3187 adhesive tape, available from Netherland Rubber Company as a 2 in wide roll) for gravimetric analysis. A 2-lb detachable receptor block (also from Thwing Albert Co) is used.

Before use, inspect the rubber facing on the receptor block and the sample stage for ware/damage and replace if necessary as specified by the manufacturer (replacement foam is available from Thwing Albert Co).

Cut a piece of aluminum oxide cloth into a 7.5 in by 2.0 in strip. Mount the aluminum oxide cloth, using the clips on the side of the receptor block, such that the abrasive surface faces away from the block and the cloth is flat against the bottom surface of the receptor block.

Cut a specimen from the nonwoven fabric to be tested at least 12 cm in the machine direction (MD) and 6 cm in the cross direction (CD). Lay the specimen side to be tested facing down on a lab bench. Take a piece of 2-sided tape (3M #409, 2 in wide, differential tack, available from Netherland Rubber Co, Cincinnati OH or equivalent) 12 cm by 5.1 cm and remove the release paper. Position the tape with the adhesive side just exposed affixed to the nonwoven specimen with the long edge parallel to the MD of the specimen. Place the release paper onto the upward facing adhesive surface. Cut the specimen/tape laminate into a final dimension of 11.0 cm±0.1 cm MD by 4.0 cm±0.1 cm CD. Remove the release paper and affix the specimen to the center of a 65.5 mm wide by 210 mm long by 1.5 mm thick stainless steel plate (appropriate to attach to the sample stage of the Rub Tester). With the specimen facing upward, place a 2200 g weight (170 mm by 63 mm contact surface) on top of specimen for 20 seconds and then remove.

Secure the stainless steel plate to the sample stage of the Rub Tester specimen side facing upward, using the stage's integral clamps. Attach the detachable receptor block onto the reciprocating arm of the Rub tester with the abrasion surface facing the specimen. Set the Rub tester to perform 20 cycles at a rate of 21 cycles/sec.

Carefully remove the receptor block from the Rub Tester taking care not to lose any loose microfibers from either the aluminum oxide cloth surface or the specimen surface. Place the receptor block on the lab bench with the aluminum oxide cloth facing upward. Remove the steel plate with specimen from the Rub Tester and place specimen side facing upward onto the lab bench. Cut a piece of fiber removal tape 51 mm wide by 65.5 mm long. Fold approximate 5 mm of the tape's end over on top of itself at each end to facilitate handling the tape without touching the adhesive. Place onto a piece of light basis weight release paper (approximately 75 mm by 60 mm) to protect adhesive surface. Measure the mass of the tape/release paper and record to the nearest 0.0001 g. This is for tape-stripping fiber from the aluminum oxide cloth (Tape A). Prepare a second tape/release paper in like fashion for tape-stripping fibers from the surface of the abraded specimen (Tape B) and record its mass to the nearest 0.0001 g.

Take Tape A and remove the release paper. Holding both ends of the tape, gently blot the aluminum oxide cloth to remove the nonwoven fibers from the surface. Repeat as necessary to remove all fibers, taking care not to remove aluminum oxide particles. Replace its release paper, measure the mass of the tape/release paper and record the mass to the nearest 0.0001 g.

Subtract the tare mass from the final mass. This is Fiber Mass A. Take Tape B and remove the release paper. Holding both ends of the tape, place the tape centered on top of the specimen. Place the 2200 g weight onto the tape for 20 sec, and then remove. Holding both ends of the tape, lift the tape from the surface of the specimen. Replace its release paper, measure the mass of the tape/release paper and record the mass to the nearest 0.0001 g.

Subtract the tare mass from the final mass. This is Fiber Mass B. The Fuzz Level is the sum of Fiber Mass A and Fiber Mass B. In like fashion, repeat the test for a total of ten replicates. Average the ten specimens and record the Fuzz Mass to the nearest 0.10 mg. Calculate the Fuzz Level as the Average Fuzz Mass (mg)/44 cm$^2$ and report to the nearest 0.01 mg/cm$^2$.

Air Permeability Test

The Air Permeability Test is used to determine the level of air flow in cubic feet per minute (cfm) through a forming belt. The Air Permeability Test is performed on a Textest Instruments model FX3360 Portair Air Permeability Tester, available from Textest AG, Sonnenbergstrasse 72, CH 8603 Schwerzenbach, Switzerland. The unit utilizes a 20.7 mm orifice plate for air permeability ranges between 300-1000 cfm. If air permeability is lower than 300 cfm the orifice plate needs to be reduced; if higher than 1000 cfm the orifice plate needs to be increased. Air permeability can be measured in localized zones of a forming belt to determine differences in air permeability across a forming belt.

Test Procedure

1. Power on the FX3360 instrument.
2. Select a pre-determined style having the following setup:
   a. Material: Standard
   b. Measurement Property: Air Permeability (AP)
   c. Test Pressure: 125 Pa (pascals)
   d. T-factor: 1.00
   e. Test point pitch: 0.8 inch.
3. Position the 20.7 mm orifice plate on the top side of the forming belt (the side with the three-dimensional protrusions) at the position of interest.
4. Selecting "Spot Measurement" on the touch screen of the testing unit.
5. Reset the sensor prior to measurement, if necessary.
6. Once reset, select the "Start" button to begin measurement.
7. Wait until the measurement stabilizes and record the cfm reading on the screen.
8. Select the "Start" button again to stop measurement.
9. Results are reported as the average of three measurements.

In-Bag Stack Height Test

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 27). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention.

Further, to the extent that any meaning or definition of a term in this document conflicts with any meaning or definition of the same term in a document incorporated by reference, the meaning or definition assigned to that term in this document shall govern. While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A package comprising:
   a. a plurality of personal care articles;
   b. each of the plurality of personal care articles comprising a topsheet, the topsheet comprising a nonwoven substrate, wherein the nonwoven substrate comprises spunbond fibers, wherein the nonwoven substrate retains at least 60% of caliper after being tested according to the Compression Aging Test herein, the nonwoven substrate comprising:
   a first surface defining a plane of the first surface and a length and width defining an overall area;
   a plurality of three-dimensional features extending outwardly from the plane of the first surface, wherein the plurality of three-dimensional features comprise:
   a first zone within the overall area having a first pattern of first three-dimensional features having a basis weight having a first value; and
   a second zone within the overall area having a second pattern of three-dimensional features having a basis weight having a second value at least 1.5 times different than the first value;
   wherein the first pattern of three-dimensional features is different from the second pattern of three-dimensional features, and wherein the second zone at least partially surrounds the first zone, and
   a. the personal care articles being folded about a lateral axis and compressed in the package.

2. The package of claim 1, wherein the package has an in-bag stack height of less than about 100 mm, according to the In-Bag Stack Height Test herein.

3. The package of claim 1, wherein the package has an in-bag stack height of between about 80 mm and about 110 mm, according to the In-Bag Stack Height Test herein.

4. The package of claim 1, wherein the personal care articles are diapers.

5. A personal care article comprising:
   a. a topsheet, the topsheet comprising a nonwoven substrate, wherein the nonwoven substrate comprises spunbond fibers, the nonwoven substrate comprising:
      i. a first surface defining a plane of the first surface and a length and width defining an overall area;
      ii. a plurality of three-dimensional features extending outwardly from the plane of the first surface, wherein the plurality of three-dimensional features comprise:
         a. a first zone within the overall area having a first pattern of first three-dimensional features having a basis weight having a first value; and
         b. a second zone within the overall area having a second pattern of three-dimensional features having a basis weight having a second value at least 1.5 times different than the first value;
         c. wherein the first pattern of three-dimensional features is visually discernible from the second pattern of three-dimensional features, and wherein the second zone at least partially surrounds the first zone, and
   b. a backsheet;
   c. an absorbent core positioned at least partially intermediate the topsheet and the backsheet; and
   d. wherein the topsheet retains at least 60% of caliper after being tested according to the Compression Aging Test herein.

6. The personal care article of claim 5, wherein the personal care articles are diapers.

7. The personal care article of claim 5, wherein the personal care articles are sanitary napkins.

8. The package of claim 1, wherein the nonwoven substrate comprises starch, starch derivatives, cellulose, or cellulose derivatives.

9. The personal care article of claim 5, wherein the nonwoven substrate comprises starch, starch derivatives, cellulose, or cellulose derivatives.

10. The package of claim 1, wherein the first zone is free from overlap with the second zone.

11. The package of claim 1, wherein the first zone occupies a first portion of the overall area, wherein the second zone occupies a second portion of the overall area, and wherein the first portion is free from overlap with the second portion.

12. The personal care article of claim 5, wherein the first zone is free from overlap with the second zone.

13. The personal care article of claim 5, wherein the first zone occupies a first portion of the overall area, wherein the second zone occupies a second portion of the overall area, and wherein the first portion is free from overlap with the second portion.

* * * * *